US009994554B2

(12) United States Patent
Connor et al.

(10) Patent No.: US 9,994,554 B2
(45) Date of Patent: Jun. 12, 2018

(54) BARBITURATE AND THIOBARBITURATE COMPOUNDS FOR USE IN CANCER THERAPY

(71) Applicant: NUHOPE, LLC, Hershey, PA (US)

(72) Inventors: James R. Connor, Hershey, PA (US); Sang Yong Lee, Palmyra, PA (US); Thomas James Brown, Edinburgh (GB); Phillip Martin Cowley, Edinburgh (GB)

(73) Assignee: NUHOPE LLC, Hershey, PA (US)

( * ) Notice: Subject to any disclaimer, the term of this patent is extended or adjusted under 35 U.S.C. 154(b) by 0 days. days.

(21) Appl. No.: 15/843,192

(22) Filed: Dec. 15, 2017

(65) Prior Publication Data
US 2018/0134691 A1 May 17, 2018

Related U.S. Application Data

(62) Division of application No. 14/239,294, filed as application No. PCT/IB2012/054160 on Aug. 15, 2012, now Pat. No. 9,878,998.

(Continued)

(51) Int. Cl.
C07D 405/06 (2006.01)
C07D 239/60 (2006.01)
C07D 401/06 (2006.01)
A61K 31/513 (2006.01)
C07D 403/06 (2006.01)

(52) U.S. Cl.
CPC .......... C07D 405/06 (2013.01); A61K 31/513 (2013.01); C07D 239/60 (2013.01); C07D 401/06 (2013.01); C07D 403/06 (2013.01)

(58) Field of Classification Search
None
See application file for complete search history.

(56) References Cited

U.S. PATENT DOCUMENTS

| 2005/0119243 A1 | 6/2005 | Harris et al. |
| 2010/0081678 A1 | 4/2010 | Crooks et al. |
| 2015/0065531 A1 | 3/2015 | Connor et al. |

FOREIGN PATENT DOCUMENTS

| WO | 01/93841 A2 | 12/2001 |
| WO | 03/074497 A1 | 9/2003 |

(Continued)

OTHER PUBLICATIONS

Rajput et al., Chinese Journal of Catalysts 34 (2013) 1697-1704.*

(Continued)

Primary Examiner — Karl J Puttlitz
(74) Attorney, Agent, or Firm — Heslin Rothenberg Farley & Mesiti P.C.

(57) ABSTRACT

Provided are methods and compositions for use in therapy, and in particular for treating cancer, preferably drug-resistant cancer, and/or radiation resistant cancer. The compounds may be used for reducing tumor size in a mammalian subject and for inducing apoptosis in a tumor cell. The methods are effective on tumor cells that are resistant to drugs such as temozolomide, doxorubicin, and geldanamycin, as well as non-resistant tumor cells. Further provided are barbiturate and thiobarbiturates diene compounds for use in treating cancer, and uses, methods and compositions relating to these compounds.

16 Claims, 16 Drawing Sheets

Related U.S. Application Data

(60) Provisional application No. 61/524,826, filed on Aug. 18, 2011.

(56) References Cited

FOREIGN PATENT DOCUMENTS

| WO | 2007/120842 A2 | 10/2007 |
|---|---|---|
| WO | 2009/018219 A2 | 2/2009 |
| WO | 2009/073620 A2 | 6/2009 |
| WO | 2011/094708 A2 | 8/2011 |

OTHER PUBLICATIONS

Burden, D.A., et al., "Mechanism of action of eukaryotic topoisomerase II and drugs targeted to the enzyme", *Biochimica et Biophysics Acta*, vol. 1400, pp. 139-154 (1998).

Capranico, G., et al., "Development of DNA Topoisomerase-Related Therapeutics: A Short Perspective of New Challenges", *Curr Med Chem Anticancer Agents*, vol. 4, pp. 335-345 (2004).

Wang, L., et al., "Catalytic Inhibitors of Topoisomerase II Are DNA-Damaging Agents: Induction of Chromosomal Damage by Merbarone and ICRF-187", *Environmental and Molecular Mutagenesis*, vol. 39, pp. 348-356 (2002).

Mautner, H.G., et al., "2-Selenobarbiturates. Studies of Some Analogous Oxygen, Sulfur, and Selenium Compounds", *Journal American Chemical Society*, vol. 81, pp. 6270-6273 (1959).

Lee, S.Y., et al., "HFE polymorphisms influence the response to chemotherapeutic agents via induction of p16INK4A", *International Journal of Cancer*, vol. 129, pp. 2104-2114 (2011).

Adamson, J., et al., "Reactions of 1,3-diethyl-2-thiobarbituric acid with aldehydes: formation of arylbis(1,3-diethyl-2-thiobarbitur-5-yl)methanes and crystallographic evidence for ground state polarisation in 1,3-diethyl-5-[4-(dimethylamino)benzylidene]-2-thiobarbituric acid", *Journal of the Chemical Society, Perkins Transactions 1*, pp. 2483-2488 (1999).

Haldar, M.K., et al., "Synthesis of barbiturate-based methionine aminopeptidase-1 inhibitors", *Bioorganic & Medicinal Chemistry Letters*, vol. 18, No. 7, pp. 2373-2376 (2008).

Friedman, G.D., "Barbiturates, Benzodiazepines and Lung Cancer", *International Journal of Epidemiology*, London, vol. 12, No. 3, pp. 375-376 (1983).

Althaus F.R., et al., "Tumor-promoting barbiturates act on DNA repair of cultured hepatocytes", *Mutation Research Letters*, Elsevier, vol. 173, No. 2, pp. 147-152 (1986).

Motesharei, K., et al., "Molecular Recognition on Functionalized Self-Assembled Monolayers of Alkanethiols on Gold", *Journal of the American Chemical Society*, vol. 120, pp. 7328-7336 (1998).

Suvorov, N.N., et al., "Indole Derivatives. XCIII. Synthesis of 5-(3-Indolylmethyl) Barbituric and 5-(3-Indolylmethyl) Thiobarbituric Acids", *Database Chemical Abstracts*, Chemi [Online] (1974).

Semenza, G.L., "Targeting HIF-1 For Cancer Therapy", *Nature Reviews*, vol. 3, pp. 721-732 (2003).

\* cited by examiner

BARBITURATE AND THIOBARBITURATE COMPOUNDS FOR USE IN CANCER THERAPY

CROSS REFERENCE TO RELATED APPLICATIONS

This application is a divisional application of U.S. application Ser. No. 14/239,294, which is a national stage filing under section 371 of International Application No. PCT/IB2012/054160, filed on Aug. 15, 2012, and published in English on Feb. 21, 2013 as WO/2013/024447, and claims priority to U.S. Provisional Application No. 61/524,826, filed on Aug. 18, 2011. The entire contents of each of the prior applications are hereby incorporated herein by reference.

FIELD OF THE INVENTION

The present application describes compounds, compositions, uses and methods for therapy, especially cancer therapy. In particular, the application relates to compounds for use in the treatment of cancer generally, as well as in the treatment of cancer that is resistant to existing treatment, including drug resistant cancers and tumors, and radiation resistant cancers and tumors. Brain cancer (brain tumors) and ovarian cancer (ovarian tumors) are of particular interest.

BACKGROUND OF THE INVENTION

Chemotherapy drugs for the treatment of cancer are generally directed to inhibiting the reproduction of malignant cells and killing malignant cells, thereby preventing tumor growth or reducing tumor size. Some of the most commonly used cancer chemotherapy drugs include alkylating drugs, anthracycline antibiotics, taxanes, alkaloids, and topoisomerase inhibitors.

Alkylating drugs are the oldest anti-cancer drugs and are used to treat many types of cancer. Alkylating drugs are typically methylating agents or chloroethylating agents which cause apoptosis in malignant cells. Temozolomide, (brand name, Temodar®, Schering-Plough Corp.), is an oral alkylating agent used in the treatment of brain cancer (1-3), e.g., glioblastoma multiforme and oligodendroglioma, and of melanoma (4, 5). It has also been used to treat prostate cancer, pancreatic carcinoma, soft tissue sarcoma, and renal cell carcinoma (6-12). Temozolomide inhibits cell reproduction by inhibiting DNA replication (13).

Temodar® has unique characteristics compared with other alkylating agents. For example, it is administered orally, forms a small lipophilic molecule that crosses the blood-brain barrier, is less toxic than other alkylating agents, does not chemically cross-link DNA, and is effective on a wide variety of cancers. However, although Temodar® is the current chemotherapeutic standard for treating brain tumors, as many as 50% of brain tumors are resistant to Temodar® therapy (14, 15). Resistance to Temodar® is also found in melanoma (16, 17).

Anthracycline antibiotics include doxorubicin, daunorubicin, epirubicin, idarubicin, valrubicin and are commonly used to treat most types of cancers, e.g., leukemias, Hodgkin's lymphoma, cancers of the bladder, breast, stomach, lung, ovaries, and thyroid, soft tissue sarcoma, multiple myeloma, and others. Doxorubicin acts by intercalating into DNA and preventing transcription and DNA synthesis (18). Doxorubicin is also a topoisomerase I inhibitor (19) and IIα poison (20).

Topoisomerase inhibiting drugs include doxorubicin, etoposide, and teniposide, and are generally used to treat leukemia, lung, ovarian, and gastrointestinal cancers (21, 22). These drugs act by inhibiting topoisomerase I or topoisomerase IIα or IIβ, thereby preventing DNA replication, recombination, transcription and chromosome segregation (23, 24).

Although these drugs are initially effective, tumor cells have, or may develop resistance to them. There are multiple mechanisms by which the cancer cells develop resistance to topoisomerase inhibitors. For example, endogenously produced ganglioside GM3 was shown to be involved in etoposide and doxorubicin resistance by up-regulating Bcl-2 expression in 3LL Lewis lung carcinoma cell line (25).

Primary non-malignant and malignant brain and central nervous system tumors are expected to occur in more than 64,000 people in the United States in 2011 (26). Gliomas represent 31% of all primary brain and central nervous system tumors, and over 80% of gliomas are malignant (26). The mortality rate of primary malignant brain and CNS tumors is high; approximately 22,020 new adult cases of brain and other nervous system cancers and 13,140 deaths occurred in 2010 (27). Malignant brain tumors account for 1.4% of all primary malignant cancers, and 2.2% of all cancer related deaths (28). Despite access to state-of-the-art surgical, radiation, and chemotherapies, survival rates for patients with newly diagnosed glioblastoma multiforme, the most common malignant glioma, was very poor. The median survival for GBM patients was 14.6 months and the 2 year survival of patients with GBM was 10.4% for radiotherapy alone and only 26.5% undergoing combined therapy treatment of Temodar® and radiation (29). The two to five year survival rate for malignant glioma has remained unchanged over the past 30 years. Thus, despite aggressive treatments, brain tumors generally recur, and are fatal.

Ovarian cancer is the second most common gynaecologic cancer, and represents the leading cause of gynecologic cancer-related death in Europe and United States (30, 31). It is estimated that 21,880 new cases and 13,850 deaths from ovarian cancer occurred in the United States in 2010 (27). Treatment of ovarian cancer is surgery and chemotherapy, and sometimes radiotherapy. Platinum based compounds are standard first-line agents for ovarian cancer and initial response rates are high (32). However, subsequent relapse with acquired platinum resistance is frequent and closely linked to the poor survival associated with this cancer.

Accordingly, a significant clinical need exists for additional chemotherapeutic agents that are toxic to a wide range of tumors and tumor cell types, in particular tumors and tumor cells that are resistant to current treatments such as radiotherapy, and resistant to other chemotherapeutic drugs. Therefore, in a first embodiment of the present invention it is an aim to provide solutions to meet this need.

There is also a continuing requirement, not only to provide treatments as described above, but to improve treatments for all forms of cancer. In other words, there is a clinical need for improved compounds and compositions for treating brain cancers, ovarian cancers as well as other cancers more generally. In a second embodiment it is an aim to provide further compounds and compositions for treating cancers generally, and brain and ovarian tumors specifically.

It has been known that barbituric acid derivatives have value as therapeutic agents for many years. In the past they have been employed for their central nervous system depressant activity, finding use inter alia as sedatives and anti-convulsants. Due to their toxicity, they have largely been replaced by benzodiazepines in such treatments.

However, more recently barbiturates have found new indications as potential treatments for a variety of diseases. For example, Ciustea et al. disclose inter alia barbiturates for treating the vaccinia virus (smallpox) ("Identification of non-nucleoside DNA synthesis inhibitors of vaccinia virus by high throughput screening", J. Med. Chem., 51, 6563-6570, 2008).

Barbiturates have also been proposed as cancer treatments. For example, WO 01/93841 discloses certain barbituric acid analogues as therapeutic agents which inhibit HIF-1 activity. This may be used to treat proliferative conditions, such as cancer.

It is also known to use merocyanine dyes (compounds related to thiobarbiturates) to treat leukemia (WO 89/12080). This treatment involves the use of the dye to photosensitize leukemic cells, followed by exposure to light. Merocyanine 540 has also been shown to have apoptotic activity (Chen Yen-Chou et al., "Photodynamic anticancer agent merocyanine 540 inhibits cell growth by apoptosis". Anticancer Research, 16, 5A, 2781-2788, 1996; D. L. Traul et al., "Induction of apoptosis and necrosis in leukemia and solid tumor cells by merocyanine 540-mediated PDT", Photochemistry and Photobiology, 59, Spec. Issue, 70S, 1994; Shazib et al., "Caspase proteases mediate apoptosis induced by anticancer agent preactivated MC540 in human tumor cell lines", Cancer Letters, 128, 1, 11-22, Jun. 5, 1998; Sieber et al., "Second generation merocyanine photosensitizers for photodynamic therapy", Trends in Photochemistry & Photobiology, 10, 1-13, 2003).

Some barbiturate derivatives have been proposed as possible modulators of apoptosis and therefore possible anticancer agents (WO2011/094708). Several have been proposed as possible breast cancer and prostate cancer treatments (WO2009/065897). Further proposed activities include: as inhibitors of MALT1 proteolytic and/or autoproteolytic activity (WO2009/065897); as a RAD51 protein modulator to protect against DNA damage (WO2009/018219); as c-Rel activity inhibitors (WO2007/120842) for treating inter alia cancer; as Pin-1 modulators (WO2003/074497) for treating inter alia cancer; as potential cancer treatments when combined with indole (Palwinder et al., "Design, synthesis and anticancer activities of hybrids of indole and barbituric acid—identification of highly promising leads", Bioorganic & Medicinal Chemistry Letters, 19, 11, 3054-3058, 2009); and as inhibitors decreasing the proliferation of cervix cancer cells (Shuangding et al., "Multidentate small-molecule inhibitors of vaccinia III-related (VHR) phosphatase decrease proliferation of cervix cancer cells", Journal of Medicinal Chemistry, 52, 21, 6716-6723, 2009).

However, to date, whilst some barbiturates and their analogues have received attention, none have been found which satisfactorily solve the problems underlying the present invention discussed above. The present inventors have surprisingly discovered a class of barbiturates and related compounds which may provide therapies, such as treatments for cancer, especially for cancers that are resistant to current drugs such as Temodar®, and for cancers that are resistant to radiation. These compounds may be used to improve treatments for all forms of cancer.

SUMMARY OF THE INVENTION

In a first embodiment of the invention, methods and compositions for use in therapy, for example treating cancer, preferably drug-resistant cancer or radiation resistant cancer, typically (but not exclusively) by reducing tumor size, and/or inducing apoptosis in a tumor cell, and treating a disease are provided. The methods comprise administering to a mammalian subject a therapeutically effective amount of one or more compounds of Formulae I to XXII, described herein, or a derivative, homologue, prodrug, solvate, or pharmaceutical salt thereof.

According to one aspect of the present invention, there is provided a method for reducing tumor size in a mammalian subject comprising administering to the mammalian subject a therapeutically effective amount of the compound of Formula I:

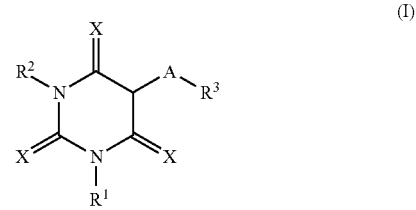

(I)

wherein:

X is O or S;

A is an alkenylidene;

$R^1$ and $R^2$ are independently selected from the group consisting of (i) an alkyl containing from 1 to 10 carbon atoms, which may be linear or branched, (ii) an alkenyl containing from 2 to 10 carbon atoms, which may be linear or branched; and (iii) a hydrogen; and $R^3$ is a phenyl or heteroaryl, which may be linear or branched, and optionally substituted with a heteroalkyl, which may be linear or branched, or a derivative, homologue, prodrug or pharmaceutical salt thereof, preferably wherein the tumor is a drug-resistant tumor, and/or a radiation resistant tumor.

Preferably, the compound is of Formula II:

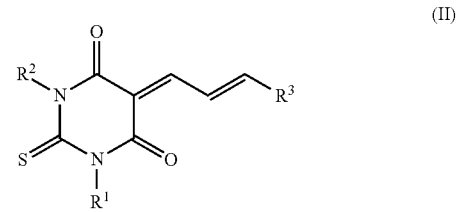

(II)

wherein:

$R^1$ and $R^2$ are independently selected from the group consisting of (i) an alkyl containing from 1 to 10 carbon atoms, which may be linear or branched, (ii) an alkenyl containing from 2 to 10 carbon atoms, which may be linear or branched; and (iii) a hydrogen; and $R^3$ is a phenyl or heteroaryl, which may be linear or branched, and optionally substituted with a heteroalkyl, which may be linear or branched, or a derivative, homologue, prodrug or pharmaceutical salt thereof.

Preferably, the compound is of Formula III:

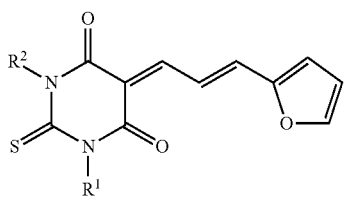
(III)

wherein:
  $R^1$ and $R^2$ are independently selected from the group consisting of (i) an alkyl containing from 1 to 10 carbon atoms, which may be linear or branched, (ii) an alkenyl containing from 2 to 10 carbon atoms, which may be linear or branched; and (iii) a hydrogen, or a derivative, homologue, prodrug or pharmaceutical salt thereof.

Preferably, the compound is selected from the group consisting of compounds (IV) to (XXII) below:

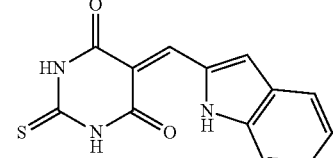
(IV)

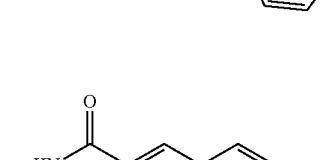
(V)

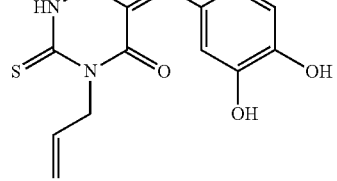
(VI)

(VII)

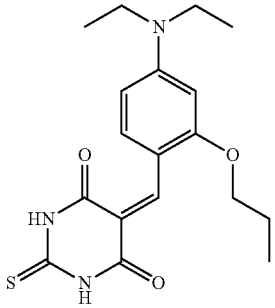
(VIII)

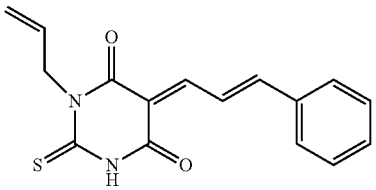
(IX)

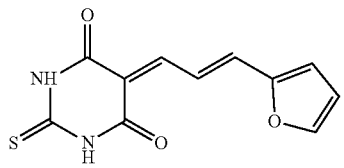
(X)

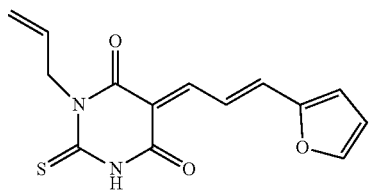
(XI)

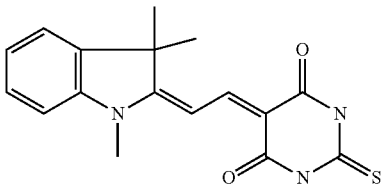
(XII)

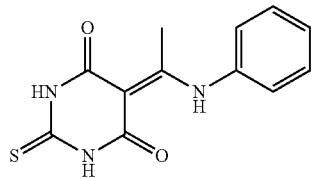
(XIII)

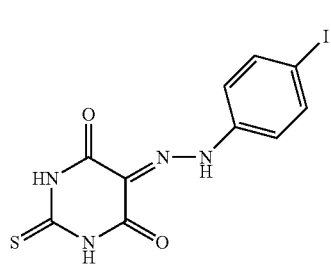
(XIV)

(XV) 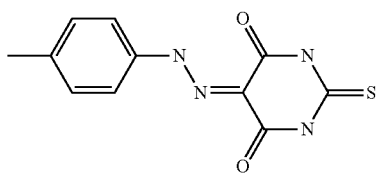

(XVI) 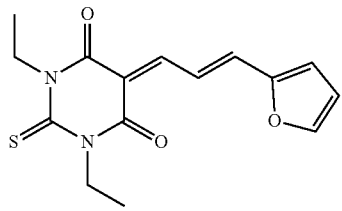

(XVII) 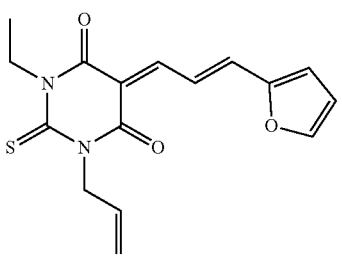

(XVIII) 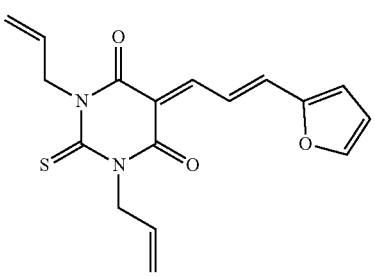

(XIX) 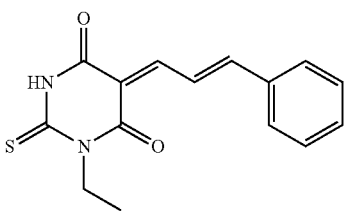

(XX) 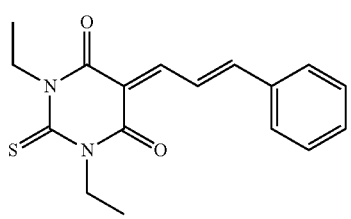

(XXI) 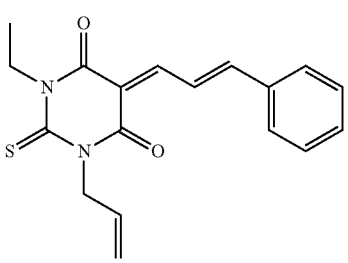

(XXII) 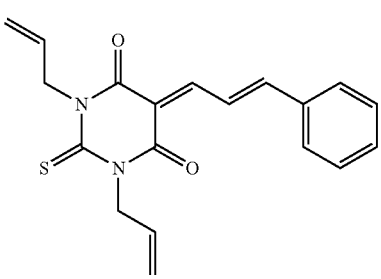

Preferably, the tumor is selected from the classes of tumors consisting of carcinomas, sarcomas, leukemias, lymphomas, myelomas, central nervous system tumors, peripheral nerve tumors, melanomas and metastatic tumors.

Preferably, the tumor is within the cranium or vertebral column.

Preferably, the tumor is selected from the group consisting of glioma, brain stem glioma, mixed glioma, optic nerve glioma, astrocytoma, meningioma, pituitary adenoma, vestibular schwannoma, primary CNS lymphoma, primary neuroectodermal tumor, neurofibroma, schwannoma, leptomeningeal tumors, germ cell tumor, choriocarcinoma, endodermal sinus tumor, chordoma, craniopharyngioma, ependymoma, subependymoma, medulloblastoma, oligodendroglioma, pituitary tumors, pineal tumor, rhabdoid tumor and tumors that have metastasized to the brain.

Preferably, the tumor comprises drug-resistant cells, and/or radiation-resistant cells. Preferably, the tumor comprises cells resistant to temozolomide, geldanamycin, geldanamycin derivatives, and/or doxorubicin.

Preferably, the compound is administered once, twice or three times a week. Preferably, the compound is administered once a week. Preferably, the therapeutically effective amount of the compound is from 1 mg/kg to 100 mg/kg in a single weekly dose administered parenterally. Preferably, the therapeutically effective amount of the compound is from 10 mg/kg to 50 mg/kg in a single weekly dose administered parenterally.

According to another aspect of the present invention, there is provided a method for inducing apoptosis in a tumor cell in a mammalian subject comprising administering to the mammalian subject a therapeutically effective amount of the compound of Formula I:

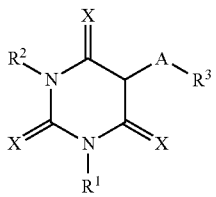

(I)

wherein:
X is O or S;
A is an alkenylidene;
$R^1$ and $R^2$ are independently selected from the group consisting of (i) an alkyl containing from 1 to 10 carbon atoms, which may be linear or branched, (ii) an alkenyl containing from 2 to 10 carbon atoms, which may be linear or branched; and (iii) a hydrogen; and R³ is a phenyl or heteroaryl, which may be linear or branched, and optionally substituted with a heteroalkyl, which may be linear or branched, or a derivative, homologue, prodrug or pharmaceutical salt thereof, preferably wherein the tumor cell is a drug-resistant tumor cell, and/or a radiation-resistant tumor cell.

Preferably, the compound is of Formula II:

(II)

wherein:
- R¹ and R² are independently selected from the group consisting of (i) an alkyl containing from 1 to 10 carbon atoms, which may be linear or branched, (ii) an alkenyl containing from 2 to 10 carbon atoms, which may be linear or branched; and (iii) a hydrogen; and
- R³ is a phenyl or heteroaryl, which may be linear or branched, and optionally substituted with a heteroalkyl, which may be linear or branched, or a derivative, homologue, prodrug or pharmaceutical salt thereof.

Preferably, the compound is of Formula III:

(III)

wherein:
- R¹ and R² are independently selected from the group consisting of (i) an alkyl containing from 1 to 10 carbon atoms, which may be linear or branched, (ii) an alkenyl containing from 2 to 10 carbon atoms, which may be linear or branched; and (iii) a hydrogen, or a derivative, homologue, prodrug or pharmaceutical salt thereof.

Preferably, the compound is selected from the group consisting of compounds (IV) to (XXII) below:

(IV)

(V)

(VI)

(VII)

(VIII)

(IX)

(X)

(XI)

(XII) 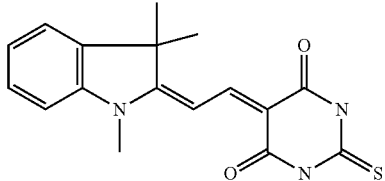

(XIII) 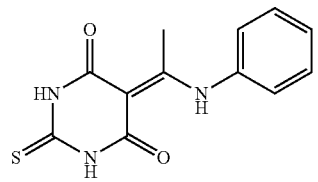

(XIV) 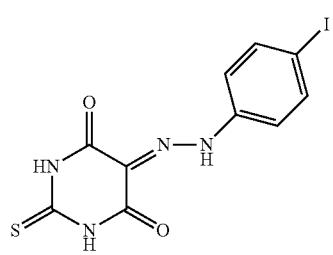

(XV) 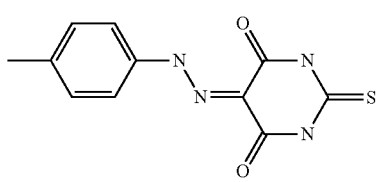

(XVI) 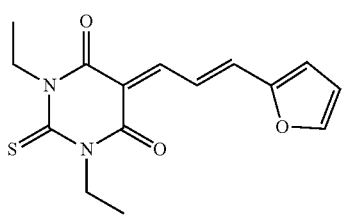

(XVII) 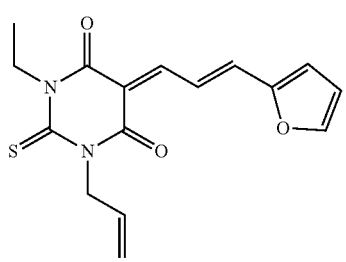

(XVIII) 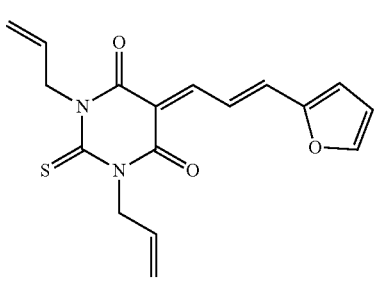

(XIX) 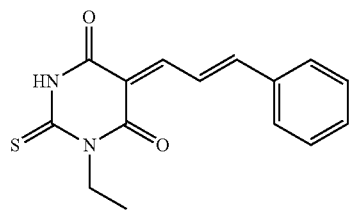

(XX) 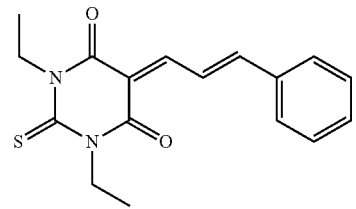

(XXI) 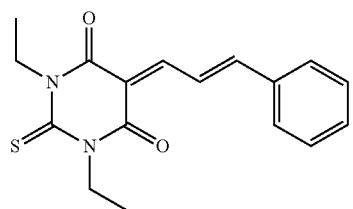

(XXII) 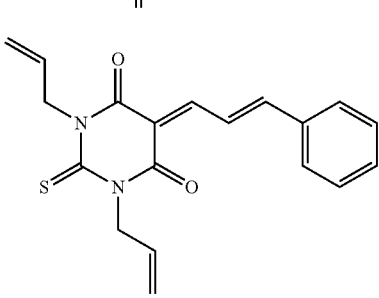

Preferably, the tumor comprises drug-resistant cells, and/or radiation resistant cells. Preferably, the tumor cell is resistant to temozolomide, geldanamycin, geldanamycin derivatives, and/or doxorubicin.

Preferably, the tumor cell is selected from the group consisting of pituitary adenoma, vestibular schwannoma, primary CNS lymphoma, primary neuroectodermal tumor, neuroblastoma, neurofibroma, malignant peripheral nerve sheath tumor, schwannoma, skin cancer, lung cancer, colon cancer, pancreatic cancer, ovarian cancer, epithelial carcinoma, squamous cell carcinoma, basal cell carcinoma, osteosarcoma, synovialsarcoma, liposarcoma, angiosarcoma, rhapdosarcoma, fibrosarcoma, lymphoblastic leukemia myelogenous leukemias, T-cell leukemia, hairy-cell leukemia. T-cell lymphomas, B-cell lymphomas. Hodgkin lymphomas, non-Hodgkin lymphoma, lymphoproliferative lymphomas, central nervous system cancer and metastatic cancers.

Preferably, the compound is administered weekly. Preferably, the therapeutically effective amount of the compound is from 1 mg/kg to 100 mg/kg in a single weekly dose administered parenterally. Preferably, the therapeutically effective amount of the compound is from 10 mg/kg to 50 mg/kg in a single weekly dose administered parenterally.

According to another aspect of the present invention, there is provided a compound of Formula XII:

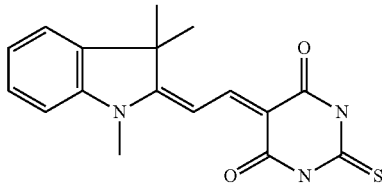

(XII)

or a derivative, homologue, prodrug or pharmaceutical salt thereof.

According to another aspect of the present invention, there is provided a compound of Formula XIII:

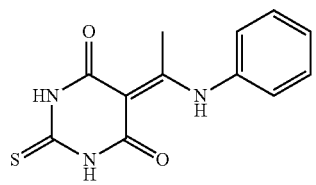

(XIII)

or a derivative, homologue, prodrug or pharmaceutical salt thereof.

According to another aspect of the present invention, there is provided a compound of Formula XIV:

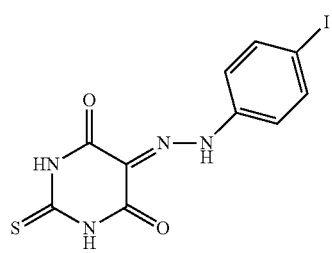

(XIV)

or a derivative, homologue, prodrug or pharmaceutical salt thereof.

According to another aspect of the present invention, there is provided a compound of Formula XV:

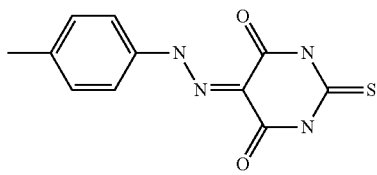

(XV)

or a derivative, homologue, prodrug or pharmaceutical salt thereof.

According to another aspect of the present invention, there is provided a compound of Formula XVI:

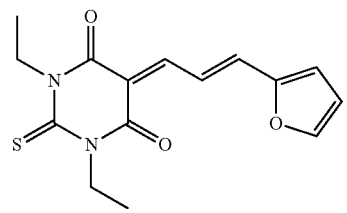

(XVI)

or a derivative, homologue, prodrug or pharmaceutical salt thereof.

According to another aspect of the present invention, there is provided a compound of Formula XVII:

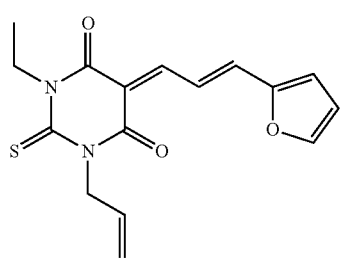

(XVII)

or a derivative, homologue, prodrug or pharmaceutical salt thereof.

According to another aspect of the present invention, there is provided a compound of Formula XVIII:

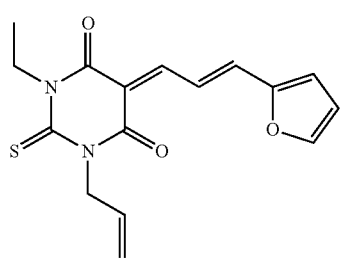

(XVIII)

or a derivative, homologue, prodrug or pharmaceutical salt thereof.

According to another aspect of the present invention, there is provided a compound of Formula XIX:

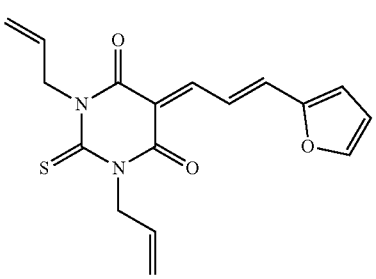

(XIX)

or a derivative, homologue, prodrug or pharmaceutical salt thereof.

According to another aspect of the present invention, there is provided a compound of Formula XX:

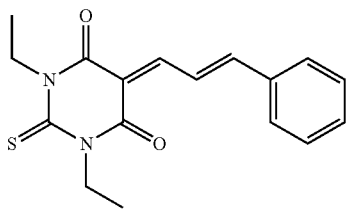

(XX)

or a derivative, homologue, prodrug or pharmaceutical salt thereof.

According to another aspect of the present invention, there is provided a compound of Formula XXI:

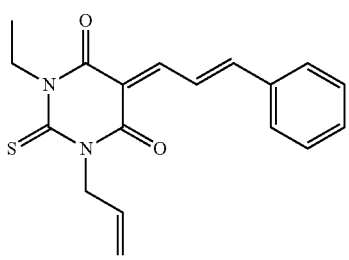

(XXI)

or a derivative, homologue, prodrug or pharmaceutical salt thereof.

According to another aspect of the present invention, there is provided a compound of Formula XXII:

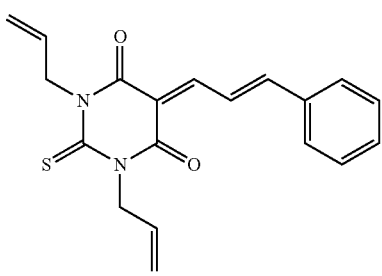

(XXII)

or a derivative, homologue, prodrug or pharmaceutical salt thereof.

According to a further aspect of the present invention, there is provided a method for treating a disease comprising administering to a mammalian subject a therapeutically effective amount of a compound as described herein. Preferably, the disease is cancer. Examples of preferred types of cancer are described elsewhere herein. Preferably, the disease is drug-resistant cancer, and/or a radiation-resistant cancer. Preferably, the disease is selected from the group consisting of neuroblastoma, neurofibroma, malignant peripheral nerve sheath tumor, head and neck cancer, breast cancer, ovarian cancer, renal medullary carcinoma, prostate cancer, gastric cancer, cervical cancer, brain cancer, peripheral nerve tumors, central nervous system cancer, lung cancer, leukaemia (for example lymphocytic leukemia), colorectal cancer, colon cancer, spinal tumor (neoplasm), bone cancer, liver cancer, lymphoma, melanoma, pancreatic cancer, thyroid cancer, uterine sarcoma and testicular cancer.

According to one aspect of the present invention, there is provided a compound or composition as described herein for use in therapy.

According to another aspect of the present invention, there is provided use of a compound or composition as described herein in the manufacture of a pharmaceutical effective in a therapy.

Preferably, the therapy is the treatment of cancer. Examples of preferred types of cancer are described elsewhere herein, for example with reference to the methods of the present invention.

Preferably, the therapy is the treatment of a drug-resistant cancer, and/or a radiotherapy-resistant cancer. In this respect, it will be appreciated that a drug resistant cancer is a cancer that has shown resistance against one or more known anti-cancer drugs, for example Temodar®. The resistance shown may be total or partial. In this respect a radiotherapy-resistant cancer is a cancer that has shown resistance against one or more known radiation treatments. The resistance may be total or partial. The cancer may be both drug-resistant and radiation resistant in some cases, or may be only drug-resistant or only radiation-resistant.

Preferably, the subject is a mammal, for example selected from a human, companion animal, non-domestic livestock or zoo animal. For example, the subject may be selected from a human, dog, cat, cow, pig, sheep, horse, bear, and so on.

According to another aspect of the present invention, there is provided use of a compound or composition as described herein in the manufacture of a medicament for therapy, preferably for the treatment of cancer, for example drug-resistant cancer and/or radiation-resistant cancer. Examples of preferred types of cancer are described elsewhere herein, for example with reference to the methods of the present invention.

According to another aspect of the present invention, there is provided a method for treating a disease, comprising administering to a subject a therapeutically effective amount of a compound or composition as described herein. Preferably, the disease is cancer. Examples of preferred types of cancer are described elsewhere herein, for example with reference to the methods of the present invention. Preferably, the disease is a drug resistant cancer, and/or a radiation-resistant cancer. In this respect, it will be appreciated that a drug resistant cancer is a cancer that has shown resistance against one or more known anti-cancer drugs, for example Temodar®. The resistance shown may be total or partial. In this respect a radiotherapy-resistant cancer is a cancer that has shown resistance against one or more known radiation treatments. The resistance may be total or partial. The cancer may be both drug-resistant and radiation resistant in some cases, or may be only drug-resistant or only radiation-resistant.

As described elsewhere herein, it will be appreciated that reference in the specification to "a compound as described herein" means a compound of any of Formulae I to XXII, or a derivative, homologue, prodrug, solvate, or pharmaceutical salt thereof. Reference to "a compound as described herein" may also mean any of the compounds described within this specification, for example derived from the following Formula or a derivative, homologue, prodrug or pharmaceutical salt thereof:—

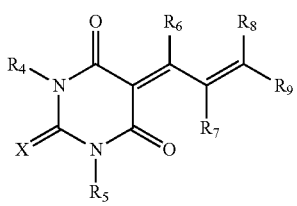

wherein X is selected from O or S;

and wherein $R_4$ and $R_5$ are independently selected from: a hydrogen atom; a substituted or unsubstituted alkyl group having from 1-10 carbon atoms; a substituted or unsubstituted alkenyl group having from 2-10 carbon atoms; a substituted or unsubstituted cycloalkyl group having from 3-9 carbon atoms; a substituted or unsubstituted heterocyclic group having from 3-9 atoms its ring;

$R_6$ and $R_7$ are independently selected from: a hydrogen atom; a substituted or unsubstituted alkyl group having from 1-10 carbon atoms; a substituted or unsubstituted alkenyl group having from 2-10 carbon atoms; a substituted or unsubstituted cycloalkyl group having from 3-9 carbon atoms; a substituted or unsubstituted heterocyclic group having from 3-9 atoms its ring; and a substituted or unsubstituted aryl group;

$R_8$ and $R_9$ are independently selected from a hydrogen atom; a substituted or unsubstituted alkyl group having from 1-10 carbon atoms; a substituted or unsubstituted alkenyl group having from 2-10 carbon atoms; a substituted or unsubstituted cycloalkyl group having from 3-9 carbon atoms; a substituted or unsubstituted heterocyclic group having from 3-9 atoms its ring; and a substituted or unsubstituted aryl group;

provided that when X is O:
when one of $R_8$ and $R_9$ is H and the other is an unsubstituted phenyl group, at least one of $R_4$ and $R_5$ is not H;

and provided that when X is S:
when one of $R_5$ and $R_9$ is H and the other is an unsubstituted phenyl group, at least one of $R_4$ and $R_5$ is not H; and when one of $R_8$ and $R_9$ is H and the other is an unsubstituted furanyl group, $R_4$ and $R_5$ are not H and Et, and $R_4$ and $R_5$ are not H and p-chlorophenyl.

For example, reference to "a compound as described herein" may mean a compound derived from the following Formula or a derivative, homologue, prodrug or pharmaceutical salt thereof:—

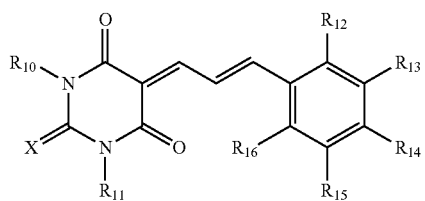

wherein X is O or S, and wherein $R_{10}$ and $R_{11}$ are independently selected from H, Me and Et;

$R_{12}$ to $R_{16}$ are independently selected from —H, —F, —Cl, —Br, —I, -Me, -Et, OH, —OMe, —OEt, $NO_2$, $NH_2$, NHMe, NHEt, $NMe_2$, NMeEt, $NE_{t2}$, and —CN.

Reference to "a compound as described herein" may mean any of the compounds described in Table 2b.

Reference in the specification to "a composition as described herein" means a composition comprising a compound as described herein. Preferably, the composition is a pharmaceutical composition.

Preferably, the composition comprises a therapeutically effective amount of at least one compound as described herein or a physiologically tolerated salt thereof. Preferably, the composition comprises a physiologically tolerated carrier.

Preferably, the compositions of the present invention comprise one or more additional active compounds. Preferably, the one or more additional active compounds are therapeutically active compounds, for example in the form of an additional therapeutic compound for co-delivery with the compositions described herein.

According to another aspect of the present invention, there is provided a compound as described herein for use in reducing tumor size in a mammalian subject, preferably wherein the tumor is a drug-resistant tumor, and/or a radiation-resistant tumor.

According to another aspect of the present invention, there is provided a compound as described herein for use in inducing apoptosis in a tumor cell in a mammalian subject, preferably wherein the tumor cell is a drug-resistant tumor cell, and/or a radiation-resistant tumor cell.

Within this specification aspects have been described in a way which enables a clear and concise specification to be written, but it is intended and will be appreciated that aspects may be variously combined or separated without parting from the invention. For example, it will be appreciated that the preferred features of the methods described herein are equally applicable to the compounds, compositions and uses described herein.

Drug-resistance and radiation-resistance in certain cell lines is clearly shown.

Figure 2A:
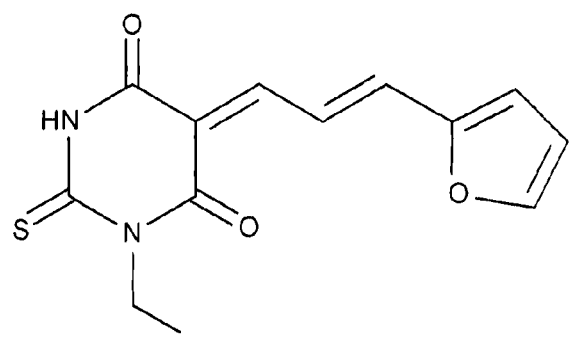
Figure 2B:
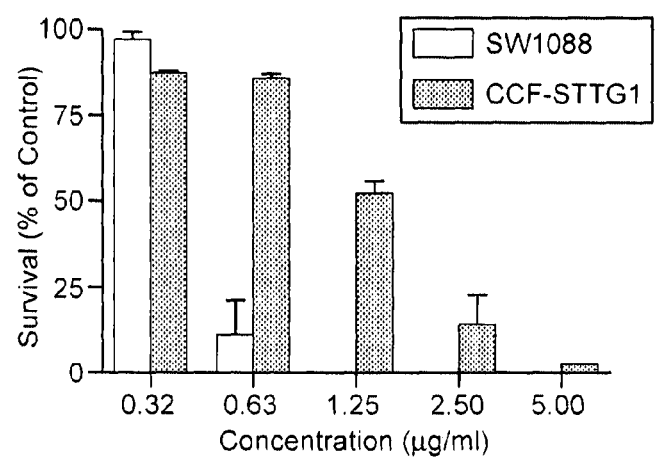
Figure 2C:
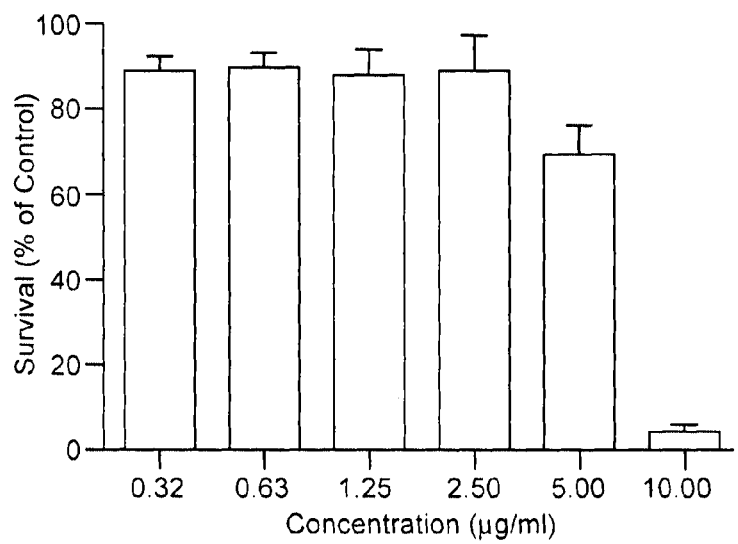
Figure 2D:
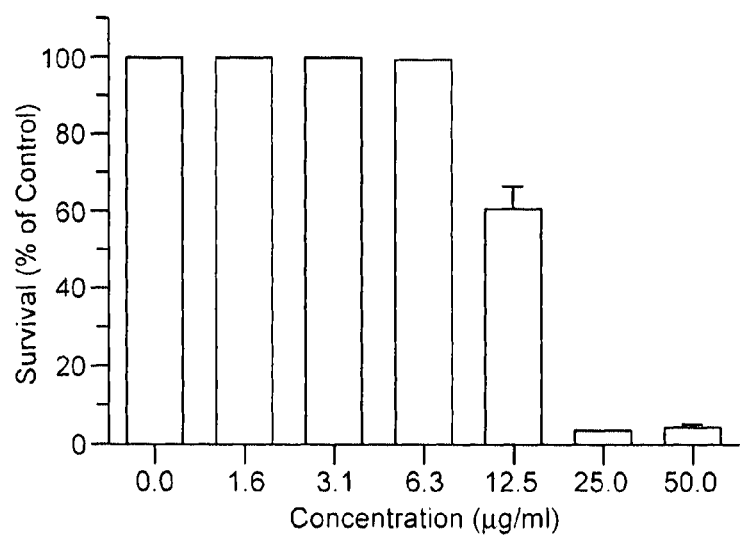

FIGS. 2A-2D show the structure (FIG. 2A) and cytotoxic concentrations of chemotype compound I (CC-I) on human astrocytoma (SW1088 and CCF-STTG1) (FIG. 2B), human astrocyte (FIG. 2C), and bovine retinal endothelial cells (BREC) (FIG. 2D). Experiments described in Example 2.

Figure 3A:
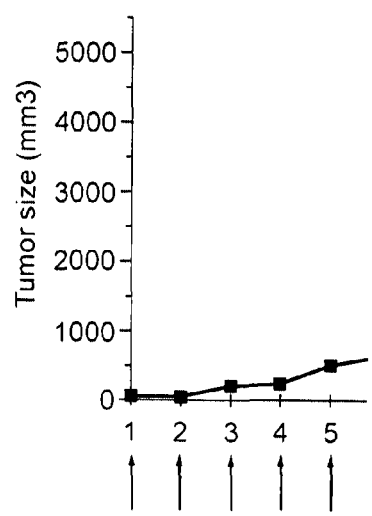
Figure 3B:
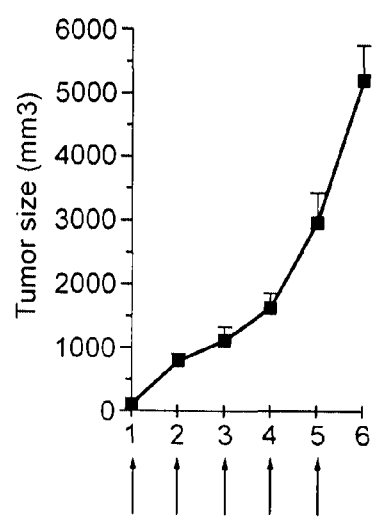

FIGS. 3A and 3B show the effect of CC-I on tumors formed from SW1088 (FIG. 3A) or CCF-STTG1 (FIG. 3B) cells injected subcutaneously into nude mice. Experiments described in Example 3.

FIGS. 4A-D show the effect of CC-I on an intracranial tumor model. (FIG. 4A) MRI analysis. Arrows mark tumor tissue. (FIG. 4B) Survival curves for CC-I treated (filled symbols) and control (open symbols) CCF-STTG1 and U87-MG cell tumors. (FIG. 4C and FIG. 4D) Blood chemistry for liver and kidney toxicity. Blood urea nitrogen (BUN), aspartate aminotransferase (SGOT/AST), alanine aminotransferase (SGPT/ALT). Experiments described in Example 4.

Figure 5:
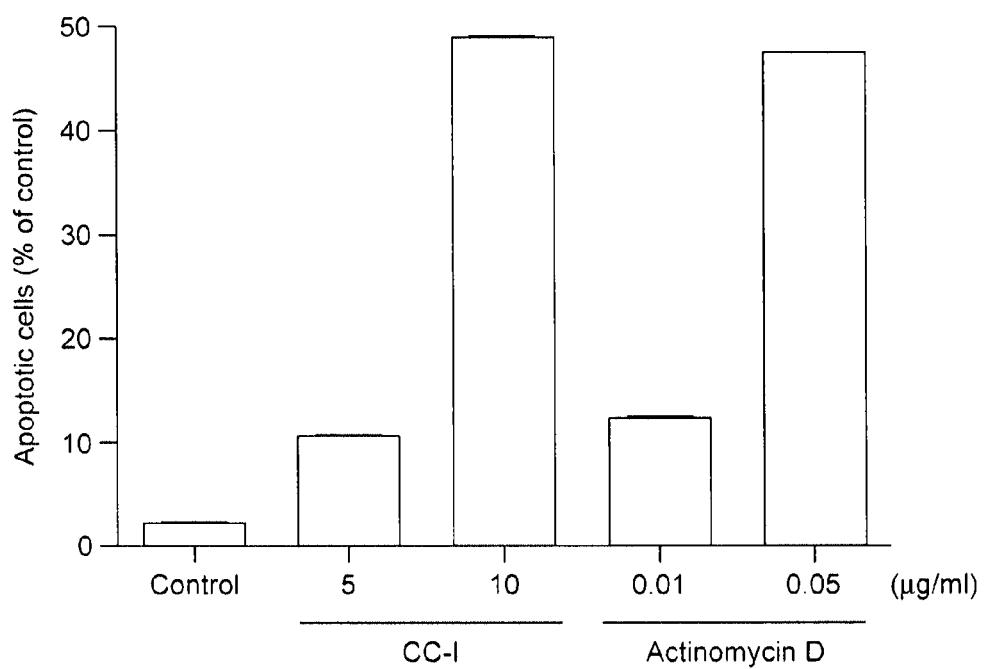

FIG. 5 shows the effect of CC-I and actinomycin D on apoptosis in CCF-STTG1 cells. Experiments described in Example 5.

Figure 6A:
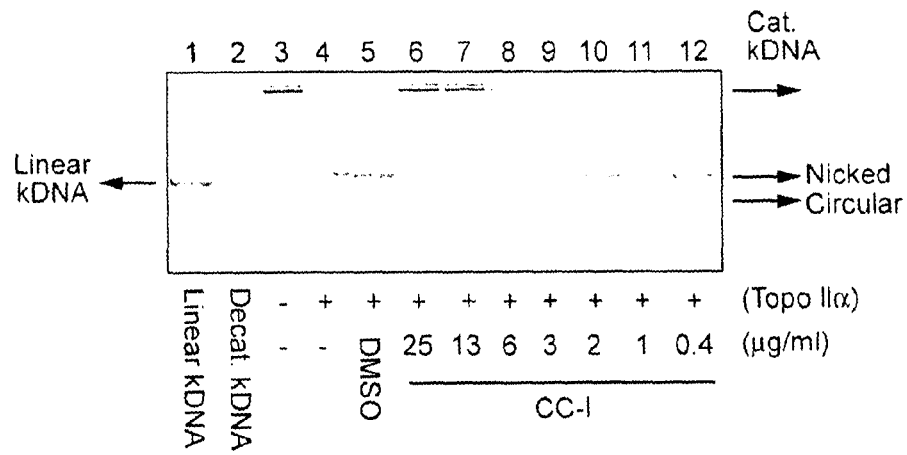
Figure 6B:

FIGS. 6A and 6B show the effects of CC-I on topoisomerase IIα mediated kDNA decatenation. CC-I inhibited human topoisomerase IIα-mediated kDNA decatenation in a concentration dependent manner. Different topological forms exhibited different mobility as indicated. Linear—linear kDNA; Cat.—catenated; Decat. decatenated; Nicked—nicked decatenated kDNA; circular—circular decatenated kDNA; kDNA—kinetoplast DNA. Experiments described in Example 6.

Figure 7A:
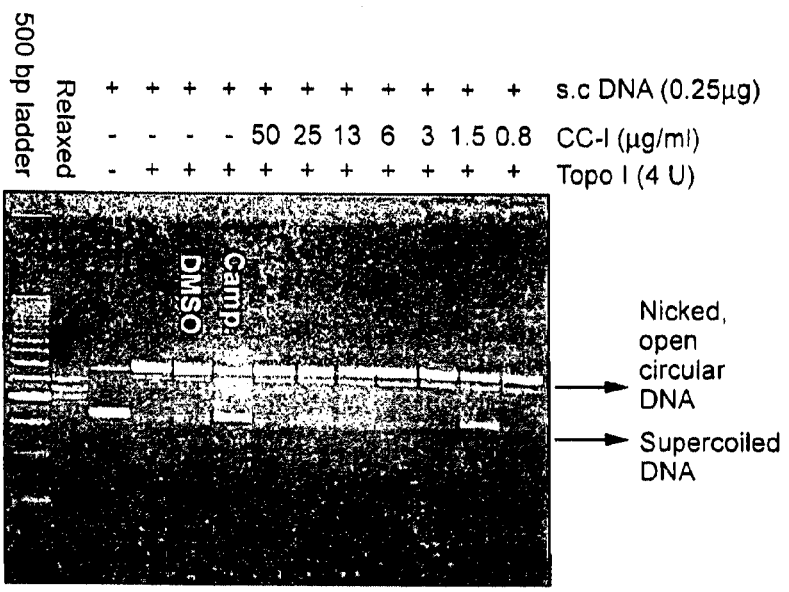
Figure 7B:
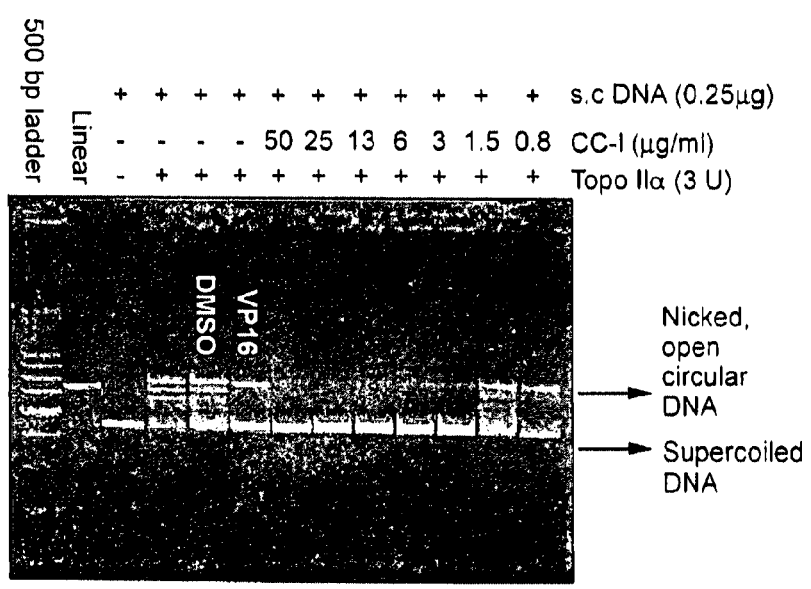

FIGS. 7A and 7B shows the effects of CC-I on topoisomerase I (FIG. 7A) and IIα (FIG. 7B) mediated relaxation of supercoiled DNA.

(FIG. 7A) CC-I did not inhibit human topoisomerase I-mediated relaxation of supercoiled pBR322 DNA plasmid even at the highest concentration tested, in contrast to the positive control, camptothecin (Camp.).

(FIG. 7B) CC-I strongly inhibited topoisomerase IIα-mediated relaxation of supercoiled pHOT1 DNA plasmid. At concentrations greater than 3 μg/ml, CC-1 completely inhibited topoisomerase IIα catalyzed pHOT1 relaxation, as did the positive control, etoposide (VP-16, 1 mM). Different topological forms of DNA exhibited different mobility as indicated. Linear—linear DNA; relaxed—relaxed DNA; s.c.—supercoiled. Experiments described in Example 6.

Figure 8A:
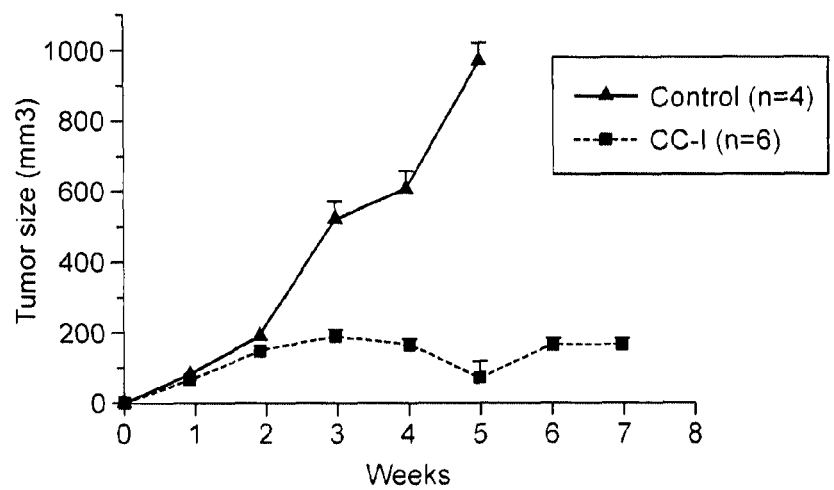
Figure 8B:
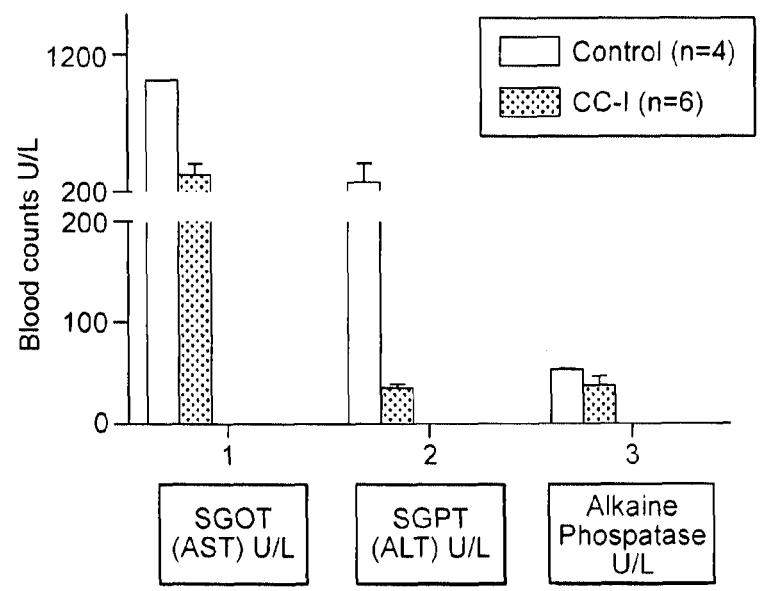
Figure 8C:
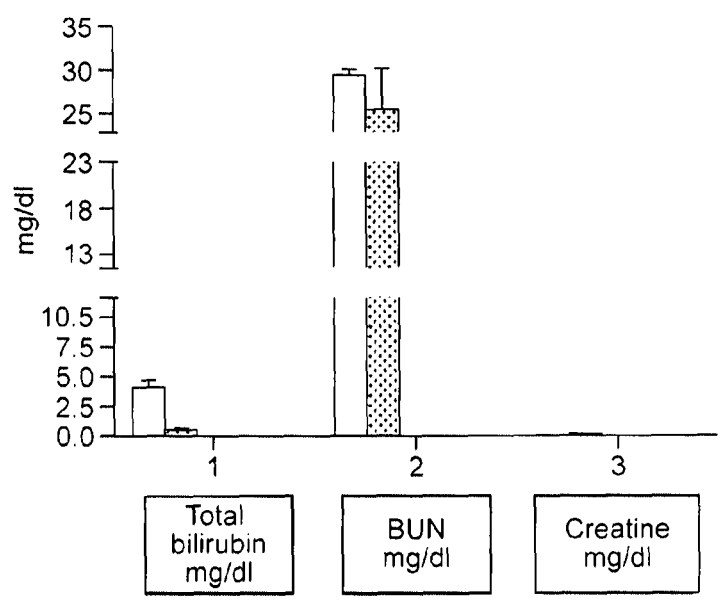

FIGS. 8A-C show the effects of CC-I on SCID mice bearing a subcutaneous tumor from neuroblastoma cells carrying the C282Y HFE mutation.

(FIG. 8A) CC-I completely inhibited tumor growth in tumor-bearing mice compared with the untreated controls.

(FIG. 8B) and (FIG. 8C) Liver and kidney toxicity were not observed in the animals that received CC-I. Experiments described in Example 7.

Figure 9:
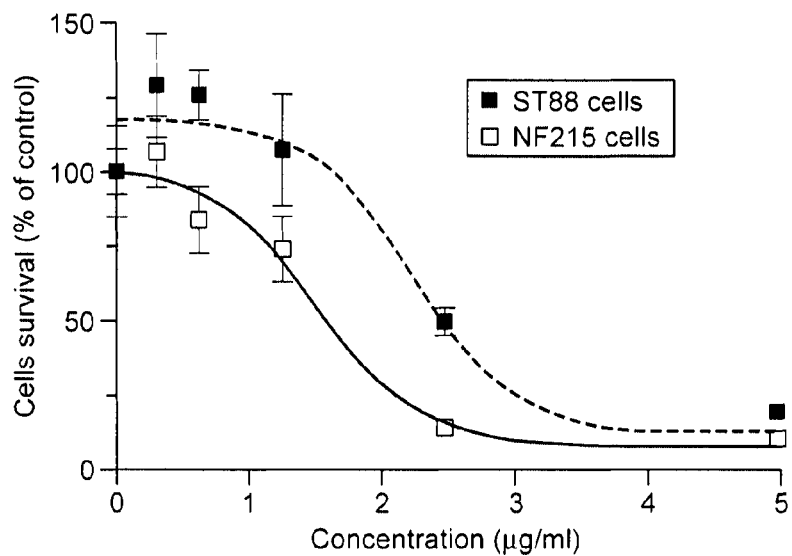

FIG. 9 shows the effect of CC-I on neurofibroma cell lines. The LD50 for ST88 and NF215 neurofibroma cells is 2.1 μg/ml and 1.4 μg/ml, respectively. Experiments described in Example 8.

Figure 10:
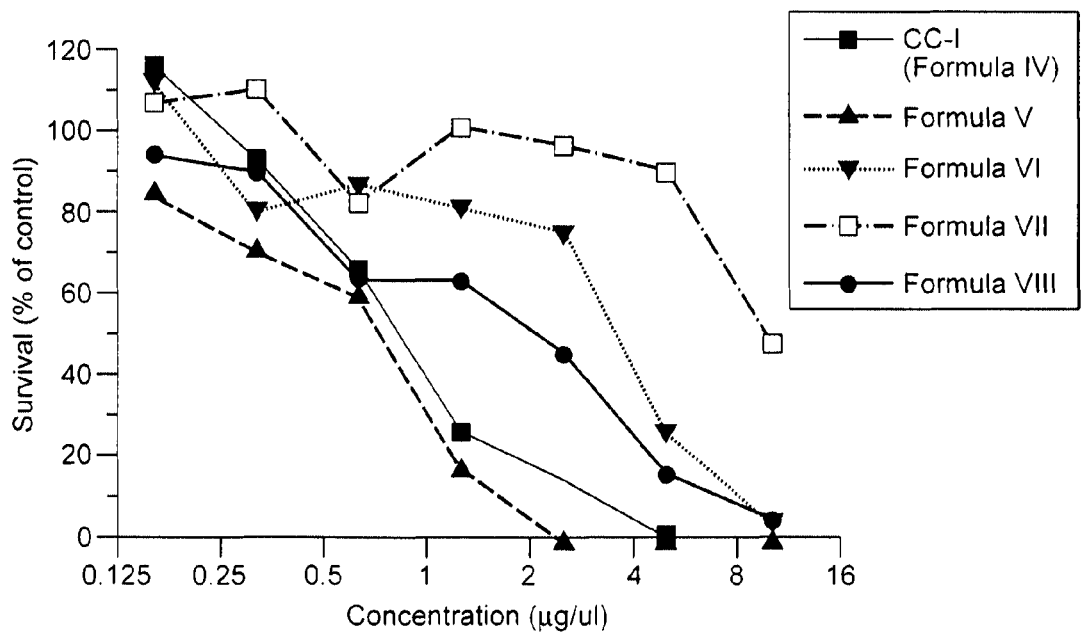

FIG. 10 is a graph showing the effects of CC-I and CC-I derivatives on cell survival in the Temodar® resistant human glioma cell line CCF-STTG1. Experiments described in Example 10.

Figure 11A:
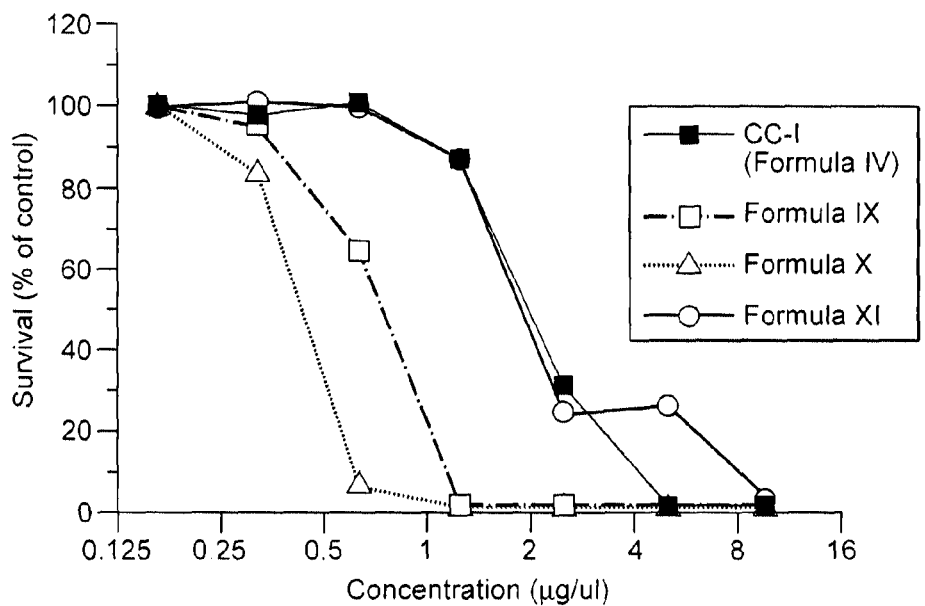
Figure 11B:
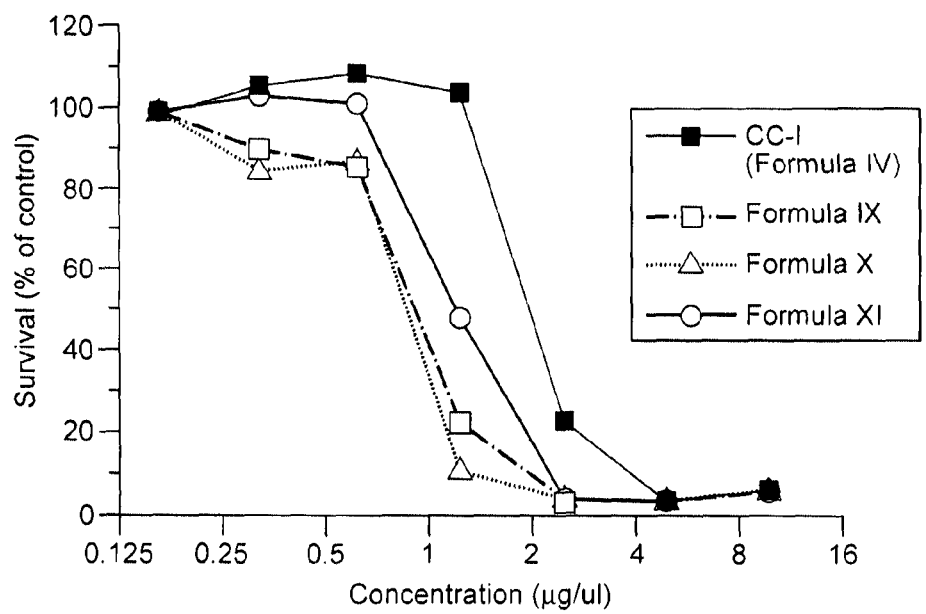

FIGS. 11A and 11B are graphs showing the effects of CC-I and CC-I derivatives on cell survival in cells of the U87-MG (FIG. 11A) and CCF-STTG1 (FIG. 11B) glioma cell lines. Experiments described in Example 10.

Figure 12A:
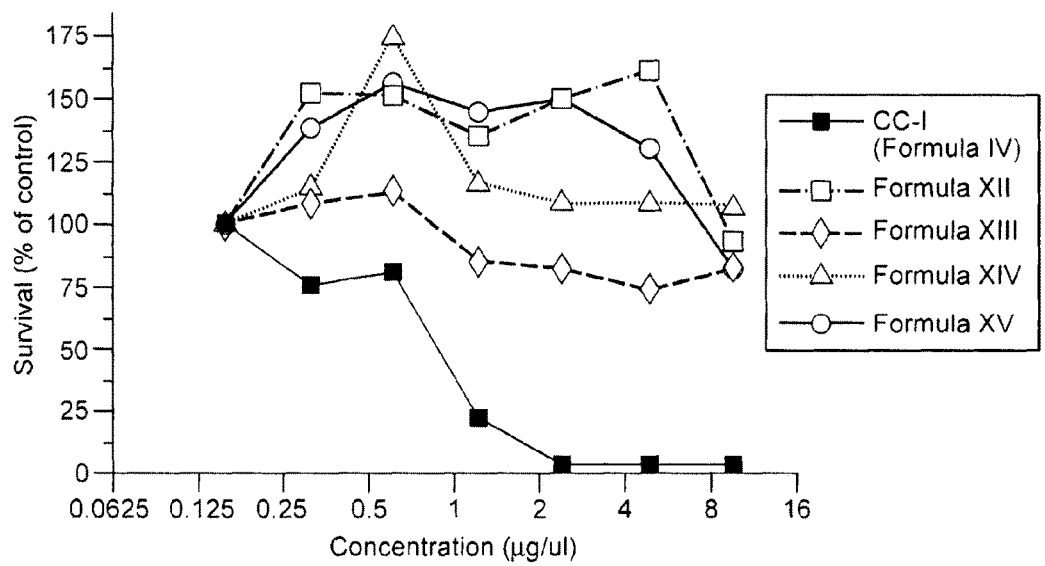
Figure 12B:
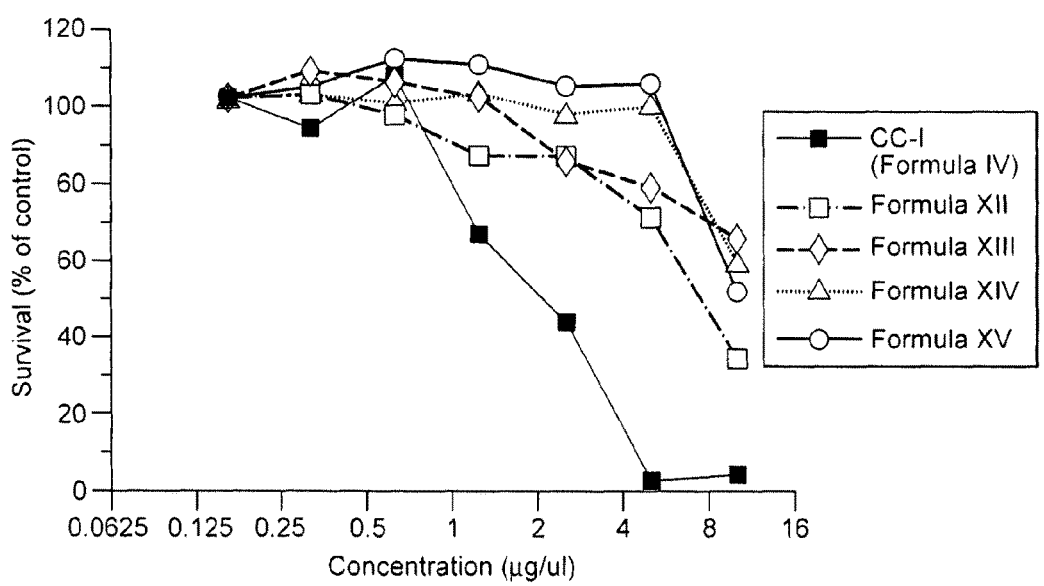

FIGS. 12A and 12B are graphs showing the effects of CC-I derivatives on cell survival in cells of the U87-MG (FIG. 12A) and CCF-STTG1 (FIG. 12B) glioma cell lines. Experiments described in Example 10.

Figure 13A:
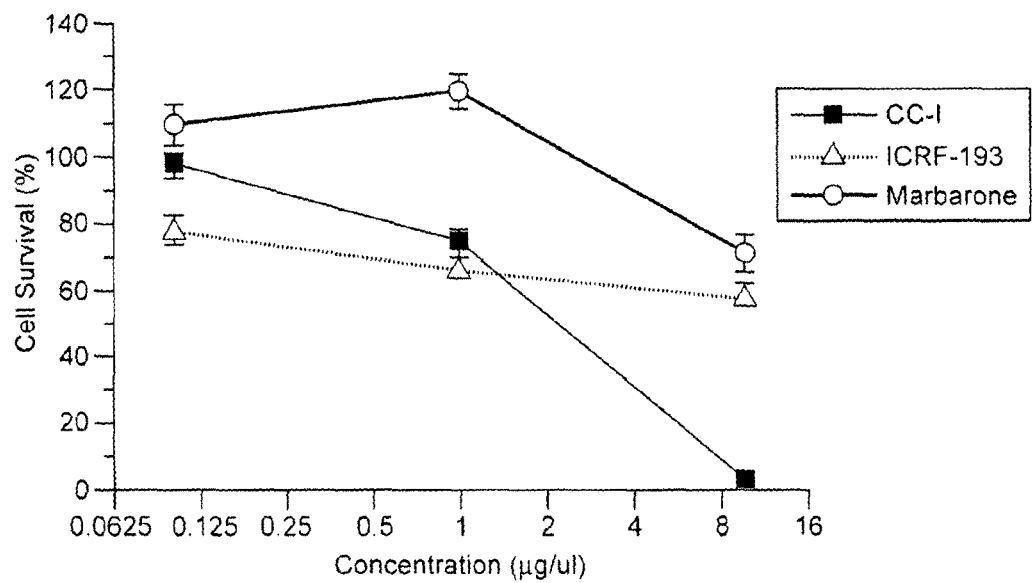
Figure 13B:
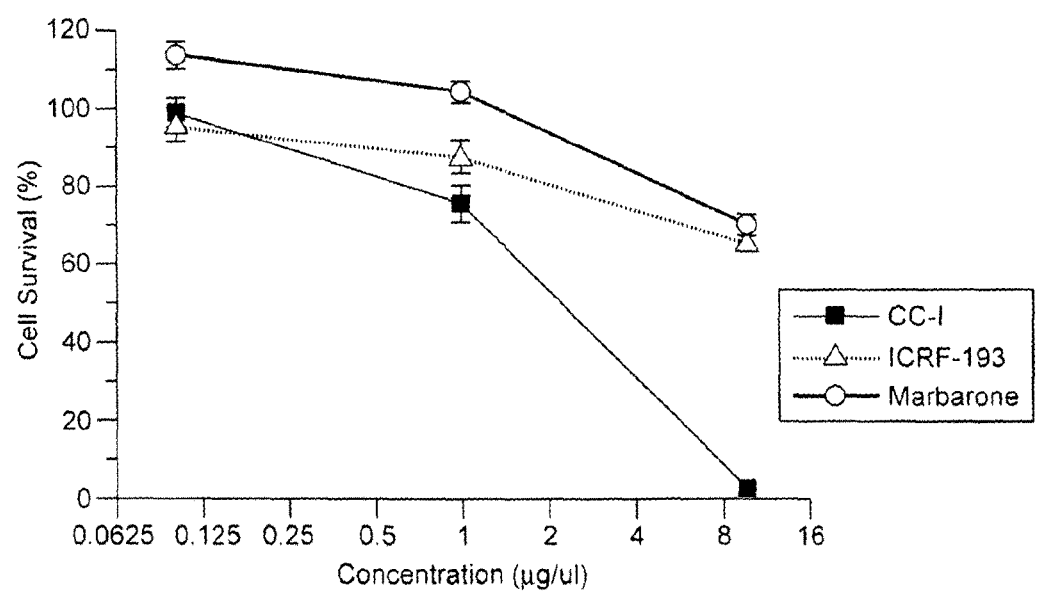

FIGS. 13A and 13B are graphs showing the effects of CC-I, Merbarone, and ICRF-193 on glioma cell lines, U87-MG (FIG. 13A) and CCF-STTG1 (FIG. 13B). Experiments described in Example 11.

Figure 14:
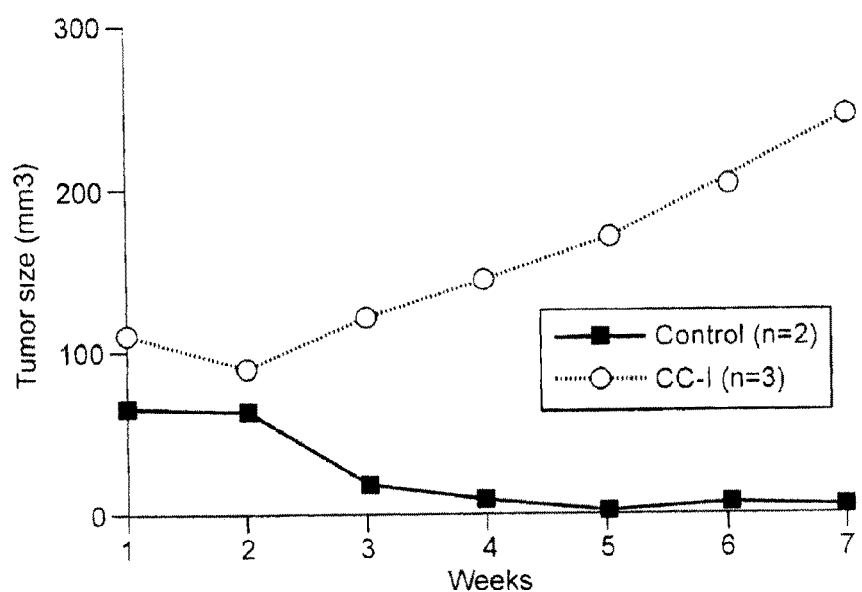

FIG. 14 is a graph showing the anti-tumor effect of CC-I in A549 lung cancer subcutaneous nude mouse tumor model. Experiments described in Example 12.

DETAILED DESCRIPTION OF THE INVENTION

Screening analyses have elicited compounds that can improve methods of cancer therapy generally, and, in particular, the treatment of brain tumors, neurofibromas and metastatic brain cancers. Despite the position of Temodar® as the standard chemotherapeutic treatment for brain tumors, more than half of all brain tumors are resistant to Temodar® chemotherapy (14, 15).

Therefore, a screen for compounds that are cytotoxic to Temodar®-resistant cells was performed. A lead compound, Chemotype Compound I, (CC-I), was toxic to both Temodar®-resistant and Temodar®-sensitive cell lines as described in Example 1 and shown in FIG. 2. Accordingly, CC-I, and derivatives and homologues thereof; (collectively, "CC-I compounds" herein) could be useful as therapies, in particular for treating cancers, especially as an alternative or supplement to Temodar® to provide more effective cancer chemotherapy. CC-I and its derivatives may be particularly useful for brain tumors and ovarian tumors, and for drug-resistant tumors and/or radiation-resistant tumors.

As illustrated by the Examples below, CC-I compounds cross the blood-brain barrier and prevent tumor growth in drug-resistant and radiation-resistant, as well as sensitive, tumor cells. CC-I was not toxic to the liver or kidney in in vivo studies, and was not toxic to normal cells at dosages that were toxic to tumor cells in vitro. CC-I was effective against glioma, astrocytoma, neuroblastoma, ovarian cancer cells, as shown in Table 1. In addition, CC-I was cytotoxic to neurofibroma cancer cells, which give rise to peripheral nerve tumors, for which there is no known chemotherapeutic treatment. In later tests it has also been found that CC-I has a pXC50 of 4.5 when tested on A549 cells.

TABLE 1

| IC50 (μM) | SW1088 | U87-MG | U251 | CCF-STTG1 | Human Astrocyte (Normal cells) | BREC | ST88 |
|---|---|---|---|---|---|---|---|
| Temodar ® | 29.5 | 13.6 | 47.2 | 305.9 | ND | ND | ND |
| CC-I (Formula IV) | 1.7 | 3.9 | 3.8 | 4.3 | 16.4 | 46.9 | 7.5 |
| Formula V | 1.2 | 1.8 | 2.5 | 3.0 | ND | ND | ND |

| IC50 (μM) | NF215 | MCF10A | MCF7 | SVGp12 | OVCAR-3 | WT/SH-SY5Y | C282Y/SH-SY5Y |
|---|---|---|---|---|---|---|---|
| Temodar ® | ND | ND | ND | ND | ND | 102.8 | 92.02 |
| CC-I (Formula IV) | 5.1 | 6.5 | 15.6 | 4.2 | 3.5 | 3.3 | 1.8 |
| Formula V | ND | 1.7 | 3.2 | 1.6 | 4.3 | ND | ND |

SW1088, U87-MG, U251, CCF-STTG1; human astrocytoma or glioblastoma cell lines
BREC; bovine retinal endothelial cell
ST88, NF215: human neurofibroma cell lines
MCF 10A; immortalized, non-transformed epithelial cell line derived from human fibrocystic mammary tissue
MCF7; human breast adenocarcinoma cell line
SVG p12; SV40 transformed human astrocyte cell line
OVCAR-3; human ovarian carcinoma cell line
WT/SH-SY5Y; wild type HFE gene stably transfected human neuroblastoma SH-SY5Y cell line
C282Y/SH-SY5Y; C282Y HFE polymorphism gene stably transfected human neuroblastoma SH-SY5Y cell line CC-I compounds are topoisomerase IIα inhibitors, as described in Example 6, and can induce apoptosis in tumor cells, as described in Example 5. Topoisomerase IIα expression is involved in the progression of ovarian cancer, renal medullary carcinoma, gastric cancer and breast cancer (33-36), and is elevated in oligoastrocytomas and glioblastoma (37, 38). Topoisomerase IIα is also involved in relapse in acute lymphocytic leukemia (39) and influences drug response in colorectal cancer (40). The gene encoding topoisomerase IIα is a target for a number of anticancer agents, and accordingly, topoisomerase IIα inhibitors or poisons, such as doxorubicin, are used in the treatment of cancer as described above. However, as with Temodar®, many tumor cells are resistant to Doxorubicin (41-43).

In one aspect the invention pertains to a method for reducing tumor size comprising administering to the subject a therapeutically effective amount of a CC-I compound. In another aspect, the invention pertains to a method for inducing apoptosis in a tumor cell comprising administering to the tumor cell a therapeutically effective amount of a CC-I compound. These methods are effective for treating drug-resistant cancer, and radiation-resistant cancer. The administered CC-I compound may have or be a derivative of one of the structures of Formulae I-XXII, as described below:

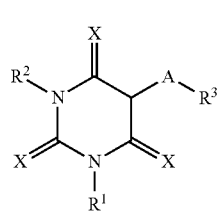

(I)

wherein:
X is O or S;
A is an alkenylidene;
$R^1$ and $R^2$ are independently selected from the group consisting of (i) an alkyl containing from 1 to 10 carbon atoms, which may be linear or branched, (ii) an alkenyl containing from 2 to 10 carbon atoms, which may be linear or branched; and (iii) a hydrogen; and
$R^3$ is a phenyl or heteroaryl, which may be linear or branched, and optionally substituted with a heteroalkyl, which may be linear or branched,
or a derivative, homologue, prodrug or pharmaceutical salt thereof.

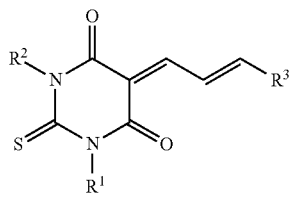

(II)

wherein:
$R^1$ and $R^2$ are independently selected from the group consisting of (i) an alkyl containing from 1 to 10 carbon atoms, which may be linear or branched, (ii) an alkenyl containing from 2 to 10 carbon atoms, which may be linear or branched; and (iii) a hydrogen; and $R^3$ is a phenyl or heteroaryl, which may be linear or branched, and optionally substituted with a heteroalkyl, which may be linear or branched,
or a derivative, homologue, prodrug or pharmaceutical salt thereof.

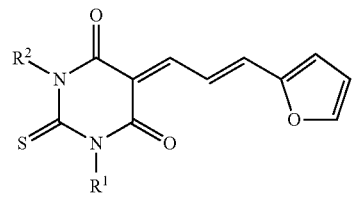

(III)

wherein:
$R^1$ and $R^2$ are independently selected from the group consisting of (i) an alkyl containing from 1 to 10 carbon atoms, which may be linear or branched, (ii) an alkenyl containing from 2 to 10 carbon atoms, which may be linear or branched; and (iii) a hydrogen,
or a derivative, homologue, prodrug or pharmaceutical salt thereof.

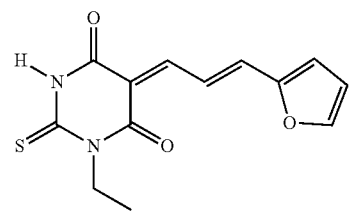

(IV)

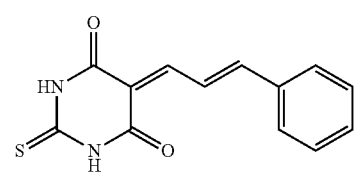

(V)

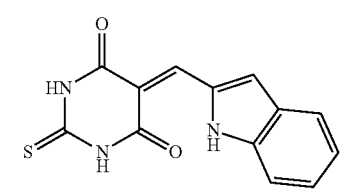

(VI)

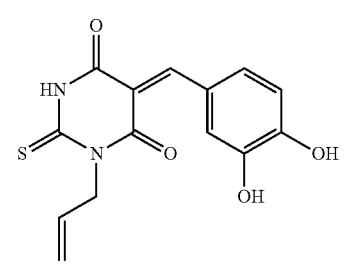

(VII)

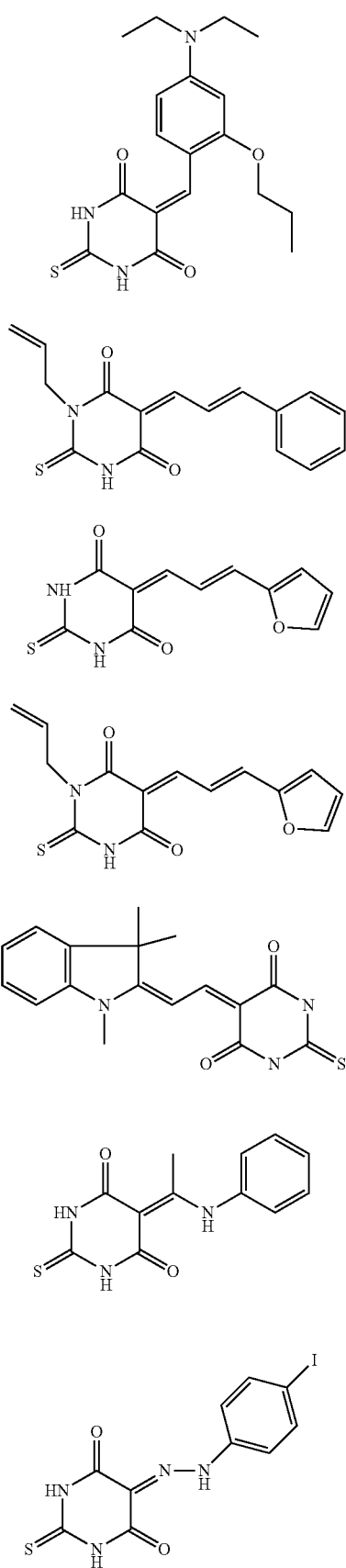
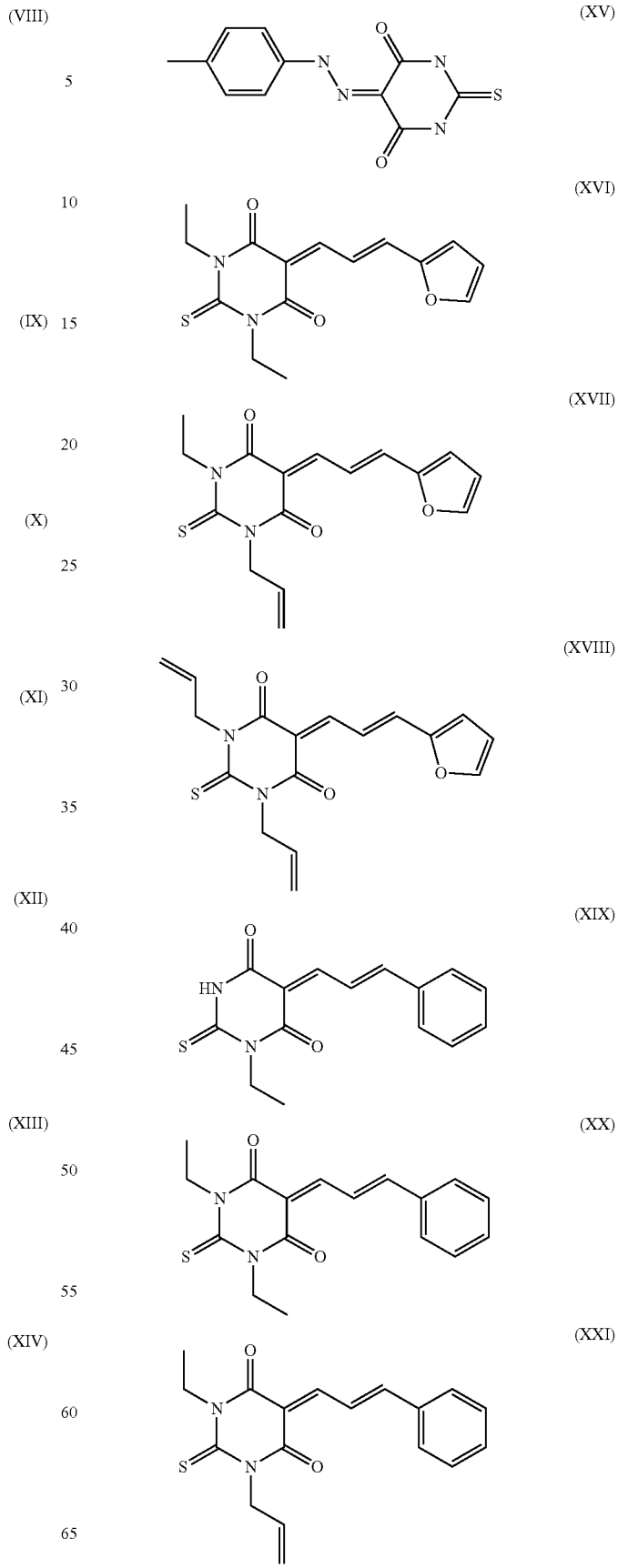

-continued

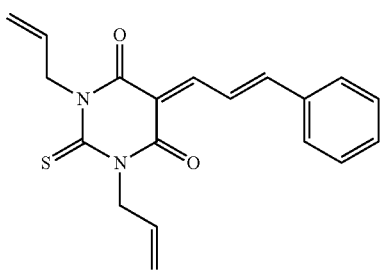

(XXII)

Definitions

The following definitions apply herein.

The term "about" means plus or minus 20%, more preferably plus or minus 10%, even more preferably plus or minus 5%, most preferably plus or minus 2%.

The term "therapeutically effective amount" means the amount of a compound or composition which is required to reduce the severity of and/or ameliorate at least one condition or symptom which results from the disease in question.

The term "cancer" includes malignancies characterized by deregulated or uncontrolled cell growth, for instance carcinomas, sarcomas, leukemias, and lymphomas. The term "cancer" includes primary malignant tumors, e.g., those whose cells have not migrated to sites in the subject's body other than the site of the original tumor, and secondary malignant tumors, e.g., those arising from metastasis, the migration of tumor cells to secondary sites that are different from the site of the original tumor.

The terms "effective amount" and "therapeutically effective amount" refer to an amount of a drug or compound effective to treat disease in the treated subject. Where the disease is cancer, the effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival, result in an objective response (including a partial response or complete response), increase overall survival time, and/or improve one or more symptoms of cancer.

The term "subject" refers to an animal, preferably a mammal and in particular a human. In a particular aspect, the subject is suffering from a disease, for example, cancer.

The term "alkenylidene" refers to a hydrocarbon group having one or more double bonds. In certain aspects, an alkenylidene group has 1 to 6 carbon atoms. In other aspects, an alkenylidene group has 1, 2, 3, 4 or 5 carbon atoms. According to one aspect, an alkenylidene has one double bond. According to another aspect, an alkenylidene has two double bonds. Exemplary alkenylidene groups include =CH—CH=CH—, =CH—CH$_2$—, =C—, =C=CH—CH$_2$-, =CH—CH$_2$—CH=CH—, =CH—CH=CH—CH=CH—. In a preferred aspect, the alkenylidene group is a conjugated alkenylidene group. It will be appreciated that in the formulae presented, the alkenylidene group is attached to the core 6-membered ring structure by a double bond.

The term "heteroaryl" means an aromatic monocyclic or bicyclic group containing 5- or 6-membered rings containing up to 4 heteroatoms selected from N, O and S. Examples of heteroaryl groups include furanyl, pyrrolyl, thiophenyl, 1,3-oxazolyl, 1,2-oxazolyl, 1,3-thiazolyl, 1,2-thiazolyl, indole, indoline and benzofuran. The heteroaryl group may be attached to the remainder of the molecule through a heteroatom.

The term "heteroalkyl" refers to an alkyl or alkenyl group containing 1 to 6 carbon atoms in which one or more carbon atoms have been replaced with an oxygen, nitrogen or sulphur atom. The heteroalkyl group may be linear or branched. Examples of heteroalkyl groups include methyl, carboxylic acid and hydroxyl groups.

The active compounds disclosed herein can, as noted above, can be prepared in the form of their pharmaceutically acceptable salts. Pharmaceutically acceptable salts are salts that retain the desired biological activity of the parent compound and do not impart undesired toxicological effects. Examples of pharmaceutically acceptable salts are discussed in Berge et al., 1977, "Pharmaceutically Acceptable Salts," *J. Pharm. Sci., Vol.* 66, pp. 1-19 (44).

The active compounds disclosed may also be prepared in the form of their solvates. The term "solvate" is used herein in the conventional sense to refer to a complex of solute (e.g., active compound, salt of active compound) and solvent. If the solvent is water, the solvate may be conveniently referred to as a hydrate, for example, a hemihydrate, monohydrate, dihydrate, trihydrate, tetrahydrate, and the like.

The invention further extends to prodrugs of the compounds described herein. The term "prodrug" refers to a compound that is biologically inactive, but is metabolized to produce an active therapeutic drug.

The term "derivatives" refers to molecules derived from the compounds described herein. Such derivatives may, for example, be synthetically altered derivatives of these compounds.

The term "homologues" refers to molecules having substantial structural similarities to the compounds described herein.

Within this specification, the term "treatment" means treatment of an existing disease and/or prophylactic treatment in order to prevent incidence of a disease. As such, the methods of the invention can be used for the treatment, prevention, inhibition of progression or delay in the onset of disease.

A second embodiment of the invention concerns the treatment of cancer generally, by employing a group of compounds newly discovered to have beneficial anti-cancer properties. This embodiment of the invention provides a compound for use in treating cancer, which compound has the following formula:

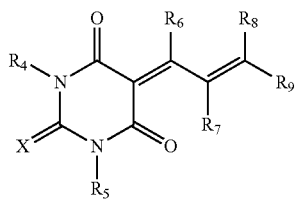

wherein X is selected from O or S;
and wherein $R_4$ and $R_5$ are independently selected from:
  a hydrogen atom; a substituted or unsubstituted alkyl group having from 1-10 carbon atoms; a substituted or unsubstituted alkenyl group having from 2-10 carbon atoms; a substituted or unsubstituted cycloalkyl group having from 3-9 carbon atoms; a substituted or unsubstituted heterocyclic group having from 3-9 atoms its ring; a substituted or unsubstituted phenyl group;

$R_6$ and $R_7$ are independently selected from: a hydrogen atom; a substituted or unsubstituted alkyl group having from 1-10 carbon atoms; a substituted or unsubstituted alkenyl group having from 2-10 carbon atoms; a substituted or unsubstituted cycloalkyl group having from 3-9 carbon atoms; a substituted or unsubstituted heterocyclic group having from 3-9 atoms its ring; and a substituted or unsubstituted aryl group;

$R_8$ and $R_9$ are independently selected from a hydrogen atom; a substituted or unsubstituted alkyl group having from 1-10 carbon atoms; a substituted or unsubstituted alkenyl group having from 2-10 carbon atoms; a substituted or unsubstituted cycloalkyl group having from 3-9 carbon atoms; a substituted or unsubstituted heterocyclic group having from 3-9 atoms its ring; and a substituted or unsubstituted aryl group;

provided that when X is O:
when one of $R_8$ and $R_9$ is H and the other is an unsubstituted phenyl group, at least one of $R_4$ and $R_5$ is not H;

and provided that when X is S:
when one of $R_1$ and $R_9$ is H and the other is an unsubstituted phenyl group, at least one of $R_4$ and $R_5$ is not H; and when one of $R_8$ and $R_9$ is H and the other is an unsubstituted furanyl group, $R_4$ and $R_5$ are not H and Et, and $R_4$ and $R_5$ are not H and p-chlorophenyl, or a derivative, homologue, prodrug, solvate, or pharmaceutical salt thereof.

In this second embodiment it is preferred that X is O, although X may also be S. In some aspects X may also be Se.

In any of the formulae in the second embodiment, the substituted or unsubstituted alkyl group and the substituted or unsubstituted alkenyl group are preferably unsubstituted. They may be straight or branched groups, but are preferably straight (unbranched) groups. These groups are preferably lower alkyl or lower alkenyl groups having from 1-6 carbon atoms, and typically having 1, 2, 3, 4 or 5 carbon atoms (typically 2, 3, 4 or 5 carbon atoms for alkenyl groups). Typically when an alkene group is present, the group has only a single unsaturated bond. Most preferred groups include methyl, ethyl, propyl and ethenyl groups.

The substituted or unsubstituted cycloalkyl group referred to in any of the formulae in the second embodiment is preferably unsubstituted. The ring system may typically comprise 3, 4, 5, 6, 7, 8, or 9 atoms. Thus the ring may preferably comprise from 5-9 atoms, from 5-7 atoms, or from 5-6 atoms. The ring system may comprise fused rings (e.g. bicyclic ring systems), or may be a single ring. Cyclohexyl groups are preferred. The ring system may contain unsaturated carbon to carbon bonds, typically one or two such unsaturated bonds, which may be conjugated or unconjugated.

The substituted or unsubstituted heterocyclic group referred to in any of the formulae in the second embodiment may be an aromatic or non-aromatic heterocyclic group. The ring system may typically comprise 3, 4, 5, 6, 7, 8, or 9 atoms. Thus the ring may preferably comprise from 5-9 atoms, from 5-7 atoms, or from 5-6 atoms. The ring system may comprise fused rings (e.g. bicyclic ring systems), such as a 5-membered ring fused to a 6-membered ring, or may be a single ring.

The substituted or unsubstituted heterocyclic group may be an aromatic heterocyclic group. The aromatic heterocyclic group is typically an aromatic monocyclic or bicyclic group containing 5- or 6-membered rings containing up to 4 heteroatoms selected from N, O and S. Examples of aromatic heterocyclic groups include furanyl, pyrrolyl, thiophenyl, 1,3-oxazolyl, 1,2-oxazolyl, 1,3-thiazolyl, 1,2-thiazolyl, indole, indoline and benzofuran. The aromatic heterocyclic group may be attached to the remainder of the molecule through a heteroatom.

Alternatively, the substituted or unsubstituted heterocyclic group may be an aliphatic heterocycle such as a monocyclic or bicyclic aliphatic heterocyclic group containing 5- or 6-membered rings containing up to 4 heteroatoms selected from N, O and S. Examples of aliphatic heterocycles include, but are not limited to, tetrahydropyran, dihydropyran, pyran, pyrrolidine, pyrroline, piperidine, piperazine and morpholine. The aliphatic heterocyclic group may be attached to the remainder of the molecule through a heteroatom.

In the case where $R_4$ and/or $R_5$ is a heterocyclic group, although the group may have from 3-9 atoms in the ring structure, from 3-6 atoms is preferred, since the substituents on the nitrogen atoms are preferably less sterically hindering than at other positions in the compounds.

The substituted or unsubstituted aryl group referred to in any of the formulae in the second embodiment may be any non-heterocyclic aromatic group, but is typically a substituted or unsubstituted phenyl group. Other exemplary groups may include naphthalene, anthracene or bi-phenyl groups.

The compounds used in the second embodiment represent a group of compounds similar to those employed in the first embodiment, but which are dienes of barbiturate or thiobarbiturates derivatives. These dienes have been found to be particularly active in treating cancer (see Examples 13 et seq.). For best activity, it is preferred that neither of the two alkenes of the diene system are part of a ring system. Accordingly each of $R_6$, $R_7$, $R_8$ and $R_9$ should preferably not together form a ring containing one of the alkenes of the diene system. However, in some aspects such ring systems are possible, particularly if they are not aromatic. In these cases, typically $R_7$ may form a ring with $R_9$ (or $R_8$), such that the second alkene of the diene system is constrained in a ring system. In these cases it is preferred that this ring system is a substituted or unsubstituted six membered ring. This ring system may be a six-membered carbon ring (such as a cyclohexene ring), or a six-membered ring with 5 carbons and one oxygen atom in the ring, or a six-membered ring with 5 carbons and one nitrogen atom in the ring.

In the above compounds of the second embodiment typically at least one of $R_4$ and $R_5$ is H, or is a methyl (Me) group or an ethyl (Et) group. It is preferred that at least one of $R_4$ and $R_5$ is not sterically hindering, as steric hindrance may in some cases impede activity. However, a single group of some size may not be an issue, and tetrahydropyran or cyclohexyl groups may be allowable, when the other group is a small group, such as H. In this context sterically hindering means any groups having more than 7, preferably 6, non-hydrogen atoms.

In the above compounds of the second embodiment typically $R_6$ is H and/or $R_7$ is H, and preferably both $R_6$ and $R_7$ are H. Other substituents are possible, but do not greatly affect activity. Therefore more simple substitution patterns (e.g. H or lower ($C_1$-$C_6$) alkyl) at these groups are preferred.

In the above compounds of the second embodiment typically at least one of $R_8$ and $R_9$ is H. Typically it is also preferred that at least one of $R_8$ and $R_9$ is a substituted or unsubstituted phenyl group, or a substituted or unsubstituted furanyl group, or a substituted or unsubstituted pyridinyl group, or a substituted or unsubstituted indolyl group. Other substituents may also be present, but groups that may conjugate with the diene system are preferred, and especially aromatic groups.

In the compounds of the first and second embodiments, the substituents mentioned above are not especially limited, except to the extent that they comply with the above definitions and provided that they do not hinder activity. Thus in all of the embodiments mentioned in connection with this invention, both above and in the following, the term 'substituent' is not especially limited and may be any functional group or any atom, especially any functional group or atom common in organic chemistry. Thus, substituent may have any of the following meanings. The substituent may comprise any organic group and/or one or more atoms from any of groups IIIA, IVA, VA, VIA or VIIA of the Periodic Table, such as a B, Si, N, P, O, or S atom (e.g. OH, OR, $NH_2$, NHR, $NR_2$, SH, SR, $SO_3H$, $PO_4H_2$ etc.) or a halogen atom (e.g. F, Cl, Br or I) where R is a lower hydrocarbon (1-6 C atoms) or a higher hydrocarbon (7 C atoms or more, e.g. 7-40 C atoms).

When the substituent comprises an organic group, the organic group preferably comprises a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups. When the hydrocarbon comprises a cyclic group it may comprise an aromatic ring, an aliphatic ring, a heterocyclic group, and/or fused ring derivatives of these groups. The cyclic group may thus comprise a benzene, naphthalene, anthracene, indene, fluorene, pyridine, quinoline, thiophene, benzothiophene, furan, benzofuran, pyrrole, indole, imidazole, thiazole, and/or an oxazole group, as well as regioisomers of the above groups.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The lower hydrocarbon group may be a methyl, ethyl, propyl, butyl, pentyl or hexyl group or regioisomers of these, such as isopropyl, isobutyl, tert-butyl, etc. The number of atoms in the ring of the cyclic group is not especially limited, but preferably the ring of the cyclic group comprises from 3-10 atoms, such as 3, 4, 5, 6 or 7 atoms.

The groups comprising heteroatoms described above, as well as any of the other groups defined above, may comprise one or more heteroatoms from any of groups IIIA, IVA, VA, VIA or VIIA of the Periodic Table, such as a B, Si, N, P, O, or S atom or a halogen atom (e.g. F, Cl, Br or I). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, and phosphate groups etc. The substituent may also comprise derivatives of these groups, such as carboxylic acid anhydrides and carboxylic acid halides.

In addition, any substituent may comprise a combination of two or more of the substituents and/or functional groups defined above.

Typically in the most preferred embodiments, the substituents on substituted groups are independently selected from: a halogen group, preferably —F, —Cl, —Br or —I; a lower alkyl group having from 1-6 carbon atoms, such as a methyl (Me), ethyl (Et), propyl (Pr) or butyl (Bu) group; a primary, secondary or tertiary amine group, such as an —$NH_2$ group an —NHMe group and an —$NMe_2$ group; an $NO_2$ group, an OH group, an alkoxy group having from 1-6 carbon atoms, such as an —OMe, —OEt, —OPr, and —OBu group, a —CN group, a tetrahydropyran group and a cyclohexyl group.

In preferred aspects of the second embodiment, the compound for use in the invention has the following formula:

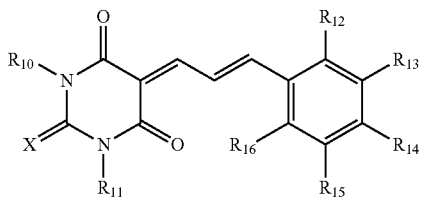

wherein X is O or S, and wherein $R_{10}$ and $R_{11}$ are independently selected from H, Me and Et; $R_{12}$ to $R_{16}$ are independently selected from —H, —F, —Cl, —Br, —I, -Me, -Et, —OH, —OMe, —OEt, —$NO_2$, —$NH_2$, —NHMe, —NHEt, —$NMe_2$, —NMeEt, —$NEt_2$, and —CN.

In this aspect of the second embodiment, typically, X is O. Typically only 1 or 2 of $R_{12}$ to $R_{16}$ are not H, that is to say typically the phenyl group is mono- or di-substituted. In preferred aspects, $R_{12}$-$R_{16}$ are independently selected from —H, —F, —Cl, -Me, -Et, —OMe, —OEt, —$NO_2$, —$NMe_2$, —$NEt_2$, and —CN.

Typically the compound for use in the invention is one of the following compounds:

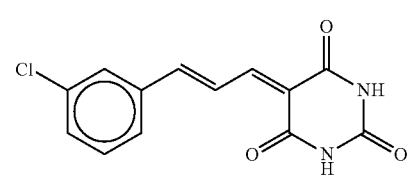
DDD00175302

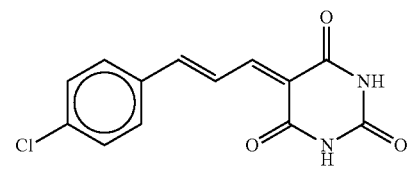
DDD00175286

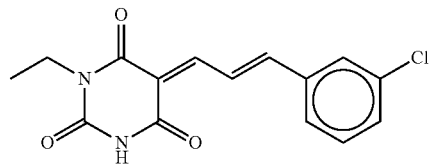
DDD00175297

31
-continued
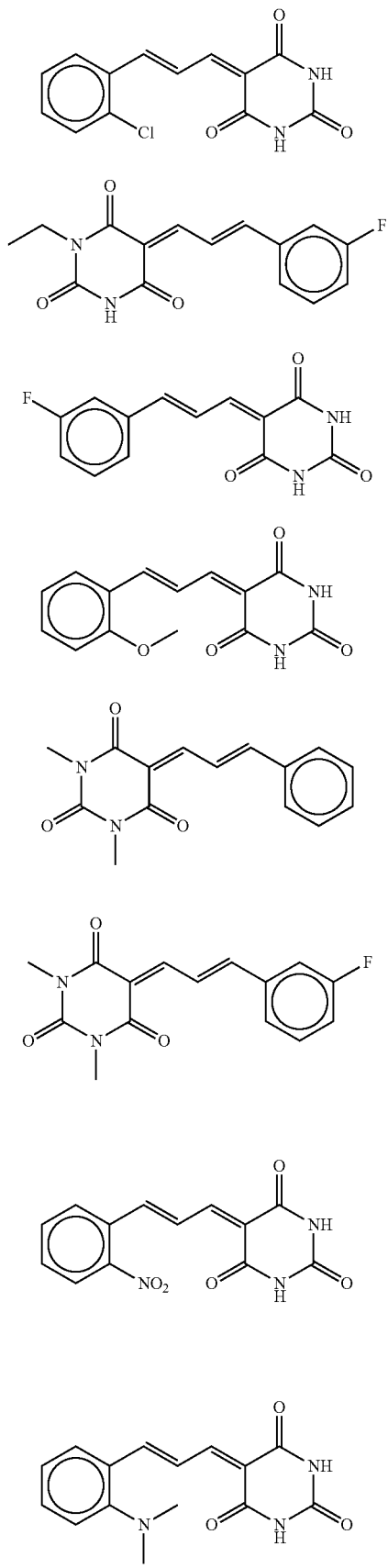
32
-continued
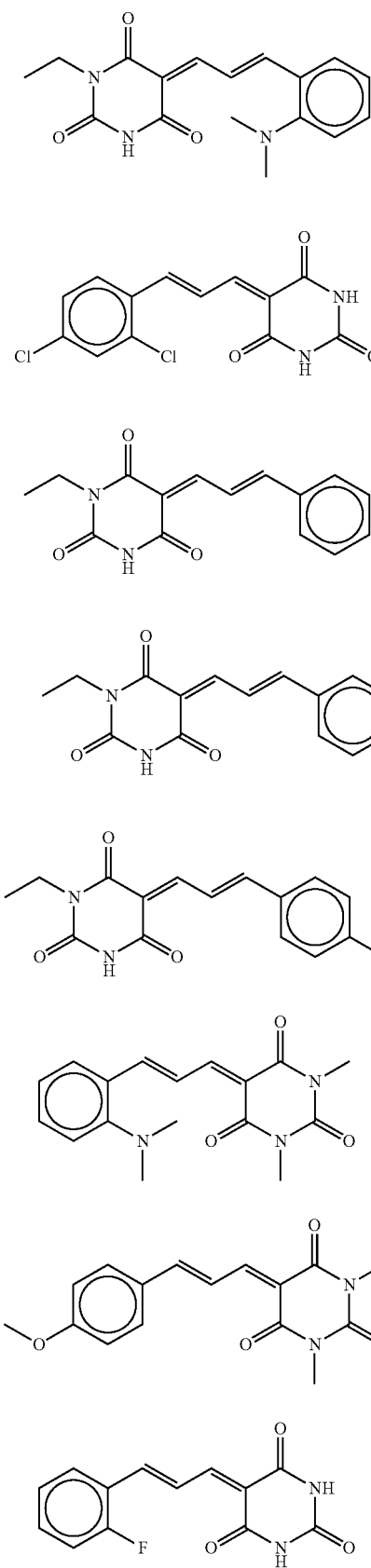

DDD00175811
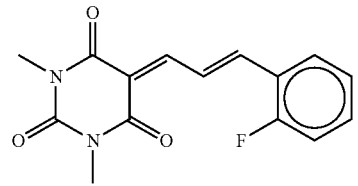
DDD00175796
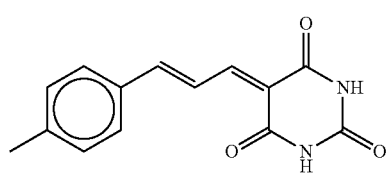
DDD00175801
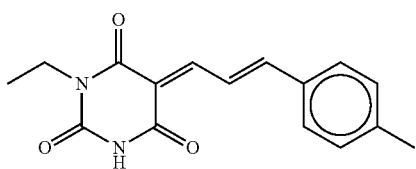
DDD00175810
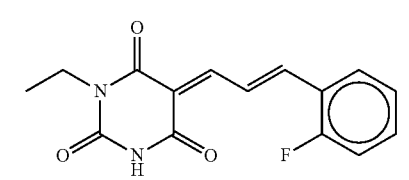
DDD00197355
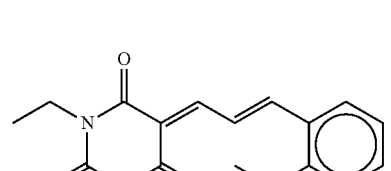
DDD00197346
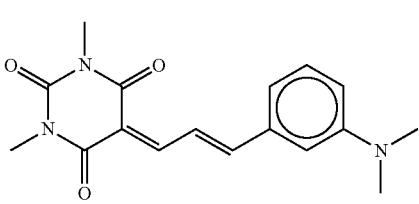
DDD00175799
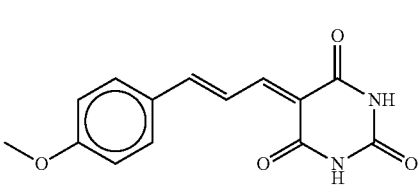
DDD00197330
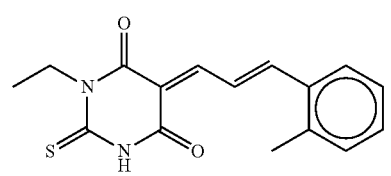
DDD00197329
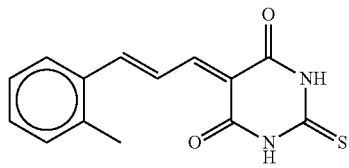
DDD00197331
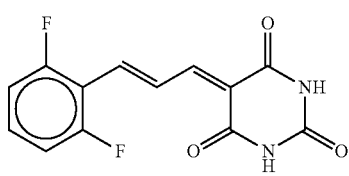
DDD00175797
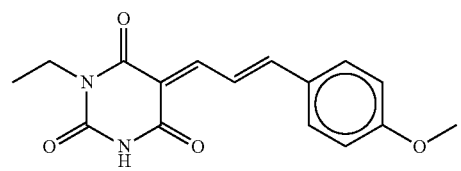
DDD00175817
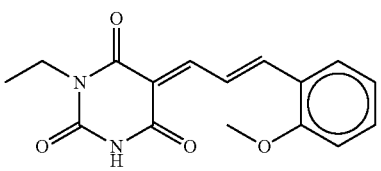
DDD00175818
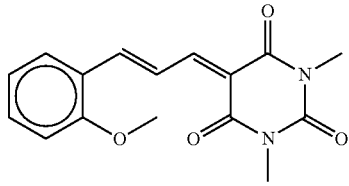
DDD00197343
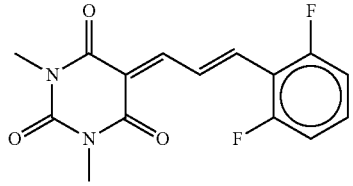
DDD00197349
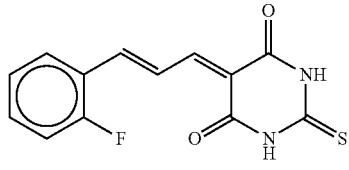
DDD00175809
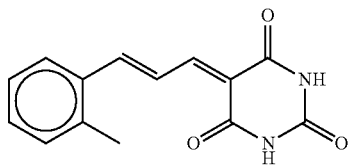

-continued

| DDD00125643 |
| DDD00175819 |
| DDD00197348 |
| DDD00175789 |
| DDD00175804 |
| DDD00175805 |
| DDD00175842 |
| DDD00197339 |

-continued

| DDD00175813 |
| DDD00175798 |
| DDD00197337 |
| DDD00175802 |
| DDD00175803 |
| DDD00124808 |
| DDD00197354 |
| DDD00124818 |
| DDD00197336 |

37
-continued
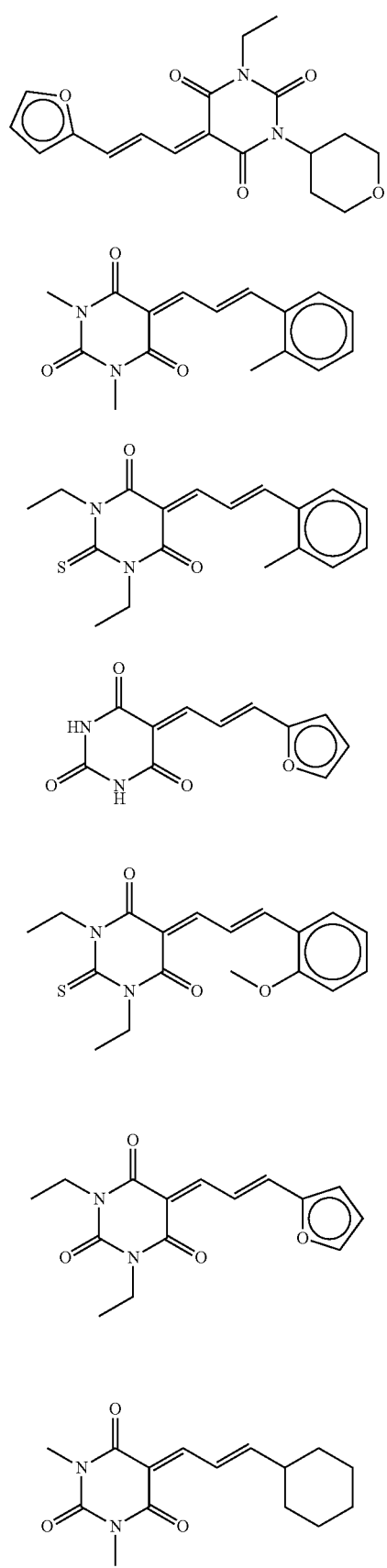
38
-continued
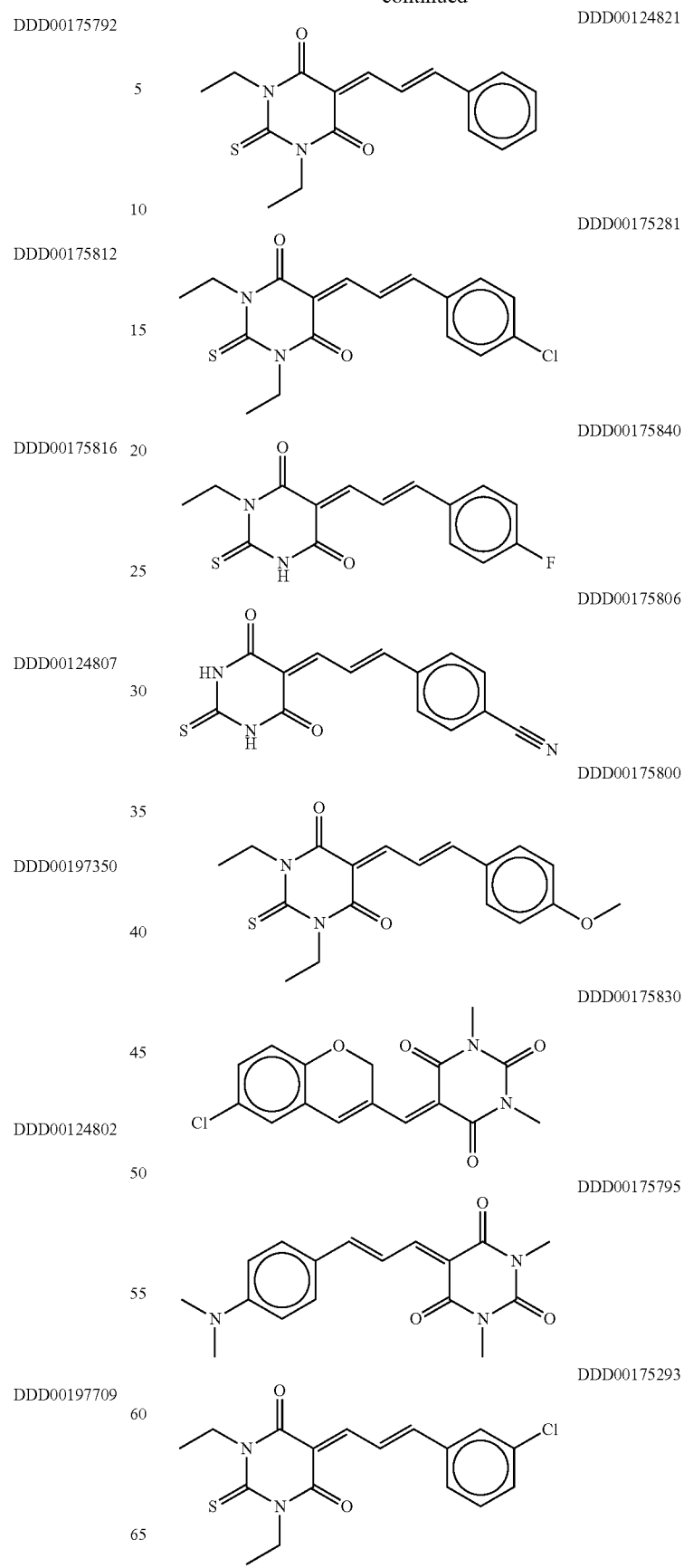

-continued

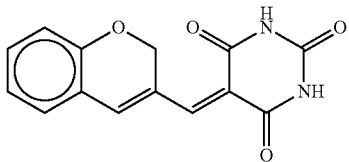
DDD00175835

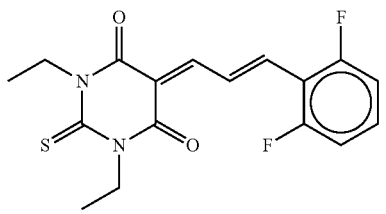
DDD00197345

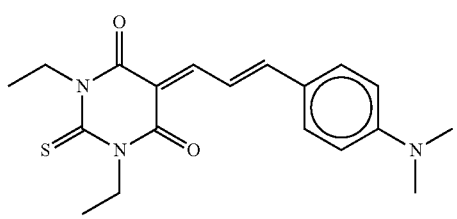
DDD00197342

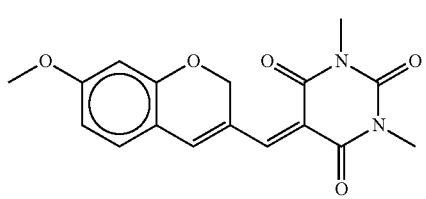
DDD00175826

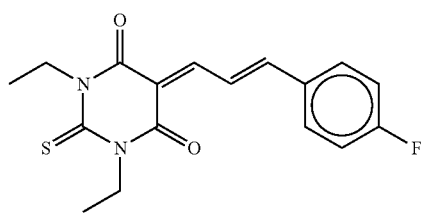
DDD00175839

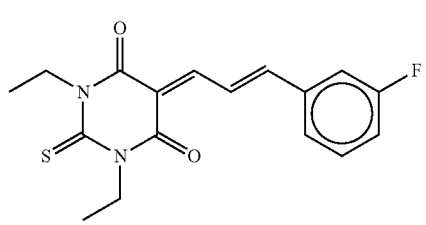
DDD00197335

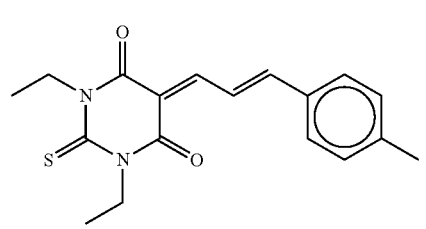
DDD00175807

The code number (DDD number) given with each compound is used as a shorthand for referring to specific compounds at certain appropriate points in this application In this second embodiment of the invention, the cancer is not especially limited. However, typically the cancer is one that comprises a tumor, wherein the tumor is selected from the classes of tumors consisting of carcinomas, sarcomas, leukemias, lymphomas, myelomas, melanomas, central nervous system tumors, peripheral nerve tumors, and metastatic tumors. The cancer may typically comprise a tumor selected from glioma, brain stem glioma, mixed glioma, optic nerve glioma, astrocytoma, meningioma, pituitary adenoma, vestibular schwannoma, primary CNS lymphoma, primary neuroectodermal tumor, neurofibroma, malignant peripheral nerve sheath tumor, schwannoma, leptomeningeal tumors, germ cell tumor, choriocarcinoma, endodermal sinus tumor, chordoma, craniopharyngioma, ependymoma, subependymoma, medulloblastoma, oligodendroglioma, pituitary tumors, pineal tumor, rhabdoid tumor and tumors that have metastasized to the brain. The cancer may comprise a tumor cell, such as those selected from pituitary adenoma, vestibular schwannoma, primary CNS lymphoma, primary neuroectodermal tumor, neuroblastoma, neurofibroma, malignant peripheral nerve sheath tumor, schwannoma, skin cancer, lung cancer, colon cancer, pancreatic cancer, ovarian cancer, epithelial carcinoma, squamous cell carcinoma, basal cell carcinoma, osteosarcoma, synovialsarcoma, liposarcoma, angiosarcoma, rhabdosarcoma, fibrosarcoma, lymphoblastic leukemia myelogenous leukemias, T-cell leukemia, hairy-cell leukemia, T-cell lymphomas, B-cell lymphomas, Hodgkin lymphomas, non-Hodgkin lymphoma, lymphoproliferative lymphomas, central nervous system cancer and metastatic cancers.

Thus, typically the cancer is a cancer selected from neuroblastoma, neurofibroma, malignant peripheral nerve sheath tumor, head and neck cancer, breast cancer, ovarian cancer, renal medullary carcinoma, prostate cancer, gastric cancer, cervical cancer, brain cancer, peripheral nerve tumors, lung cancer, leukaemia, colorectal cancer, colon cancer, spinal tumor, bone cancer, liver cancer, lymphoma, melanoma, pancreatic cancer, thyroid cancer, uterine sarcoma, testicular cancer, and metastatic cancer.

As with the first embodiment of the invention, the cancer in the second embodiment may be a drug-resistant cancer and/or a radiation-resistant cancer (the resistance may be total or partial) although this second embodiment may also be used against non-drug-resistant cancers and non-radiation-resistant cancers too. The drug-resistant cancer is typically resistant to one or more of temozolomide, geldanamycin, geldanamycin derivatives, and/or doxorubicin, although any drug resistance may be envisaged. The radiation-resistant cancer is typically a cancer that has shown resistance against one or more known radiation treatments. The cancer may be both drug-resistant and radiation resistant in some cases, or may be only drug-resistant or only radiation-resistant.

The second embodiment of the invention also provides use of a compound for the preparation of a medicament for treating cancer, wherein the compound is a compound as defined above.

The second embodiment further provides a pharmaceutical composition for treating a cancer, which composition comprises one or more compounds as defined above.

The second embodiment also provides compounds of the following formulae:

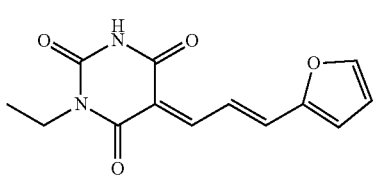

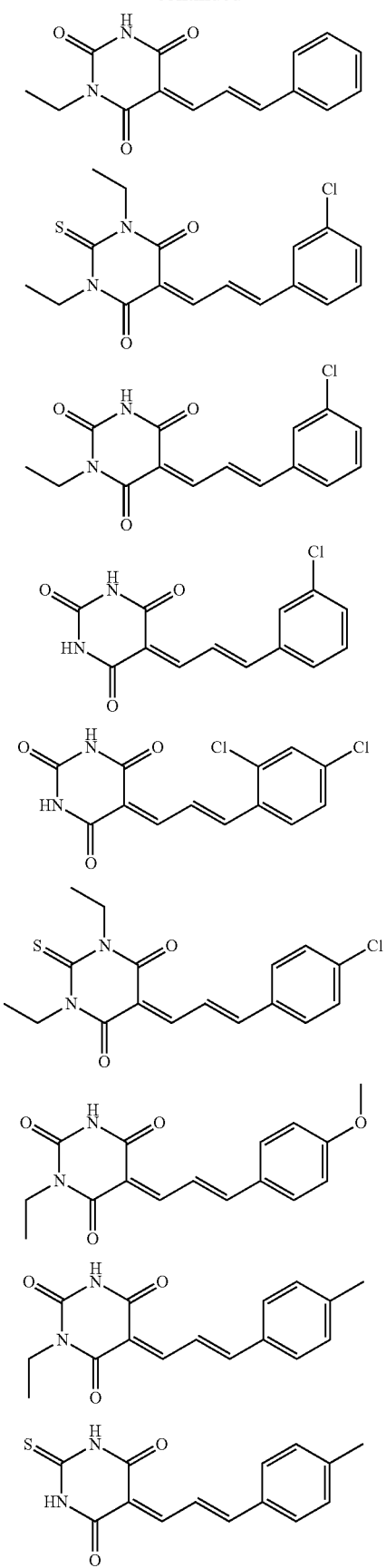
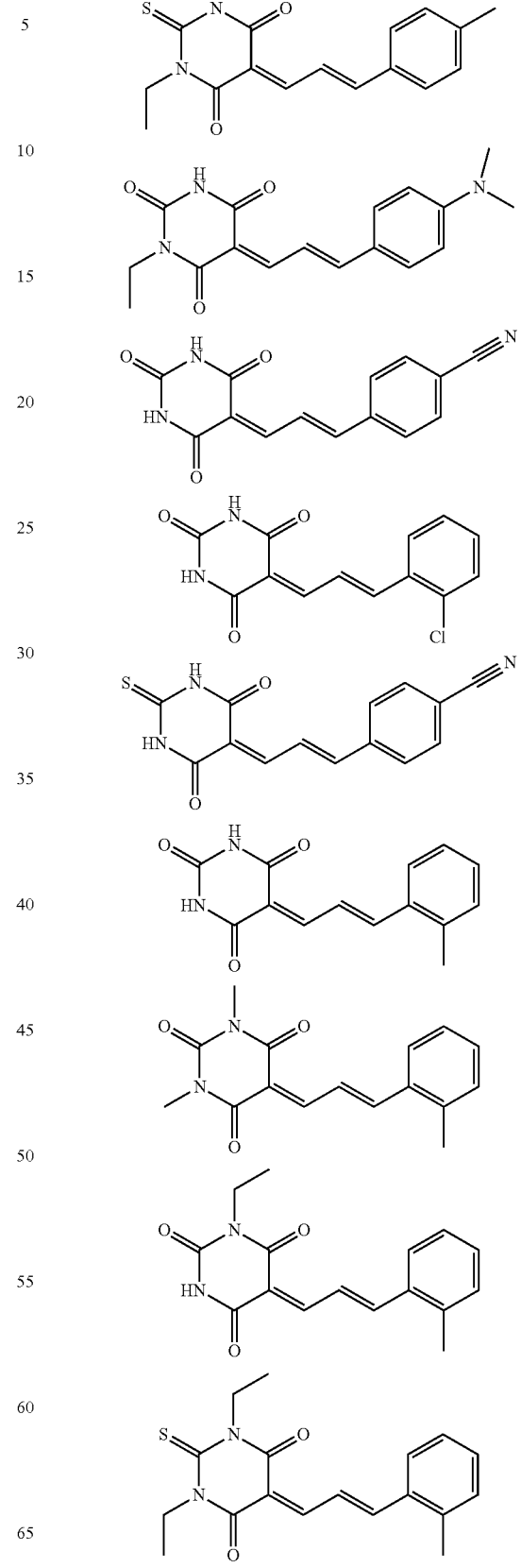

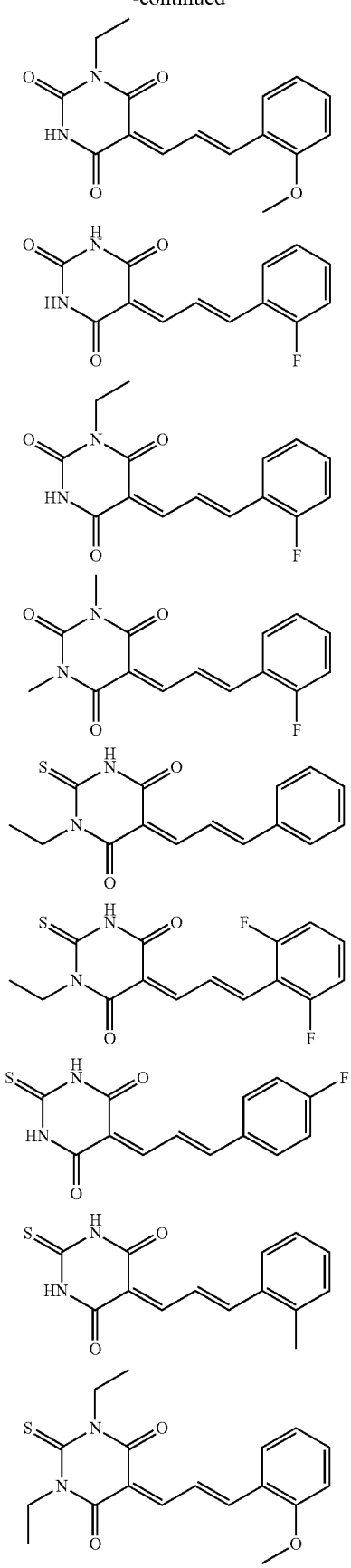
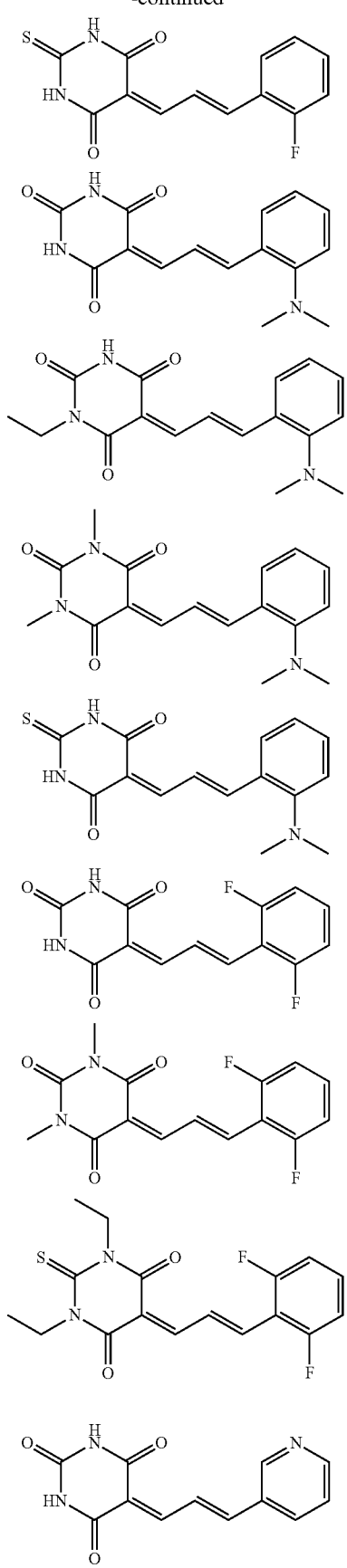

45
-continued
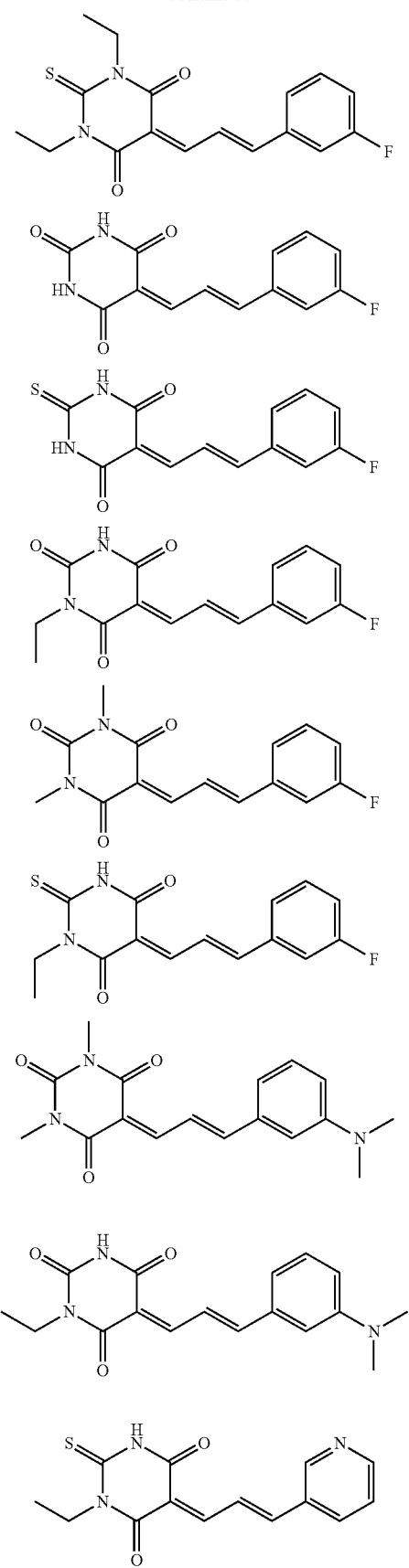
46
-continued
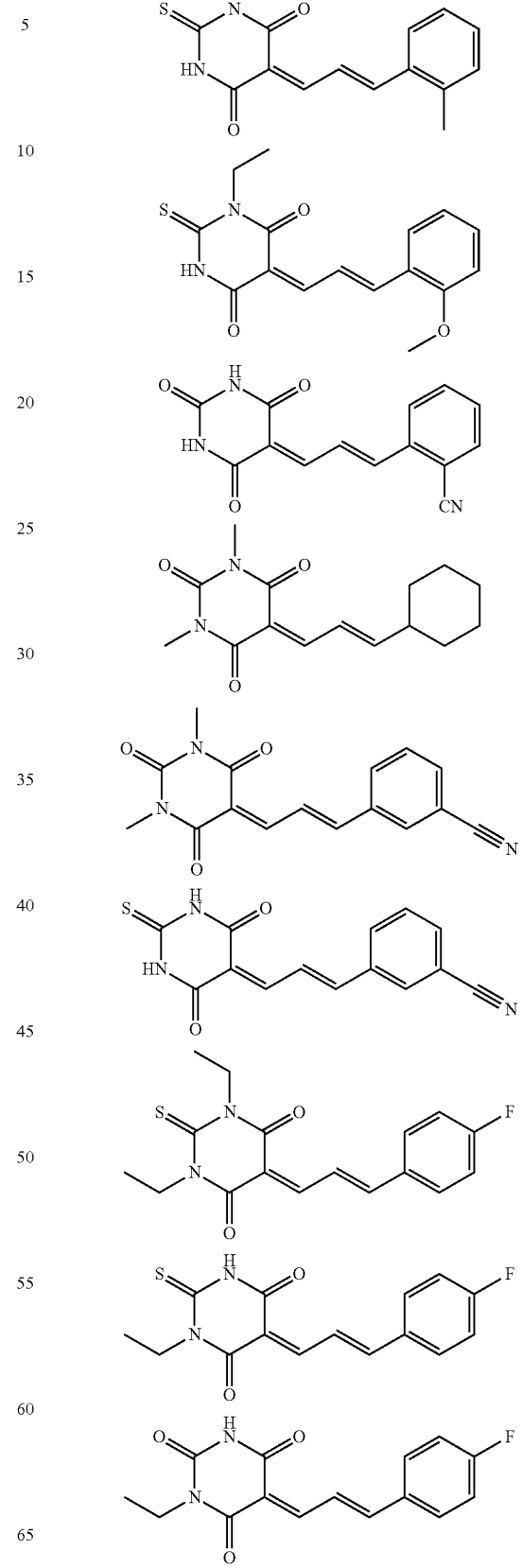

-continued

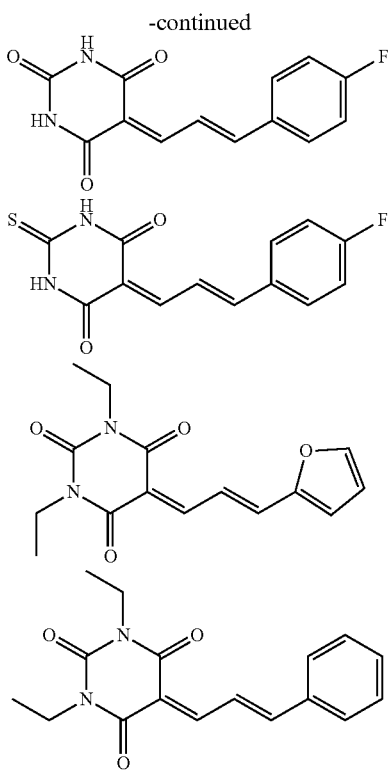

or a derivative, homologue, prodrug, solvate, or pharmaceutical salt thereof This embodiment also provides pharmaceutical compositions comprising one or more such compounds.

The second embodiment further provides a method for treating cancer in a mammalian subject, which method comprises administering a compound or composition as defined above to a mammalian subject. In this method the cancer is a cancer as defined above.

In the second embodiment, preferably, the subject is a mammal, for example selected from a human, companion animal, non-domestic livestock or zoo animal. For example, the subject may be selected from a human, dog, cat, cow, pig, sheep, horse, bear, and so on.

In all of the embodiments of the invention, the mammalian subject is typically a human.

In all of the embodiments of the invention, where the compound may be chiral the invention encompasses both the S- and the R-enantiomer as well as racemic mixtures of the isomers. In addition, in all of the embodiments of the invention, where the compound may possess regioisomerism as a result of the presence of one or more double bonds, the E- and the Z-isomers are encompassed as well as mixtures of these.

Syntheses and Preparation

The preparation and use of exemplary compounds of embodiment 1 of the invention is further described below.

All of the compounds for use in the present invention, for example, Formulae I-XXII, and the compounds for use in the second embodiment, can be prepared using techniques known in the art. For example, CC-I (Formula IV) can be prepared by the following reaction (Scheme 1):

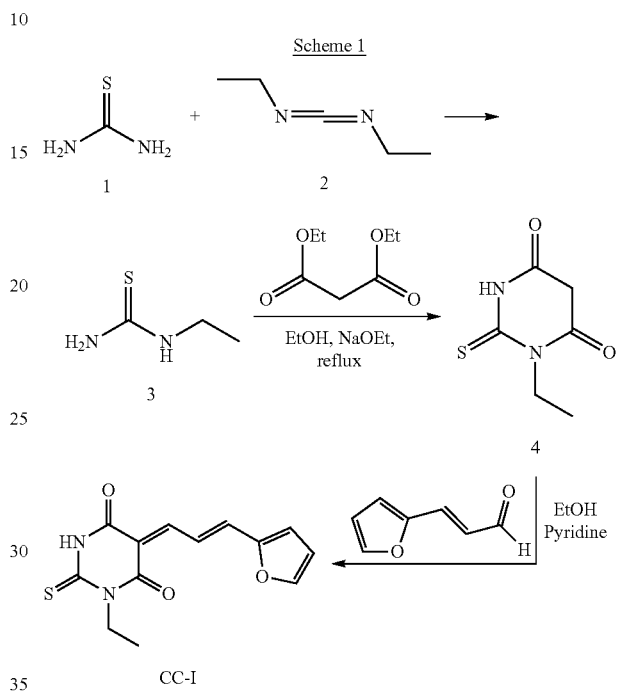

The key intermediate N-ethylthiobarbituric acid (4) can be synthesized starting from a reaction of thiourea with N-ethyl carbodiimide (2) to yield N-ethylthiourea (3) (45, 46), followed by the treatment of (3) with diethylmalonate in ethanol in the presence of sodium ethoxide. The reaction of (4) with trans-3-(2-furyl)-acrolein in ethanol in the presence of catalytic amount of pyridine will lead finally to the desired compound CC-I (Formula IV).

Other compounds of the invention (Formulae X, XI, XVI, XVII, and XVIII) can be synthesized following a similar strategy by treating appropriately N-ethenyl/allyl substituted thiobarbituric acid analogs. The precursor N-alkylthiobarbituric acid (10) can be synthesized starting from thiourea and appropriately substituted carbodiimide synthesized as outlined in Scheme 2. The reaction of substituted carbodiimides (5-9) with diethylmalonate will yield N-alkyl/allyl thiobarbituric acid which on reaction with trans-3-(2-furyl)-acrolein will yield the CC-I derivatives.

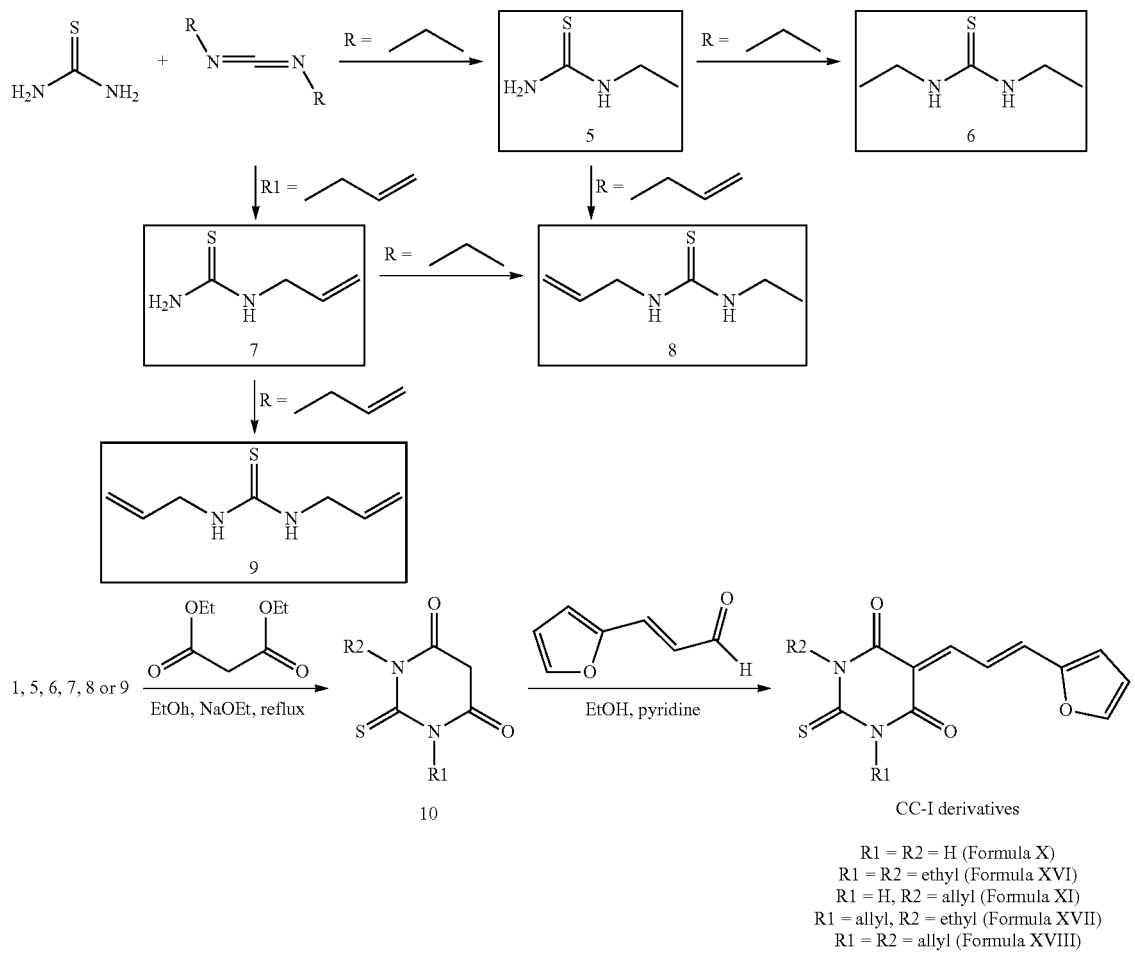
Other CC-I derivatives (Formulae V. IX, XIX, XX, XXI, and XXII) can be synthesized following similar synthetic strategy as adopted for CC-I by treating thiobarbituric acid or appropriately substituted thiobarbituric acid (10) with cinnamaldehyde as outlined in Scheme 3.
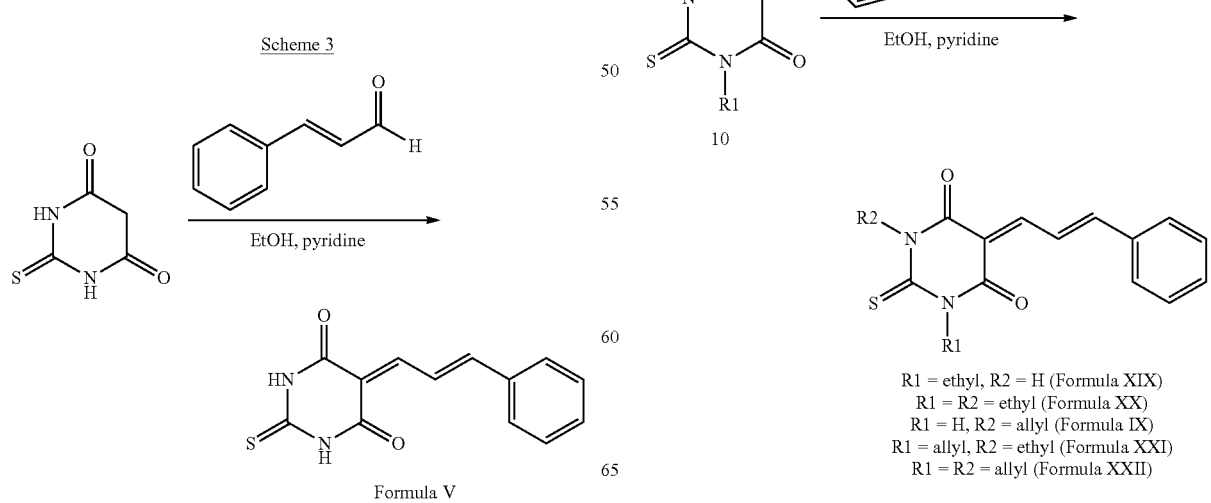

Formula XII can be synthesized by condensing thiobarbituric acid with aldehyde (11) at ~60° C. in ethanol with catalytic amount of pyridine (Scheme 4).

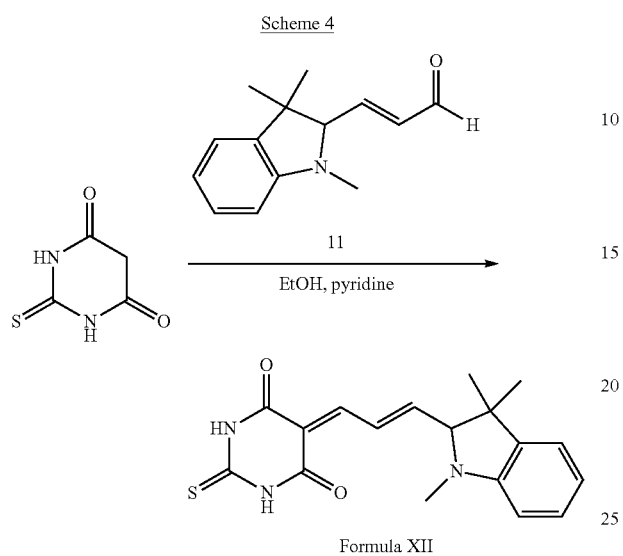

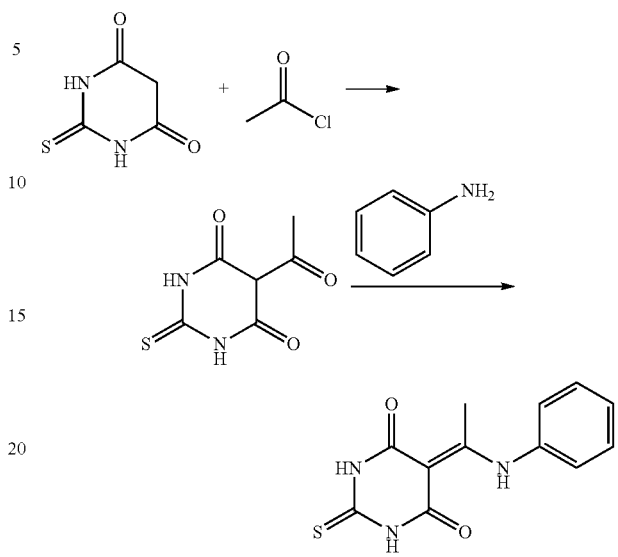

Formulae XIV and XV can be synthesized by the coupling of thiobarbituric acid with aryldiazonium salts (12) as shown in Scheme 5. Briefly, the treatment of thiobarbituric acid in ethanol, in the presence of sodium acetate and 1M sodium hydroxide at 0-5° C., with the appropriately substituted diazonium salt (12), will yield Formulae XIV and XV.

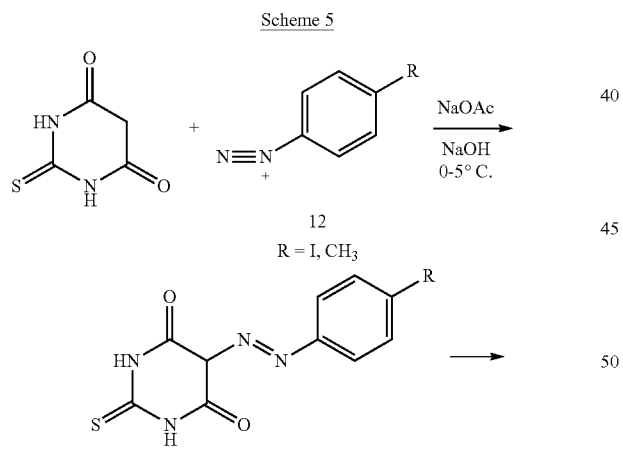

Formula XIII can be synthesized by condensing thiobarbituric acid with acetyl chloride followed by treatment with aniline as shown in Scheme 6.

Formula VI-VIII can be synthesized following similar synthetic methods as described above by condensing thiobarbituric acid or N-allyl thiobarbituric acid with appropriate aldehydes as described in Scheme 7 below.

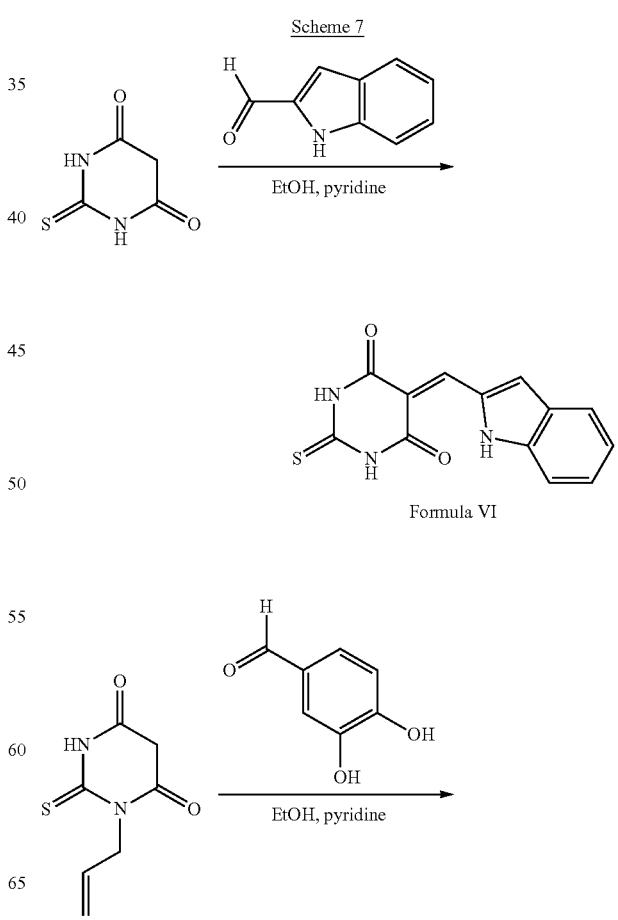

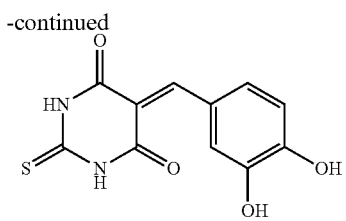

Formula VII

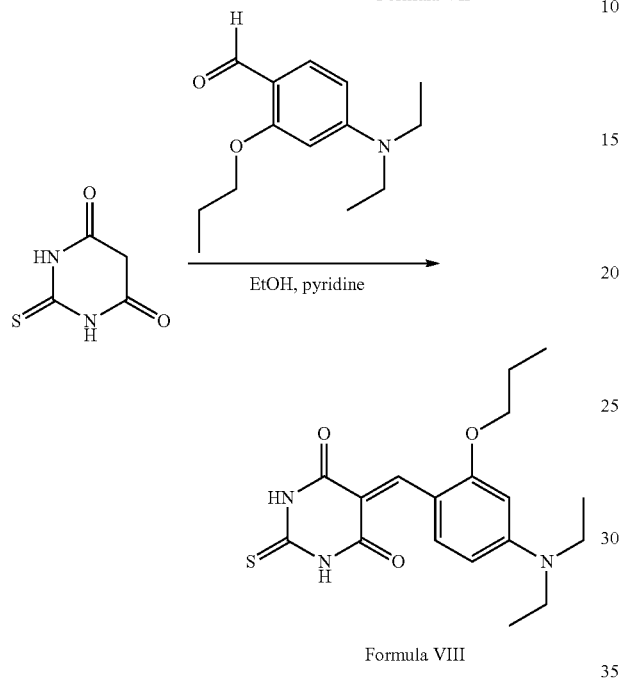

Formula VIII

The final products can be purified by silica gel column chromatography and their purity determined by analytical high-pressure liquid chromatography (HPLC). The purified compounds can be characterized on the basis of their NMR and Mass spectra. A purity level of ≥98% is expected for the final compounds following further purification, for example, chromatography, or chromatography followed by crystallization.

Synthesis and preparation of exemplary compounds of the second embodiment of the invention are discussed below.

Equipment

Reactions using microwave irradiation were carried out in a Biotage Initiator microwave.

Normal phase TLCs were carried out on pre-coated silica plates (Kieselgel 60 F254, BDH) with visualization via U.V. light and/or KMnO4 solution. Flash chromatography was performed using Combiflash Companion Rf (Teledyne) and pre-packed silica gel columns purchased from Grace Davison Discovery Science. Mass-directed preparative HPLC separations were performed using a Waters HPLC (2545 binary gradient pumps, 515 HPLC make up pump, 2767 sample manager) connected to a Waters 2998 photodiode array and a Waters 3100 mass detector. Preparative HPLC separations were performed with a Gilson HPLC (321 pumps, 819 injection module, 215 liquid handler/injector) connected to a Gilson 155 UV/vis detector. On both instruments, HPLC chromatographic separations were conducted using Waters XBridge C18 columns, 19×100 mm, 5 um particle size; using 0.1% ammonia or 0.1% formic acid in water (solvent A) and acetonitrile (solvent B) as mobile phase. 1H-NMR spectra were recorded on a Brucker Avance DPX500 spectrometer using the applied solvent simultaneously as internal standard. Low resolution electrospray (ES) mass spectra were recorded on a Brucker MicroTof mass spectrometer, run in positive mode. LC-MS analysis and chromatographic separation were conducted with a Brucker MicroTof mass spectrometer using an Agilent HPLC 1100 with a diode array detector in series. The column used was a Waters XBridge column (5×50 mm) and the compounds were eluted with a gradient of 5 to 95% acetonitrile/water+ 0.1% ammonia. Low resolution electrospray (ES) mass spectra were also recorded on an Agilent 6130 Quadrupole mass spectrometer, run in positive or negative mode. LC-MS analysis and chromatographic separation were conducted with an Agilent 6130 Quadrupole mass spectrometer using an Agilent HPLC 1200 with a diode array detector in series. The column used was a Waters XBridge column (5×50 mm) and the compounds were eluted with a gradient of 5 or 20 to 95% acetonitrile/water+0.1% formic acid.

Unless otherwise stated herein reactions have not been optimized. Solvents and reagents were purchased from commercial suppliers and used without further purification.

The preparations and compounds have been named using the ChemDraw Ultra 12.0 naming application.

Cinnamaldehyde Synthesis

Method A Example—(E)-3-(o-tolyl)acrylaldehyde—
Made According to Route in JACS, 133, 2011, 6642-6656

Step 1

To a suspension of NaH (60% dispersion in mineral oil, 1.4 g, 36.75 mmol) in 100 ml of anhydrous THF, cooled in an ice bath, was added ethyl 2-(diethoxyphosphoryl)acetate (9.88 g, 44.1 mmol). After the solution became clear, 2-methylbenzaldehyde (1.76 g, 14.7 mmol) was added as a solution in anhydrous DCM (50 ml) and the reaction stirred at room temperature for 2 hrs. The reaction was quenched by the addition of water and the organics extracted with ethyl acetate (2×150 ml), dried (sodium sulfate), filtered and absorbed onto SiO2. Purification by flash chromatography (gradient 0-10% EtOAc in hexane) afforded the title compound. RT=2.61 min, m/z (ES+)=207.1 [M+H]+

Step 2

To a solution of (E)-ethyl 3-(o-tolyl)acrylate (3.8 g, 20 mmol) in 150 ml of anhydrous DCM, cooled to −78° C. was added a DIBAL-H solution (60 ml, 60 mmol) in heptane (1 M). The mixture was stirred at −78° C. for 30 mins before the reaction was quenched by the addition of MeOH and allowed to warm to room temperature. Then a saturated aqueous solution of sodium potassium tartrate (150 ml) was added to the reaction mixture and the organics extracted with ethyl acetate (2×150 ml), dried (sodium sulfate), filtered and absorbed into SiO$_2$. Purification by flash chromatography (gradient 0-30% EtOAc in hexane) afforded the title compound.

Step 3

Activated MnO$_2$ (4.9 g, 57.4 mmol) was added to a solution of (E)-3-(o-tolyl)prop-2-en-1-ol (1.7 g, 11.5 mmol) and the reaction mixture stirred for 18 hrs at r.t. The reaction mixture was filtered through celite and concentrated in vacuo to afford the title compound. RT=2.42 min, m/z (ES+)=147.1 [M+H]+

Method B Example—(E)-3-(3-chlorophenyl)acrylaldehyde—Method Taken from JOC, 2011,76. 8986-8998

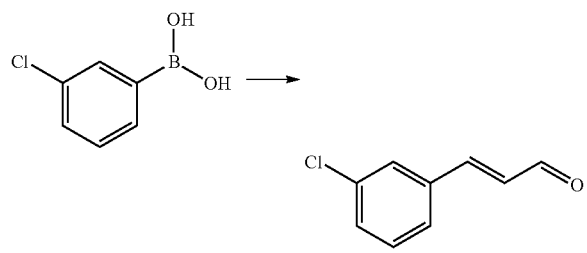

Pd(OAc$_2$) (22.4 mg, 0.1 mmol) and Neocuproine (dmphen) (25 mg, 0.12 mmol) were mixed in MeCN (5 ml) and stirred for 30 minutes, resulting in a complete solution. In another flask the acrolein (315 μl, 5 mmol), benzoquinone (540 mg, 5 mmol) and 3-Cl phenylboronic acid (1.56 g, 10 mmol) were mixed in MeCN (15 ml). The catalyst/ligand mixture was added to this second flask and the reaction was stirred at room temperature overnight. The reaction mixture was absorbed onto SiO$_2$ and purified on a 25 g SiO$_2$ cartridge, eluting with 10-50% Et$_2$O in hexane. The product was isolated as an orange colored oil which solidified on standing.

Method C Example—Synthesis of (E)-2-(3-oxoprop-1-en-1-yl)benzonitrile

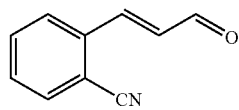 [SMILES: N#Cc1ccccc1/C=C/C=O]

To a solution of 2-bromobenzonitrile (500 mg, 2.75 mmol) in DMA (5 ml) was added 3,3-diethoxyprop-1-ene (1.07 g, 8.24 mmol), DIPEA (0.5 ml) and Herrman's catalyst (51.6 mg, 0.055 mmol). The reaction mixture was heated at 90° C. for 18 hrs. On cooling the mixture was acidified with 1 N HCl and the organics extracted with ethyl acetate (15 ml). The organics were washed with brine (20 mls), dried (sodium sulfate), filtered and absorbed onto SiO$_2$. Purification by flash chromatography (gradient 0-20% EtOAc in hexane) afforded the title compound. RT=4.4 min, m/z (ES+)=158.07 [M+H]+

Method D Example—(E)-3-(4-fluorophenyl)acrylaldehyde—Method Taken from Org. Lett., Vol. 5, No. 5, 2003

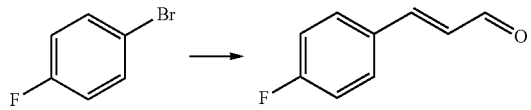 [SMILES: Fc1ccc(Br)cc1 ; O=C/C=C/c1ccc(F)cc1]

1-bromo-4-fluorobenzene (3.0 g, 17.1 mmol), Pd(OAc)$_2$ (115 mg, 0.5 mmol), tetrabutylammonium acetate (12.4 g, 34.2 mmol), potassium carbonate (2.43 g, 17.6 mmol), potassium chloride (1.27 g, 17.1 mmol) and acrolein diethyl acetal (6.68 g, 51.3 mmol) were added to DMF (68.4 ml). The reaction was heated under an argon atmosphere at 90° C. for 28 hours. The reaction was allowed to cool to room temperature before adjusting the pH to 1 by addition of 2 N HCl(aq). The mixture was stirred at room temperature for 20 minutes before extracting into diethyl ether (X3). The combined organics were washed with water (X2) followed by brine (X2). The organics were dried over magnesium sulphate before removing the solvent in vacuo. The crude material was purified by silica column chromatography (hexane>20% ethyl acetate/hexane) to afford the title compound as a very pale yellow oil after solvent evaporation. The oil solidified on standing. (1.82 g, 71%).

Synthesis of 1-ethylpyrimidine-2,4,6(1H,3H,5H)-trione

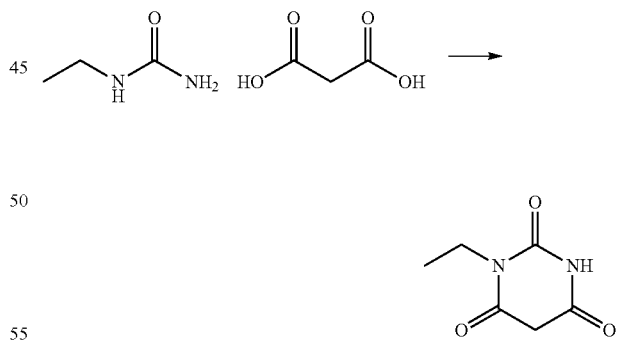

Ethylurea (5 g, 57 mmol) and malonic acid (6.22 g, 60 mmol) were mixed in AcOH (12 ml) and heated to 80° C. Acetic anhydride (12 ml) was then added over 2 hours. The reaction mixture was heated at 90° C. overnight. The reaction mixture was cooled and evaporated in vacuo. The residue was triturated with EtOH and the solid obtained was filtered off, washed well with EtOH and dried, yielding the title compound as a pale yellow solid. (3.5 g, 40%).

Synthesis of 1-ethyl-3-(tetrahydro-2H-pyran-4-yl)pyrimidine-2,4,6(1H,3H,5H)-trione—Method Taken from WO 2007150011A2

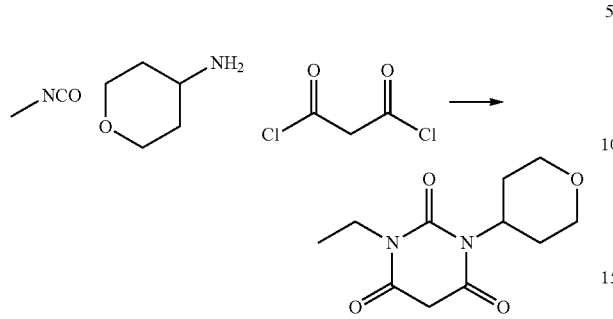

Tetrahydro-2H-pyran-4-amine (516 µl, 5 mmol) was mixed in CHCl$_3$ and the ethylisocyanate (395 µl, 5 mmol) was added and the reaction mixture stirred for 2 hours. The malonyl dichloride (491 µl, 5.05 mmol) was added and the reaction mixture heated at 50° C. for 2 hours. The reaction mixture was cooled, washed with 1 N HCl, passed through a hydrophobic frit and absorbed onto SiO$_2$. The crude product was then purified on a 40 g SiO$_2$ cartridge eluting with 20-100% EtOAc in hexane. This yielded the title compound as a colorless gum which solidified. (828 mg, 69%).

Knoevenagel Method A—(E/Z)-1-ethyl-5-((E)-3-(furan-2-yl)allylidene)pyrimidine-2,4,6(1H,3H,5H)-trione

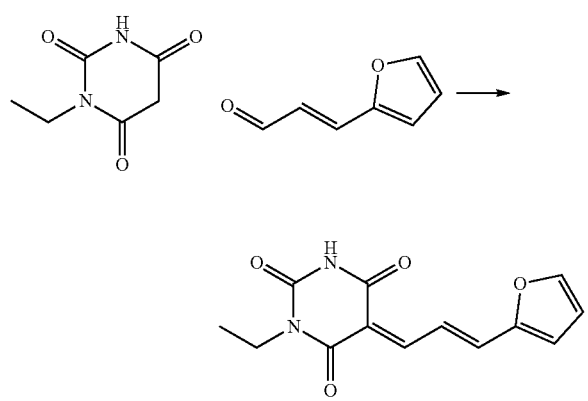

1-ethylbarbituric acid (1 g, 6.4 mmol), 3-(2-furyl)acrolein (0.78 g, 6.4 mmol), piperidine (63 µl, 0.64 mmol) and benzoic acid (78 mg, 0.64 mmol) were mixed in toluene (70 ml) and then heated at reflux with a Dean & Stark head for 12 hours. The reaction mixture was cooled and the toluene was evaporated off. The residue was partitioned between brine and EtOAc and extracted 3 times. The combined organics were washed with brine, dried (MgSO$_4$) and the residue was purified by flash chromatography, eluting with 20-50% EtOAc in hexane. Further purification by prep HPLC (XBridge, 0.1% HCO$_2$H modifier) yielded the product as an orange colored solid (115 mg, 7%) M.S. (ESI) (m/z): 261 [M+H]+.

Knoevenagel Method B—E-5-(3-furan-2-yl)allylidene)pyrimidine-2,4,6(1H,3H,5H)-trione

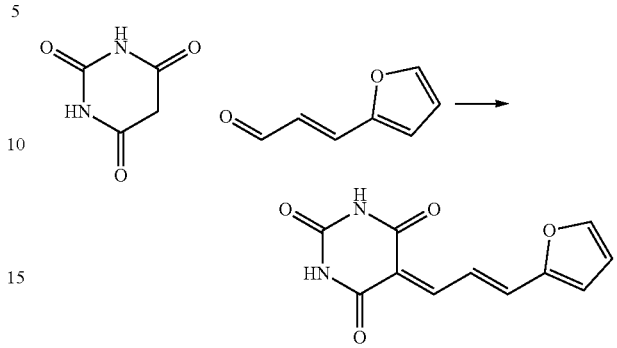

Barbituric acid (550 mg, 4.3 mmol), 3-(2-furyl)acrolein (524 mg, 4.3 mmol) and pyridine (4 drops) were mixed in EtOH (10 ml) and microwaved at 90° C. for 20 minutes. The resulting bright orange solid was diluted with a 50:50 H$_2$O/EtOH mix, filtered off, washed well with EtOH and Et$_2$O and dried (850 mg, 85%) M.S. (ESI) (m/z): 233 [M+H]+.

Further compounds of the invention were made using Knoevenagel method B, reacting barbituric or thiobarbituric acids with substituted cinnamaldehydes or aldehydes (purchased or synthesized via methods A,B or C).

Administration

The compounds of the first and second embodiments can be administered in the form of a pharmaceutically acceptable salt or solvate, or a prodrug. The compounds can be used to reduce tumor size and to induce apoptosis in tumor cells, or to treat cancer generally. Tumors to be treated may include, but are not limited to, carcinoma (e.g., skin, lung, colon, pancreatic, ovarian cancer, epithelial carcinoma, squamous cell carcinoma, basal cell carcinoma), melanoma, sarcoma (e.g., osteosarcoma, synovial sarcoma, liposarcoma, angiosarcoma, rhabdosarcoma, fibrosarcoma), leukemia (e.g., lymphoblastic leukemias, myelogenous leukemia, T-cell leukemia, hairy-cell leukemia), lymphoma and myeloma (e.g., T-cell lymphoma, B-cell lymphoma, Hodgkin lymphoma, non-Hodgkin lymphoma, lymphoproliferative lymphoma), central nervous system cancers (e.g., glioma, meningioma, pituitary adenoma, vestibular schwannoma, primary CNS lymphoma, primary neuroectodermal tumor), nerve tumor (e.g., neuroblastoma, malignant peripheral nerve sheath tumor, neurofibroma, schwannoma) and metastatic cancer.

The compounds can be administered in different regimens and dosages to achieve an effective amount. The compound is preferably administered weekly, but may also be administered more or less frequently as needed. The selected dosage will depend on factors such as the activity and rate of excretion of the compound selected, the route of administration, timing of administration, duration of treatment, other drugs or material used in combination with compound selected, the age, sex, weight, condition, general health and medical history of the subject being treated and similar factors known in the medical art. The compound is preferably administered as a pharmaceutical composition.

A physician or veterinarian having ordinary skill in the art can readily determine and prescribe a therapeutically effective amount of the pharmaceutical composition to be administered. Generally, effective doses of the compounds of the invention will range from about 0.0001 to about 1000 mg/kg body weight, preferably from about 1.0 to 100 mg/kg, most preferably from about 10 to 50 mg/kg. Once-a-week administration is preferred, but the compounds may also be administered more or less often than weekly, e.g., daily, every other day, bi-weekly, bi-monthly, etc.

Pharmaceutical compositions of the compounds of the invention are formulated to be compatible with the intended route of administration, e.g., oral, rectal, parenteral, intravenous, intrathecal, intranasal or other modes of administration. Pharmaceutical formulations are generally prepared by mixing the active substance with a conventional pharmaceutically acceptable diluent or carrier. Carriers and diluents are pharmaceutically acceptable if they are compatible with the ingredients of the formulation and not injurious to the treated subject. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical compounds is well known in the art. Supplementary active ingredients can also be incorporated into the compositions. Examples of carriers include sugars, such as lactose, glucose and sucrose; starches, such as corn and potato starch; cellulose and its derivatives, powdered tragacanth; malt; gelatin; talc; excipients, such as cocoa butter and suppository waxes; oils, such as peanut, cottonseed, safflower, sesame, olive, corn, and soybean oils; glycols; polyols, such as glycerin, sorbitol, mannitol, and polyethylene glycol; esters, such as ethyl oleate and ethyl laurate; agar; buffering agents; alginic acid; pyrogen-fee water; isotonic saline; Ringer's solution; ethyl alcohol; phosphate buffer solutions; and other non-toxic compatible substances employed in pharmaceutical formulations. Pharmaceutical formulations may also contain additional ingredients such as stabilizers, wetting agents, emulsifiers, lubricants, coloring agents, sweetening and flavoring agents, perfuming agents, preservatives, lubricants, releasing agents, and antioxidants.

Compositions may be prepared in unit dosage form for ease of administration and uniformity of dosage. "Unit dosage form" refers to physically discrete units suited as unitary dosages for the subject to be treated; each unit containing a predetermined quantity of active compound calculated to produce the desired therapeutic effect in association with the required pharmaceutical carrier. Compositions can be prepared by known methods in the art, for example, granulation, compression, microencapsulation, spray coating, etc. The formulations may be prepared by conventional methods, for example methods for preparing tablets, capsules, granules, powders, syrups, suspensions, suppositories, and injectable solutions.

For parenteral administration in an aqueous solution, for example, the solution should be suitably buffered if necessary and the liquid diluent first rendered isotonic with sufficient saline or glucose. These particular aqueous solutions are especially suitable for subcutaneous, intramuscular, and intratumoral administration. Diluents include water, saline, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH of the solution can be adjusted with acids or bases, such as hydrochloric acid or sodium hydroxide. The parenteral preparation can be enclosed in ampoules, disposable syringes or multiple dose vials made of glass or plastic. For human administration, preparations should meet sterility, pyrogenicity, general safety and purity standards as required by FDA Office of Biologics standards.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum mono stearate and gelatin.

Sterile injectable solutions can be prepared by incorporating the active compound (e.g., a compound according to an aspect of the invention) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The compounds can also be prepared with carriers that will prevent rapid elimination of the active compound from the body, such as controlled release formulations, including implants and microencapsulated delivery systems. Biodegradable, biocompatible polymers can be used, such as ethylene vinyl acetate, polyanhydrides, polyglycolic acid, collagen, polyorthoesters, and polylactic acid.

The toxicity and therapeutic efficacy of the compounds can be determined by standard pharmaceutical procedures using cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit broad therapeutic indices are preferred. While compounds exhibiting toxic side effects may be used, care should be taken to design a delivery system that specifically targets such compounds to the site of affected tissue in order to minimize potential damage to uninfected cells and, thereby, reduce side effects.

The therapeutic treatment described herein may be used in combination with additional therapeutic agents to more effectively treat cancer. Additional therapeutic agents include traditional anticancer therapies. Anticancer agents may include but are not limited to, radiotherapy, chemotherapy, gene therapy, hormonal therapy or immunotherapy that targets cancer/tumor cells.

Aspects of the invention are further illustrated by the following examples. These examples should not be construed as limiting, as those of skill in the art will recognize many equivalents to the specific aspects and methods described herein. Animal models used in the Examples are accepted animal models in the art and demonstration of efficacy in these animal models is predictive of efficacy in humans.

EXAMPLES

Methods for Cell Culture

Human neuroblastoma cell lines were cultured in Dulbecco's Modified Eagle Medium (DMEM)/F12 media. Human glioma cells were ordered from American Type Culture Collection (ATCC, Manassas, Va.), and maintained in DMEM with $4 \times 10^{-3}$M L-glutamine, 100 U/ml penicillin, 100 µg/ml streptomycin, and 10% fetal bovine serum (FBS). All experiments were performed at 37° C. in 5% $CO_2$ atmosphere under cell culture conditions. Prior to γ-radiation or exposure to chemotherapeutic agents, the glioma cells were plated at a density of 156 to 8,000 cells per well in 96 well plates to account for differences in growth rates, and to obtain similar cell densities for the experimental manipulations, and cultured overnight. Then cells received different dosages of γ-radiation from a $^{60}$Co source GammaCell 220 (Nordion International Inc, Ontario, Canada) or chemotherapeutic agents for another 2-6 days. Cell cytotoxicity assay was determined by MTS [3-(4,5-dimethylthiazol-2-yl)-5-(3-carboxymethoxyphenyl)-2-(4-sulfophenyl)-2H-tetrazolium, inner salt] Cell Proliferation Assay (Promega, Madison, Wis.) or sulforhodamine B (SRB) assay at the end of the exposure period (47, 48).

The human astrocyte cells were cultured from brains of deceased amyotrophic lateral sclerosis (ALS) patients (Uniform Anatomic Gift Act of 1987). The cerebrum was isolated from the other brain regions and meninges and placed in calcium and magnesium-free Hank's buffered salt solution (CMF-HBSS). The cerebrum was diced, incubated with trypsin/EDTA (Gibco BRL, Grand Island, N.Y.) and triturated with DNase. Tissue was passed through a 135 µm Nitex screen (SEFAR America, Depew, N.Y.), washed twice with CMF-HBSS, re-suspended in media (DMEM/10% FBS, 7.5 mM glucose, 4 mM L-glutamine, 1,000 U/mL penicillin, 1 ng/mL streptomycin, 2.5 µg/mL amphotericin B), centrifuged and passed through two sets of 35 µm Nitex screens. Dissociated cells was plated in poly-D-lysine pre-coated 175 cm² flasks. The mixed glial cultures were grown for 14 days, and then shaken to dislodge microglia cells and oligodendrocytes that were discarded. The pure astrocytes were attached to the bottom of the flask.

Bovine retinal endothelial cells (BRECs) were isolated and processed according to a previously published procedure (49, 50). In brief, BREC was grown in MCDB-131 media (Sigma, St) supplemented with 10% FBS, 10 ng/mL EGF, 0.2 mg/mL ENDO GRO (VEC Technologies, Inc.), 0.09 mg/ml heparin, and antibiotic/antimycotic (Invitrogen).

Example 1: Selection of Temodar®-Resistant Cell Lines

Figure 1A:
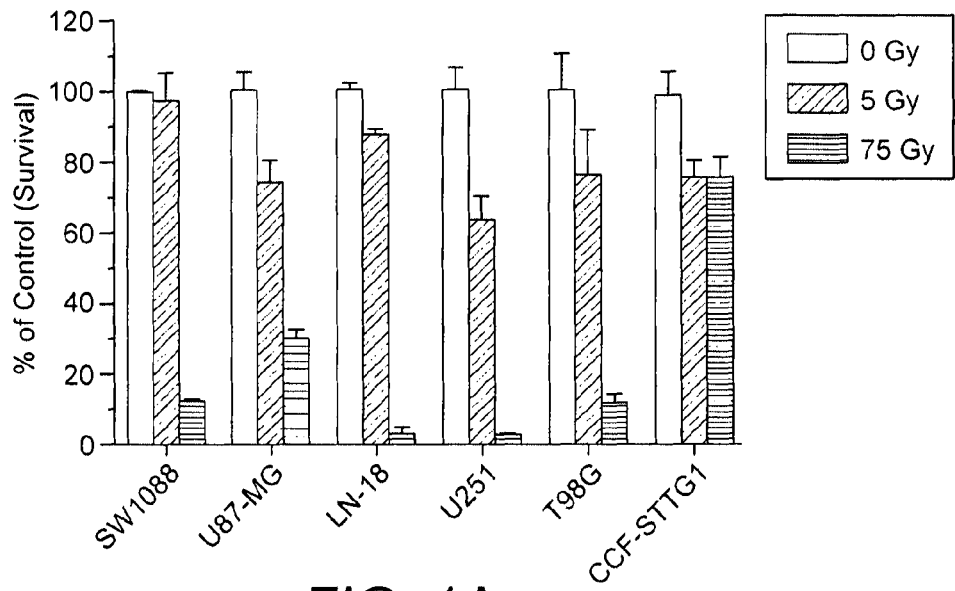
FIGS. 1A and 1B show cytotoxicity of either (FIG. 1A) radiation (GY=Gray units) or (FIG. 1B) Temodar® treatment on different glioma cell lines. Experiments described in Example 1.
Figure 1B:
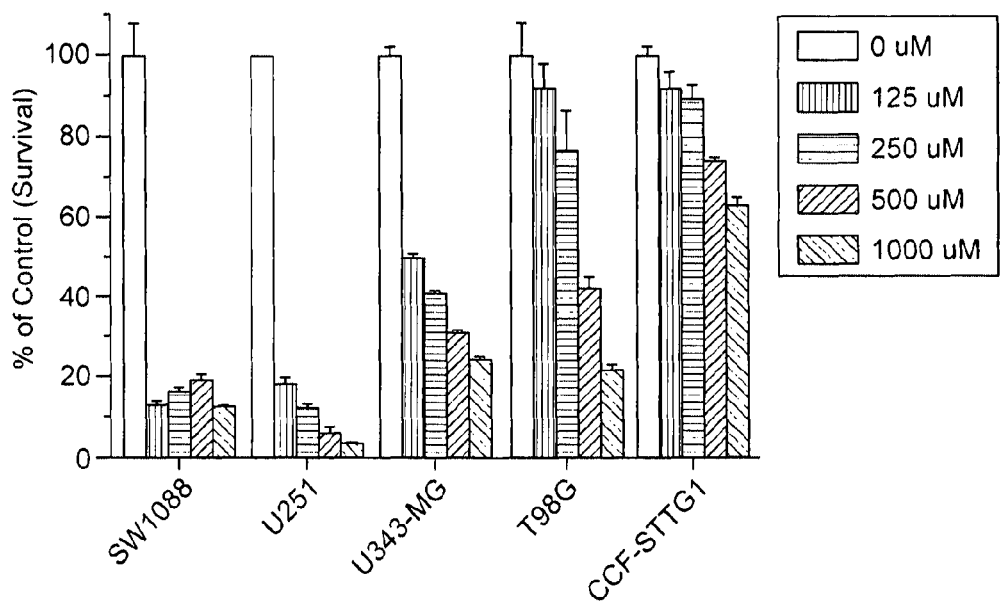

A screen for compounds that are cytotoxic to Temodar®-resistant cells was performed. The cytotoxicity of Temodar®) and radiation treatment was first determined on established glioma cell lines that express HFE (hemochromatosis gene) polymorphisms. The cells were exposed to a range of doses of Temodar® up to 1000 µM (FIG. 1) or a range of doses of γ-radiation (5 Gy, 75 Gy) for 3-6 days. FIG. 1A shows that the cell line, CCF-STTG1, was the most resistant to radiation. As shown in FIG. 1B, CCF-STTG1 cells were shown to be even more resistant to Temodar® toxicity than T98G and U-343MG, which are glioma cell lines currently used to model Temodar® resistance (51, 52).

Example 2: Identification of Chemotype Compound I (CC-I)

Temodar®-resistant cell lines were used to screen for compounds having the ability to decelerate the growth of, or kill, Temodar®-resistant cells. The efficacy of over 15,000 different compounds in the Drug Discovery Core at Pennsylvania State Hershey Medical Center was tested on Temodar®-resistant human neuroblastoma SH-SY5Y and human glioma CCF-STTG1 cell lines with a colorimetric cytotoxicity assay, the sulforhodamine B (SRB) assay (53). A lead compound, chemotype compound-I (CC-I), shown in FIG. 2A, was identified from the screen.

CC-I is a thiobarbituric acid analog that is highly toxic to Temodar®-resistant cells. The structure of CC-I is shown in FIG. 2A. FIG. 2B shows that the toxic effect of CC-I was dose-dependent in both Temodar®-resistant and Temodar®-sensitive glioma cells. CC-I was cytotoxic to the Temodar®-resistant CCF-STTG1 glioma cell line, LD50≈1.2 µg/ml (4.3 µM), but was even more cytotoxic to SW-1088 astrocytoma cells (LD50≈0.5 µg/ml or 1.7 µM). However, CC-I was not toxic to normal human astrocytes at concentrations toxic to Temodar®-resistant glioma cells, as shown in FIG. 2C. Furthermore, CC-I was not toxic to bovine retinal endothelial cells (BREC), a model for the blood-brain-barrier (FIG. 2D).

Example 3: CC-I Inhibits Glioma Cell Tumors in an In Vivo Model

The efficacy and toxicity of CC-I was tested in vivo using the athymic nude mouse subcutaneous tumor model. Ten million cells of the Temodar®-sensitive (SW1088) or Temodar®-resistant (CCF-STTG1) malignant glioma cell lines were injected into the flank of one-month-old, female athymic nude mice. When the tumor reached 32 mm$^3$ in size (week I on graph), CC-I (25 mg/kg) was injected intraperitoneally once a week for 7 weeks. CC-I so completely inhibited the growth of Temodar®-resistant CCF-STTG1 cell tumors that the line indicating the growth of this tumor is not visible on the graph of FIG. 3. In addition, the tumors recur in the Temodar®-resistant glioma injected nude mice when CC-I was discontinued (beyond 7 weeks) (FIG. 3). The body weight of the mice was not affected by CC-I (data not shown). No liver or kidney toxicity was observed in mice treated with CC-I (data not shown).

Example 4: CC-I Inhibits Intracranial Tumor Growth in an In Vivo Model

Figure 4A:
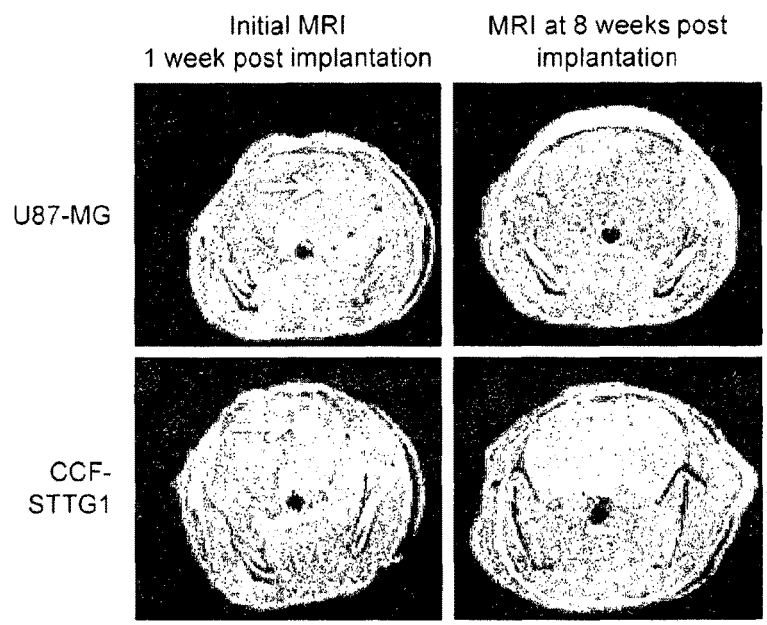
Figure 4B:
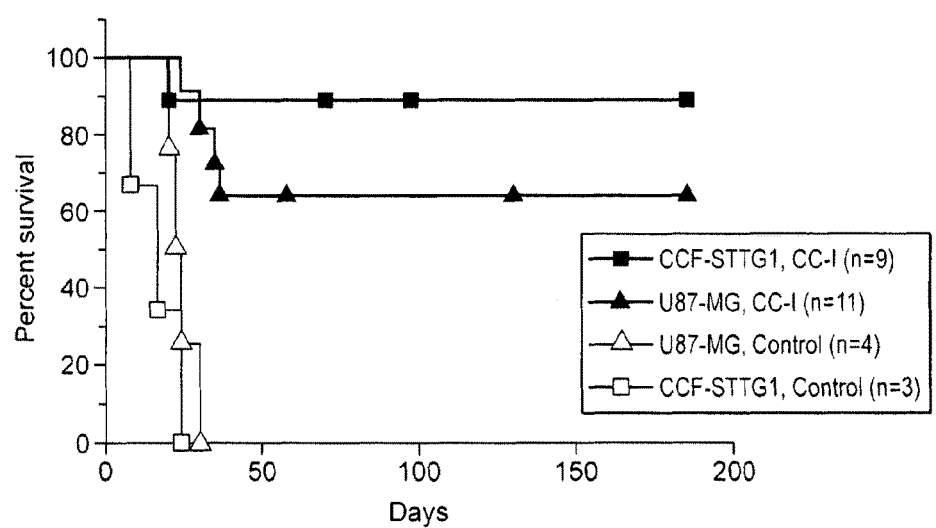
Figure 4C:
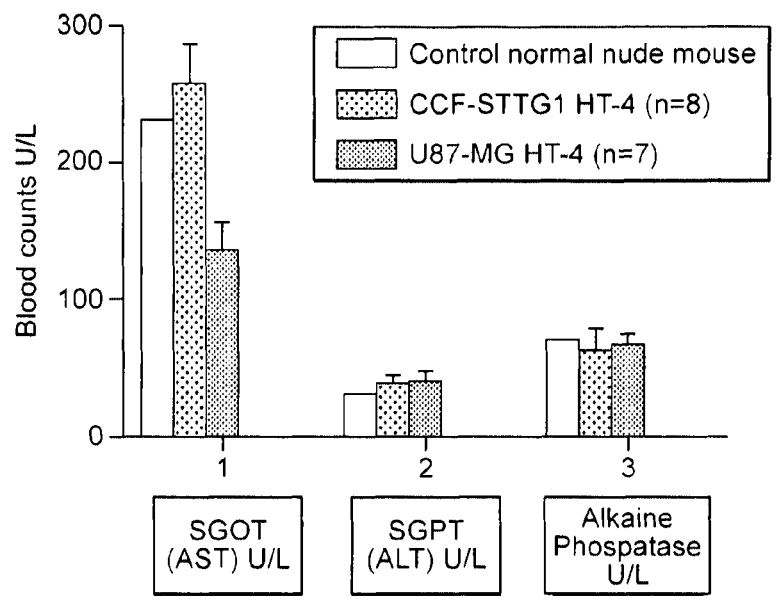
Figure 4D:
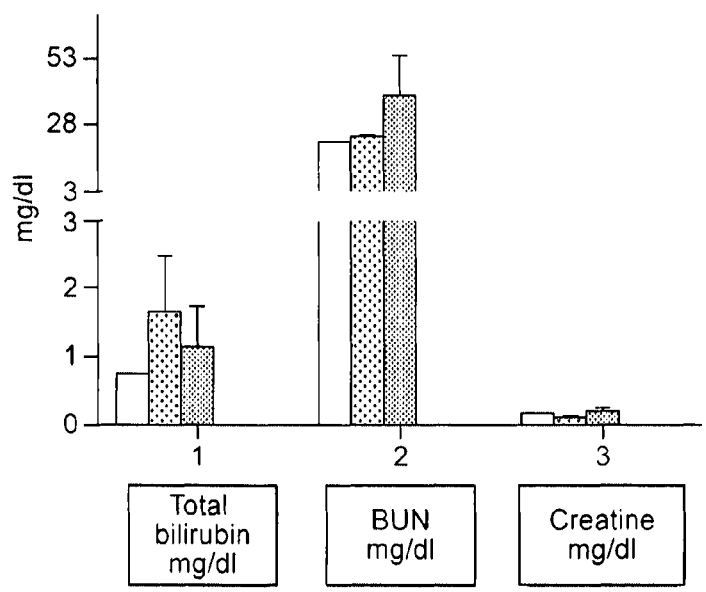

The effect of CC-I in an intracranial, orthotopic xenograft brain tumor model was analysed. The caudate putamen region of female, athymic nude mice was injected with 10$^6$ human U87-MG (Temodar®-sensitive) or CCF-STTG1 (Temodar®-resistant) glioma cells in a volume of 10 µl. At one week post-injection, tumor volume was measured using Ti weighted MRI contrast (7T MR imaging system). Thereafter, CC-I was injected intraperitoneally, once a week for 7 weeks at a concentration of 25 mg/kg body weight. Tumor size was measured weekly. As shown in FIGS. 4A and 4B, CC-I inhibited tumor growth in both Temodar (Z-resistant and Temodar®-sensitive tumors and extended survival in tumor-bearing mice. The arrows in the figure indicate brain tumors. No tumor bearing mice treated only with phosphate buffered saline (PBS), (untreated control mice), survived after 27 days, and the median survival was 20 days (Kaplan-Meier survival graph). Treatment with CC-I was effective at both reducing tumor size and extending the survival of the mice as shown in FIGS. 3, 4A and 4B. The body weight of mice receiving CC-I was not affected (data not shown). Liver and kidney toxicity (total bilirubin, blood urea nitrogen (BUN), creatine, aspartate aminotransferase (SGOT/AST), alanine aminotransferase (SGPT/ALT), and alkaline phosphatase) were also determined using an automated chemistry analyzer machine (Roche Cobase MIRA) and kits manufactured by Thermo Electron. The data indicate no liver or kidney toxicity in CC-I treated mice (FIG. 4C).

Example 5: CC-I Induces Apoptosis of CCF-STTG1 Astrocytoma Cells

An FITC-labeled Annexin V/propidium iodide apoptosis assay kit (Molecular Probes) was used to determine whether CC-I induces apoptosis in an astrocytoma cell line. As shown in FIG. 5, CC-I induced apoptosis in a dose dependent manner in CCF-STTG1 cells in vitro. The percentage of apoptotic cells by the CC-I treatment in CCF-STTG1 cells is from 10.9±0.16% at 5 pig/ml (18.1 M) to 48.7±0.33% at 10 µg/ml (36.2 µM). By comparison, the positive control, actinomycin D, induced apoptosis in 47.8±0.04% of the cells at 0.05 µg/ml (39.8 nM).

Example 6: CC-I Specifically Inhibits Topoisomerase IIα

To assess whether CC-I is a human topoisomerase IIα inhibitor, we determined the ability of CC-I to inhibit topoisomerase IIα activity using a kDNA decatenation assay. At concentrations greater than 6 µg/ml, CC-I completely inhibited topoisomerase IIα catalyzed kDNA decatenation, as shown in FIG. 6A. Molecular modeling demonstrates that the inhibitory effect of CC-I on topoisomerase IIα can be optimized. FIG. 6B shows space on both sides of CC-I that can accommodate additional groups to enhance binding. Based on the polarity and hydrophobicity of the residues in the binding site, as shown in FIG. 6B, more effective inhibitors can be developed by selectively adding different groups in the remaining space of the binding site.

To determine whether CC-I is a specific inhibitor of topoisomerase I or IIα, the ability of CC-I to inhibit topoisomerases I and IIα activity was examined using a supercoiled DNA relaxation assay. The results, presented in FIG. 7A, demonstrate that CC-I did not inhibit topoisomerase 1-mediated relaxation of supercoiled pBR322 DNA. In contrast, CC-I exhibited a strong inhibitory effect on topoisomerase IIα (FIG. 7B). The most effective concentration of CC-I on topoisomerase IIα activity was 3 µg/ml (FIG. 7B), whereas concentrations as high as 50 µg/ml had no effect on topoisomerase I activity (FIG. 7A), demonstrating that CC-I is a topoisomerase IIα specific inhibitor.

Example 7: Effect of CC-I on a Neuroblastoma Tumor In Vivo

To determine the effect of CC-I on neuroblastoma, an in vivo subcutaneous tumor model in SCID mice was examined. One month old, female SCID mice were injected subcutaneously in the flank region with a Temodar®- and radiation-resistant C282Y HFE variant expressing neuroblastoma SH-SY5Y cells. After the tumor attained a volume of 32 mm$^3$, CC-I (25 mg/kg) was injected intraperitoneally once a week for 7 weeks. As shown in FIG. 8A, CC-I completely inhibited tumor growth. No liver or kidney toxicity was observed in the treated mice (FIGS. 8, B and C), and body weight was unaffected by CC-I (data not shown).

Example 8: Effect of CC-I on Neurofibroma Cells In Vitro

Cells of established neurofibroma cell lines were plated at a density of 2000-4000 cells per well in 96 well plates under standard cell culture conditions (54) and then exposed to CC-I for 2 days. As shown in FIG. 9, CC-I was cytotoxic to all neurofibroma lines tested. The LD50 for ST88 and NF215 neurofibroma cells are 2.1 µg/ml and 1.4 µg/ml, respectively.

Example 9: CC-I is Cytotoxic to Ovarian Cancer Cells In Vitro

Human ovarian adenocarcinoma SKOV-3 cell lines were ordered from American Type Culture Collection (ATCC, Manassas, Va.), and maintained in McCoy's 5A media with 100 U/ml penicillin, 100 µg/ml streptomycin, and 10% FBS. To assess the effect of CC-I on the ovarian cancer cells, the cells were cultured overnight at a density of 5,000 to 10,000 cells per well in 96 well plates. Then the cells were treated with different concentrations of CC-I (Formula IV) or Formula V for another 3-6 days before cytotoxicity assay using MTS or SRB assay. The $IC_{50}$ or $LD_{50}$, 50% inhibition or lethal dose, of compounds is also determined using statistical software (GraphPad) as a general indicator of toxicity.

The $IC_{50}$ data indicate that CC-I is cytotoxic not only to gliomas but also other types of cancers such as neurofibromas, ovarian cancer, and neuroblastoma. As shown in Table 1, for example, CC-I was toxic to ovarian (OVCAR-3, IC50=3.5/4.3 µM) cancer and breast cancer cells lines.

Example 10: CC-I and its Chemotype Moiety Compounds are Cytotoxic to CCF-STTG1 Cells that are Resistant to Geldanamycin and Temodar®, and Temodar® Sensitive U87-MG Cell Lines Geldanamycin is an antibiotic that is currently being tested for treatment of solid tumors and non-Hodgkins lymphoma. Geldanamycin binds to Hsp90 and affects cell growth, cell survival and apoptosis. We have previously demonstrated a neuroblastoma cell line (C282Y-SH-SH5Y) and a glioma cell line (CCF-STTG1) that are resistant to Temodar® or geldanamycin compounds (48). However, as shown in Table 1, CC-I is cytotoxic to these neuroblastoma cells at low doses.

Chemotype moiety compounds of CC-I were also tested on the Temodar-resistant CCF-STTG1 and Temodar®-sensitive U87-MG cell lines. The glioma cell culture and treatment is as described above. As shown in FIG. 10, among tested compounds, Formulae V-VIII were cytotoxic to Temodar®-resistant CCF-STTG1 cell lines. Formula V exhibited the greatest toxicity. The toxic effect of Formula V was dose-dependent in Temodar®-resistant CCF-STTG1 and Temodar®-sensitive U87-MG glioma cells. Formula V was cytotoxic to Temodar®-resistant glioma CCF-STTG1 cell lines at approximately 0.8 µg/ml (3.0 µM) of $LD_{50}$ and even more cytotoxic to SW-1088 astrocytoma cells ($LD_{50}$: 0.3 µg/ml or 1.2 µM). The IC50 of Formula V on other cell lines is indicated in Table 1.

Additional chemotype moiety compounds [2-Thioxo-dihydro-pyrimidine-4,6-dione] of CC-I were tested on both Temodar®-resistant CCF-STTG1 and Temodar®-sensitive U87-MG cell lines. As shown in FIG. 11, Formulae IX, X, and XI exhibited a similar or even greater effect than CC-I on both cell lines. In addition, as shown in FIG. 12, Formulae XII-XV exhibited specific cytotoxicity to the CCF-STTG1 cell lines.

Example 11: Comparison of Cytotoxicity of CC-I and Other Topoisomerase 11 Inhibitors to Human Glioma CCF-STTG1 and U87-MG Cell Lines The human glioma CCF-STTG1 cell lines were plated at a density of 5,000 cells per well in 96 well plates under standard DMEM cell culture conditions and then exposed to different concentrations of CC-I, merbarone, or ICRF-193 for 5 days. Merbarone and ICRF-193 are both topoisomerase II inhibitors (55, 56). As shown in FIG. 12, CC-I was more cytotoxic to CCF-STTG1 and U87-MG cell lines than merbarone or ICRF-193, suggesting that CC-I is a better anti-tumor compound than either merbarone or ICRF-193.

Example 12—Anti-Tumor Effect of CC-I on the A549 Subcutaneous Lung Cancer Mouse Model To determine anti-tumor effect of CC-I against lung cancer, female athymic nude mice (nu/nu, sixteen week old, Charles River Laboratories) were implanted with $7 \times 10^6$ cells per mouse subcutaneously with A549 lung cancer cell lines. When the tumor reached approximately 100 mm³ in size (approximately 7-10 days after injection), CC-I was injected intraperitoneally at a concentration of 25 mg/kg body weight in a volume of 200 µL in 12.5% ethanol once a week for 7 weeks. The stock concentration of CC-I (50 mg/ml in 100% DMSO) was diluted 20 fold with 12.5% ethanol in phosphate-buffered saline (PBS). The control mouse group was given 5% DMSO and 12.5% ethanol in PBS in the same volume and dose regiment. Tumor size was measured weekly for 7 weeks by an investigator blinded to experimental conditions using a Vernier caliper. Tumor volume (V) was calculated according to the formula V=a2/2×b, where a and b are minor and major axes of the tumor foci, respectively. The tumor size, health, and survival of the mice were monitored daily and the tumor size measured weekly. To monitor the toxicity of compounds, the animals were weighed weekly FIG. 14 shows the tumor size in the CC-I treated mice as compared to the control group.

Example 13—Embodiment 2—Antitumor Effect of Test and Comparative Compounds on U87-MG Cells Cells U87-MG cells were obtained from the ATCC, LGC Standards (#HTB-14). The cells were screened for *mycoplasma* (*Mycoplasma* Experience) and maintained in Biowhittaker Alpha MEM (Lonza #BE02-002F+10% dialyzed US FBS serum (Invitrogen #26400-044), 1% Penstrep (Gibco #15140-122).

Assay

Compounds to be tested were transferred into column 1 of a hit plate (96-well PPV Greiner #651201). 20 ul of DMSO was added to columns 2 to 11. The top concentration was 10 mM.

Serial dilution, ten-point one in three dilution curves were created using Perkin Elmer Janus (20 ul clear Robopack disposable tips #6000677 used).

2 ul of each of the compounds was transferred by pre-dispensing into black, clear bottom 96-well CellBIND Corning plates (Fisher #DPS-184-030R) using Platemate 2×2 (ThermoFisher Darts #5506).

200 µl of U87-MG cells were added to columns 1 to 11 at a density of 1000 cells per ml, and media only was dispensed into control column 12 using Wellmate (Small bore tubing set #201-30002).

After 5 days (120 hrs) incubation at 37° C. under 5% $CO_2$ in a humidified incubator, the assay was "stopped" by addition of Resazurin sodium salt at 0.5 mM final concentration (Sigma R7017). The plates were incubated for a further 4 hrs before resorufin readout was taken from a Perkin Elmer EnVision, 550 nm excitation (photo550, Barcode 312), 580 nm emission (M580, Barcode 233), Top Mirror BODIPY (D555, Barcode 405).

The results are depicted in Table 2b below. The activity score was assigned based upon the relationships in Table 2a:

TABLE 2a

| Mean pXC50 | Activity Score |
|---|---|
| ≥6.0 | ++++ |
| 5.0-<6.0 | +++ |
| 4.5-<5.0 | ++ |
| 4.0-<4.5 | + |
| <4.0 | − |

TABLE 2b

| Compound ID | Activity Score |
|---|---|
| DDD00175302 | ++++ |
| DDD00175286 | ++++ |
| DDD00175297 | ++++ |
| DDD00175339 | +++ |
| DDD00197347 | +++ |
| DDD00197332 | +++ |
| DDD00175832 | +++ |
| DDD00175285 | +++ |
| DDD00197351 | +++ |
| DDD00175834 | +++ |
| DDD00197357 | +++ |
| DDD00197344 | +++ |
| DDD00175271 | +++ |
| DDD00124809 | +++ |
| DDD00197341 | +++ |
| DDD00175841 | +++ |
| DDD00197338 | +++ |
| DDD00175794 | +++ |
| DDD00175808 | +++ |
| DDD00175811 | +++ |
| DDD00175796 | +++ |
| DDD00175801 | +++ |
| DDD00175810 | +++ |
| DDD00197355 | +++ |
| DDD00197346 | +++ |
| DDD00175799 | +++ |
| DDD00197330 | +++ |
| DDD00197329 | +++ |
| DDD00197331 | +++ |
| DDD00175797 | +++ |
| DDD00175817 | +++ |
| DDD00175818 | +++ |
| DDD00197343 | +++ |
| DDD00197349 | +++ |
| DDD00175809 | +++ |
| DDD00125643 | +++ |
| DDD00175819 | +++ |
| DDD00197348 | +++ |
| DDD00175789 | +++ |
| DDD00175804 | +++ |
| DDD00175805 | +++ |
| DDD00175842 | +++ |
| DDD00197339 | +++ |
| DDD00175813 | +++ |
| DDD00175798 | +++ |
| DDD00197337 | ++ |
| DDD00175802 | ++ |
| DDD00175803 | ++ |
| DDD00124808 | ++ |
| DDD00197354 | ++ |
| DDD00124818 | ++ |
| DDD00197336 | ++ |
| DDD00175792 | ++ |
| DDD00175816 | ++ |
| DDD00124807 | ++ |
| DDD00197350 | ++ |
| DDD00124802 | ++ |
| DDD00197709 | ++ |

TABLE 2b-continued

| Compound ID | Activity Score |
|---|---|
| DDD00124821 | + |
| DDD00175281 | + |
| DDD00175840 | + |
| DDD00175806 | + |
| DDD00175800 | + |
| DDD00175830 | + |
| DDD00175795 | + |
| DDD00175293 | + |
| DDD00175835 | + |
| DDD00197345 | + |
| DDD00197342 | + |
| DDD00175826 | + |
| DDD00175839 | + |
| DDD00175807 | + |
| DDD00175280 | − |
| DDD00175332 | − |
| DDD00175338 | − |
| DDD00175790 | − |
| DDD00175791 | − |
| DDD00175820 | − |
| DDD00175821 | − |
| DDD00175822 | − |
| DDD00175823 | − |
| DDD00175824 | − |
| DDD00175825 | − |
| DDD00175827 | − |
| DDD00175828 | − |
| DDD00175831 | − |
| DDD00175833 | − |
| DDD00175836 | − |
| DDD00175837 | − |
| DDD00175838 | − |
| DDD00197352 | − |
| DDD00197671 | − |

The compound ID (a DDD number) for the active compounds has already been identified with the compound structure in the description above. The comparative compounds (inactive) in Table 2b have the following structures:

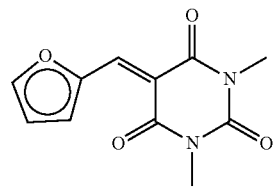
DDD00175280

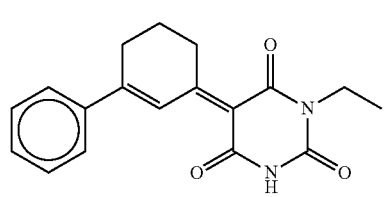
DDD00175332

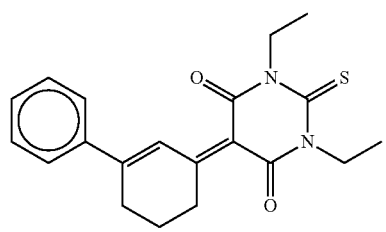
DDD00175338

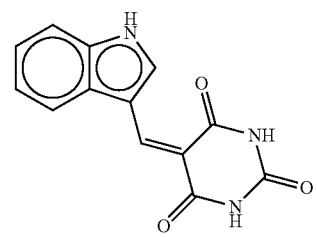
DDD00175790
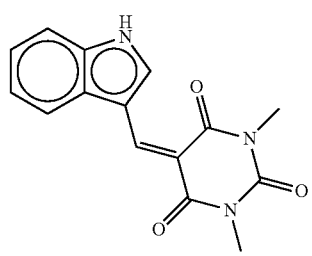
DDD00175791
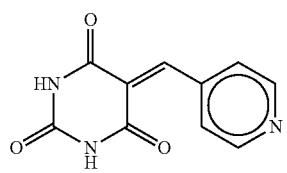
DDD00175820
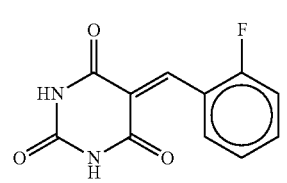
DDD00175821
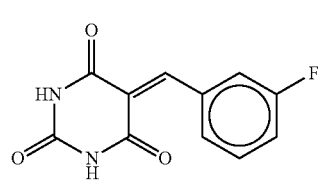
DDD00175822
DDD00175823
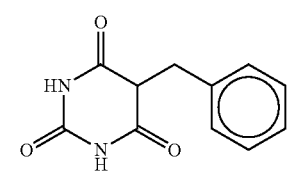
DDD00175824
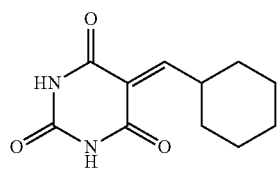
DDD00175825
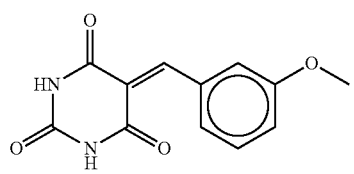
DDD00175827
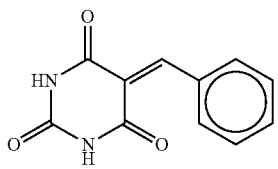
DDD00175828
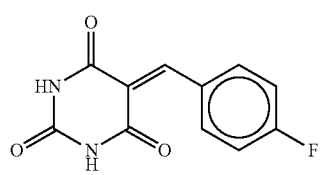
DDD00175831
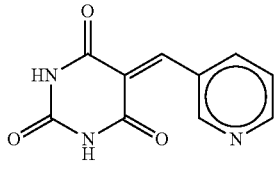
DDD00175833
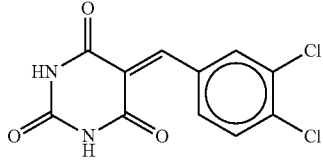
DDD00175836
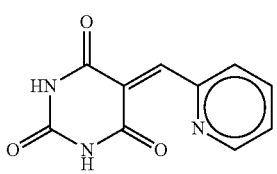
DDD00175837
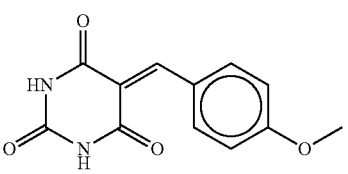
DDD00175838
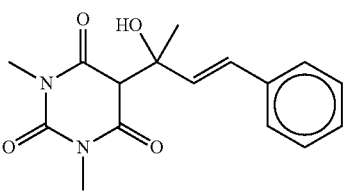
DDD00197352

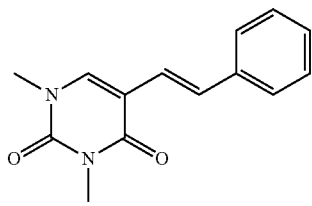

DDD00197671

The data clearly demonstrate that the barbiturate and thiobarbiturates compounds with the diene motif have good activity, whereas if the diene motif is replaced by single alkene substituents, whether conjugated with the barbiturate system or not, activity is lost.

Example 14—Embodiment 2—Antitumor Effect of Test and Comparative Compounds on Other Cells In this assay, cell lines were tested broadly using the same method as the U87 cell line assay of Example 13. NCI-H1299, CCF-STTG1 and Hep G2 cells were obtained from the ATCC. These cell lines were tested as previously described with the following modifications. NCI-H1299, CCF-STTG1 were maintained in RPMI-1640 Medium plus 10% fetal bovine serum and 1% penicillin/streptomycin, while Hep G2 cells were maintained in Eagle's Minimum Essential Medium plus 10% fetal bovine serum and 1% penicillin/streptomycin. Cells were plated at a density of $1 \times 10^4$ per ml except CFF-STTG1 cells which were seeded at a density of $2.5 \times 10^4$ per ml.

The test compounds were compared against Temodar®, a comparable commercially available remedy. The results are shown in Table 3. The scale is as employed in Table 2a.

TABLE 3

| Compound ID | Lung - Non small cell lung carcinoma NCI-H1299 pXC50 | Liver - Hepatocellular carcinoma Hep G2 pXC50 | Brain - Astrocytoma CCF-STTG1 pXC50 | Brain - Glioblastoma U87 pXC50 |
|---|---|---|---|---|
| DDD00124802 | +++ | ++ | + | + |
| DDD00124807 | +++ | ++ | ++ | ++ |
| DDD00124808 | +++ | ++ | ++ | ++ |
| DDD00124809 | nd | +++ | +++ | +++ |
| DDD00124818 | +++ | − | ++ | ++ |
| DDD00124821 | ++ | − | ++ | + |
| DDD00125643 | nd | ++ | +++ | +++ |
| Temodar ® | − | − | − | ++ |

Employing the same activity scale as in Table 2a in Example 13, the results of these tests clearly show that the compounds have activity against a variety of different cancers (nd=test not done).

It is also interesting to note that some test compounds are more active than the commercially available Temodar®, in some cases even against glioma for which use Temodar® is approved. Temodar® has no detectable activity against lung, liver and astrocytoma cells, whereas the compounds of the invention show very good activity, in many cases far higher activity than Temodar® has for its approved use. These results demonstrate the utility of the compounds of the invention for use against a wide variety of cancers.

REFERENCES

1. Drablos F, Feyzi E, Aas P A, Vaagbo C B, Kavli B, Bratlie M S, Pena-Diaz J, Otterlei M, Slupphaug G, Krokan H E. 2004. Alkylation damage in DNA and RNA—repair mechanisms and medical significance. DNA Repair (Amst) 3:1389-1407.
2. Schiff D. 2007. Temozolomide and radiation in low-grade and anaplastic gliomas: temoradiation. Cancer Invest 25:776-784.
3. Friedman H S, Kerby T, Calvert H. 2000. Temozolomide and treatment of malignant glioma. Clin Cancer Res 6:2585-2597.
4. Quirt I, Verma S, Petrella T, Bak K, Charette M. 2007. Temozolomide for the treatment of metastatic melanoma: a systematic review. Oncologist 12:1114-1123.
5. Atallah E, Flaherty L. 2005. Treatment of metastatic malignant melanoma. Curr Treat Options Oncol 6:185-193.
6. van Brussel J P, Busstra M B, Lang M S, Catsburg T, Schroder F H, Mickisch G H. 2000. A phase II study of temozolomide in hormone-refractory prostate cancer. Cancer Chemother Pharmacol 45:509-512.
7. Strosberg J R, Fine R L, Choi J, Nasir A, Coppola D, Chen D T, Helm J, Kvols L. 2011. First-line chemotherapy with capecitabine and temozolomide in patients with metastatic pancreatic endocrine carcinomas. Cancer 117:268-275.
8. Moore M J, Feld R, Hedley D, Oza A, Siu L L. 1998. A phase II study of temozolomide in advanced untreated pancreatic cancer. Invest New drugs 16:77-79.
9. Jakob J, Wenz F, Dinter D J, Ströbel P, Hohenberger P. 2009. Preoperative intensity-modulated radiotherapy combined with temozolomide for locally advanced soft-tissue sarcoma. Int J Radiat Oncol Biol Phys 75:810-816.
10. Garcia del Muro X, Lopez-Pousa A, Martin J, Buesa J M, Martinez-Trufero J, Casado A, Poveda A, Cruz J, Bover I, Maurel J. 2005. Spanish Group for Research on Sarcomas. 2005. A phase II trial of temozolomide as a 6-week, continuous, oral schedule in patients with advanced soft tissue sarcoma: a study by the Spanish Group for Research on Sarcomas. Cancer 104:1706-1712.
11. Park D K, Ryan C W, Dolan M E, Vogelzang N J, Stadler W M. 2002. A phase II trial of oral temozolomide in patients with metastatic renal cell cancer. Cancer Chemother Pharmacol 50:160-162.
12. Sunkara U, Walczak J R, Summerson L, Rogers T, Eisenberger M, Denmeade S, Pili R, Huff C A, Sinibaldi V, Carducci M A. 2004. A phase II trial of temozolomide and IFN-alpha in patients with advanced renal cell carcinoma. J Interferon Cytokine Res 24:37-41.
13. Marchesi F, 2007, Triazene compounds: mechanism of action and related DNA repair systems, Pharmacol Res 56:275-287.
14. Friedman, H. S., McLendon, R. E., Kerby, T., Dugan, M., Bigner, S. H., Henry, A. J., Ashley, D. M., Krischer, J., Lovell, S., Rasheed, K., et al. 1998. DNA mismatch repair and O6-alkylguanine-DNA alkyltransferase analysis and response to Temodal in newly diagnosed malignant glioma. J Clin Oncol 16:3851-3857.
15. Hegi M E, Liu L, Herman J G, Stupp R, Wick W, Weller M et al. 2008. Correlation of 06-methylguanine methyltransferase (MGMT) promoter methylation with clinical outcomes in glioblastoma and clinical strategies to modulate MGMT activity. J Clin Oncol 26:4189-4199.
16. Passagne I, Evrard A, Depeille P, Cuq P, Cupissol D, Vian L. 2006. O(6)-methylguanine DNA-methyltransferase (MGMT) overexpression in melanoma cells induces resistance to nitrosoureas and temozolomide but sensitizes to mitomycin C. Toxicol Appl Pharmacol 211:97-105.

17. Boeckmann L, Nickel A C, Kuschal C, Schaefer A, Thoms K M, Schön M P, Thomale J, Emmert S. 2011. Temozolomide chemoresistance heterogeneity in melanoma with different treatment regimens: DNA damage accumulation contribution. Melanoma Res 21:206-216.
18. Momparler R L, Karon M, Siegel S E, Avila F. 1976. Effect of adriamycin on DNA, RNA, and protein synthesis in cell-free systems and intact cells. Cancer Res 36:2891-2895.
19. Foglesong P D, 1992, Doxorubicin inhibits human DNA topoisomerase I, Cancer Chemother Pharmacol 30:123-125.
20. Burden D A et al 1998, Mechanism of action of eukaryotic topoisomerase II and drugs targeted to the enzyme, Biochim Biophys Acta, 1400:139-154.
21. Schuette W 2001, Chemotherapy as treatment of primary and recurrent small cell lung cancer, 1:S99-107.
22. Plukker J T 1995, Neo-adjuvant chemotherapy with carboplatin . . . Anticancer Res 15:2357-2361.
23. McClendon, A. K., and Osheroff, N. 2007. DNA topoisomerase II, genotoxicity, and cancer. Mutat Res 623:83-97.
24. Capranico G, Zagotto G, Palumbo M. 2004. Development of DNA topoisomerase-related therapeutics: a short perspective of new challenges. Curr Med Chem Anticancer Agents 4:335-345.
25. Noguchi M, 2006, Endogenously produced ganglioside GM3 endows etoposide and doxorubicin resistance by up-regulating Bcl-2 expression in 3LL Lewis lung carcinoma cells. Glycobiology 16:641-650.
26. CBTRUS: 2011. CBTRUS Statistical Report: NPCR and SEER data from 2004-2007, in: Central Brain Tumor Registry of the United States.
27. American Cancer Society. Cancer Facts & FIGS. 2010. Atlanta: American Cancer Society; 2010.
28. Ries, L. A. G., Melbert, D., Krapcho, M., Stinchcomb, D. G., Howlader, N., Homer, M. J., Mariotto, A., Miller, B. A., Feuer, E. J., Altekruse, S. F., et al. 2008. SEER Cancer Statistics Review, 1975-2005, National Cancer Institute. Bethesda, Md., http://seer.cancer.gov/csr/1975_2005/, based on November 2007 SEER data submission, posted to the SEER web site.
29. Stupp R, Mason W P, van den Bent M J, et al. 2005. Radiotherapy plus concomitant and adjuvant temozolomide for glioblastoma. *N Engl J Med* 352:987-996.
30. Ferlay J, Autier P, Boniol M, Heanue M, Colombet M, Boyle P. 2007. Estimates of the cancer incidence and mortality in Europe in 2006. Ann. Oncol 18:581-592.)
31. Jemal A, Siegel R, Ward E, Hao Y, Xu J, Murray T, Thun M J. 2008. Cancer statistics, 2008. CA Cancer J Clin 58:71-96.
32. Herzog T J. 2004. Recurrent ovarian cancer: how important is it to treat to disease progression? Clin Cancer Res 10:7439-7449.
33. Ferrandina G, Petrillo M, Carbone A, Zannoni G, Martinelli E, Prisco M, Pignata S, Breda E, Savarese A, Scambia G. 2008. Prognostic role of topoisomerase-IIalpha in advanced ovarian cancer patients. Br J Cancer 98:1910-1915.
34. Faggad A, Darb-Esfahani S, Wirtz R, Sinn B, Sehouli J, Könsgen D, Lage H, Weichert W, Noske A, Budczies J, Miller B M, Buckendahl A C, Riske A, Eldin Elwali N, Dietel M, Denkert C. 2009. Topoisomerase IIalpha mRNA and protein expression in ovarian carcinoma: correlation with clinicopathological factors and prognosis. Mol Pathol 22:579-588.
35. Albadine R, Wang W, Brownlee N A, Toubaji A, Billis A, Argani P, Epstein J I, Garvin A J, Cousi R, Schaeffer E M, Pavlovich C, Netto G J. 2009. Topoisomerase IIalpha status in renal medullary carcinoma: immunoexpression and gene copy alterations of a potential target of therapy. J Urol 182:735-740.
36. MacGrogan G, Rudolph P, Mascarel Id I, Mauriac L, Durand M, Avril A, Dilhuydy J M, Robert J, Mathoulin-Pélissier S, Picot V, Floquet A, Sierankowski G, Coindre J M. 2003. DNA topoisomerase IIalpha expression and the response to primary chemotherapy in breast cancer. Br J Cancer 89:666-671.
37. Miettinen H E, Järvinen T A, Kellner U, Kauraniemi P, Parwaresch R, Rantala I, Kalimo H, Paljärvi L, Isola J, Haapasalo H. 2000. High topoisomerase IIalpha expression associates with high proliferation rate and poor prognosis in oligodendrogliomas. Neuropathol Appl Neurobiol 26: 504-512.
38. Bredel M, Piribauer M, Marosi C, Birner P, Gatterbauer B, Fischer I, Ströbel T, Rössler K, Budka H, Hainfellner J A. 2002. High expression of DNA topoisomerase IIalpha and Ki-67 antigen is associated with prolonged survival in glioblastoma patients. Eur J Cancer 38:1343-1347.
39. Wang Y H, Takanashi M, Tsuji K, Tanaka N, Shiseki M, Mori N, Motoji T. 2009. Level of DNA topoisomerase IIalpha mRNA predicts the treatment response of relapsed acute leukemic patients. Leuk Res 33:902-907.
40. Coss A, Tosetto M, Fox E J, Sapetto-Rebow B, Gorman S, Kennedy B N, Lloyd A T, Hyland J M, O'Donoghue D P, Sheahan K, Leahy D T, Mulcahy H E, O'Sullivan J N. 2009. Increased topoisomerase IIalpha expression in colorectal cancer is associated with advanced disease and chemotherapeutic resistance via inhibition of apoptosis. Cancer Lett 276:228-238.
41. Smith L, Watson M B, O'Kane S I, Drew P J, Lind M J, Cawkwell L. 2006. The analysis of doxorubicin resistance in human breast cancer cells using antibody microarrays. Mol Cancer Ther 5:2115-2120.
42. Lopez J P, Wang-Rodriguez J, Chang C, Chen J S, Pardo F S, Aguilera J, Ongkeko W M. 2007. Gefitinib inhibition of drug resistance to doxorubicin by inactivating ABCG2 in thyroid cancer cell lines. Arch Otolaryngol Head Neck Surg 133:1022-1027.
43. Gariboldi M B, Ravizza R, Riganti L, Meschini S, Calcabrini A, Marra M, Arancia G, Dolfini E, Monti E. 2003. Molecular determinants of intrinsic resistance to doxorubicin in human cancer cell lines. Int J Oncol 22:1057-1064.
44. Berge, S. M., Bighley, L. D., Monkhouse, D. C. 1977. Pharmaceutical Salts. J Pharm Sci 66:1-19.
45. Mautner, H. G., and Clayton, E. M. 1959. 2-Selenobarbiturates. Studies of some analogous oxygen, sulfur and selenium compounds. J Am Chem Soc 81:6270-6273.
46. Schmidt, H. 1921. Ethyl- and allylselenourea and their alkyl halides. Berichte der Deutschen Chemischen Gesellschaft [Abteilung] B: Abhandlungen 54B, 2067-2070.
47. Lee S Y, Patton S M, Henderson R J, and Connor J R. 2007. Consequences of expressing mutants of the hemochromatosis gene (HFE) into a human neuronal cell line lacking endogenous HFE. FASEB J 21(2): 564-576.
48. Lee S Y, Liu S, Mitchell R M, Slagle-Webb B, Hong Y-S, Sheehan J M., Connor J R. 2011. HFE polymorphisms influence the response to chemotherapeutic agents via induction of p16INK4A. Int J Cancer In press.
49. Maines L W, Antonetti D A, Wolpert E B, Smith C D. 2005. Evaluation of the role of P-glycoprotein in the uptake of paroxetine, clozapine, phenytoin and carbamazepine by bovine retinal endothelial cells. Neuropharmacology 49:610-617.
50. Cecchelli R, Dehouck B, Descamps L, Fenart L, Buee-Scherrer V V, Duhem C, Lundquist S, Rentfel M, Torpier G, Dehouck M P. 1999. In vitro model for evaluating drug transport across the blood-brain barrier. Adv Drug Deliv Rev 36:165-178.
51. Kanzawa T, Germano I M, Kondo Y, Ito H, Kyo S, Kondo S. 2003. Inhibition of telomerase activity in malignant glioma cells correlates with their sensitivity to temozolomide. Br J Cancer 89:922-929.
52. Uzzaman M, Keller G, Germano I M. 2007. Enhanced proapoptotic effects of tumor necrosis factor-related apoptosis-inducing ligand on temozolomide-resistant glioma cells. J Neurosurg 106:646-651.
53. Skehan, P., Storeng, R., Scudiero, D., Monks, A., McMahon, J., Vistica, D., Warren, J. T., Bokesch, H., Kenney, S., and Boyd, M. R. 1990. New colorimetric cytotoxicity assay for anticancer-drug screening. J Natl Cancer Inst 82:1107-1112.
54. Dilworth J T, Wojtkowiak J W, Mathieu P, Tainsky M A, Reiners J J Jr, Mattingly R R, Hancock C N. 2008. Suppression of proliferation of two independent NF1 malignant peripheral nerve sheath tumor cell lines by the pan-ErbB inhibitor CI-1033. Cancer Biol Ther 7:1938-1946.
55. Wang, L., and Eastmond, D. A. 2002. Catalytic inhibitors of topoisomerase II are DNA-damaging agents: induction of chromosomal damage by merbarone and ICRF-187. Environ Mol Mutagen 39:348-356.
56. Germe T, Hyrien O. 2005. Topoisomerase II-DNA complexes trapped by ICRF-193 perturb chromatin structure. EMBO Rep 6:729-735.

The invention claimed is:
1. A compound having one of the following formulae:

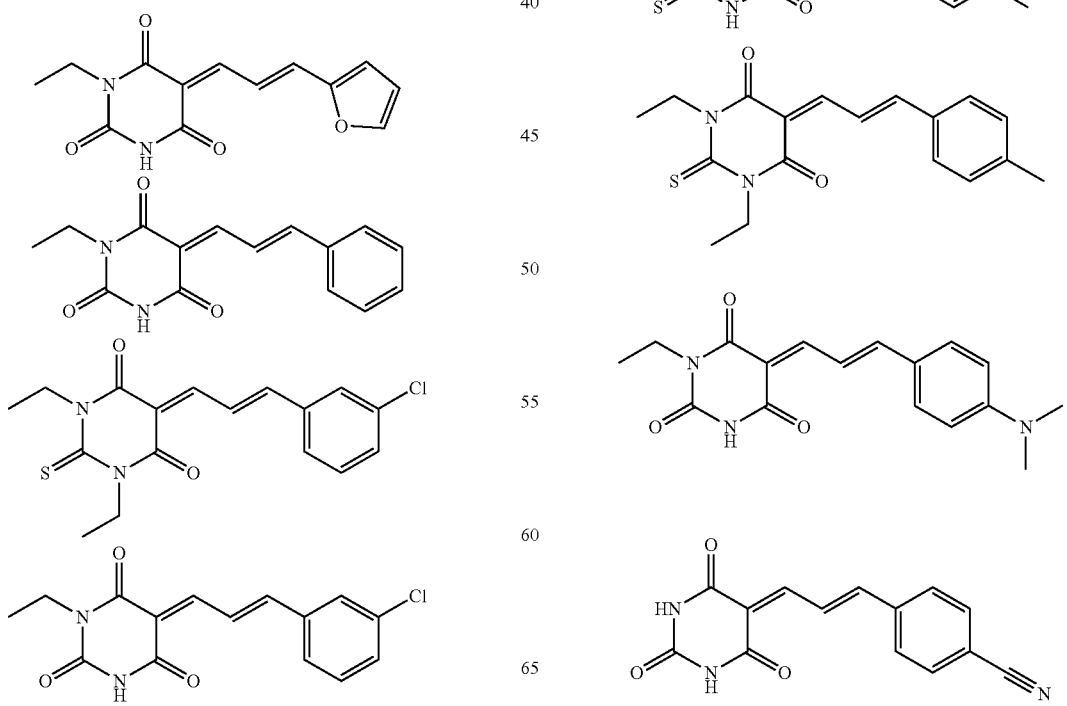

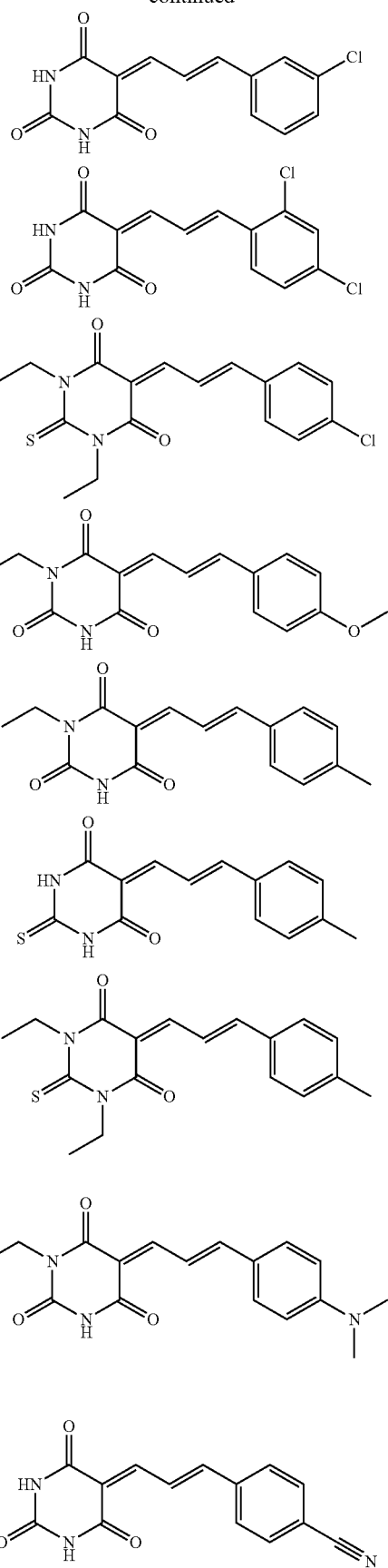

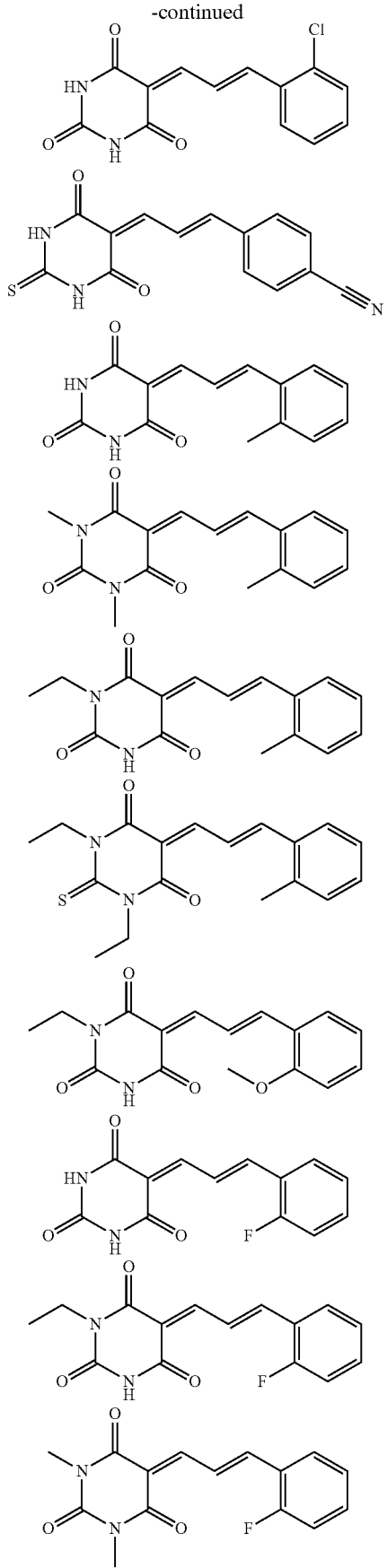
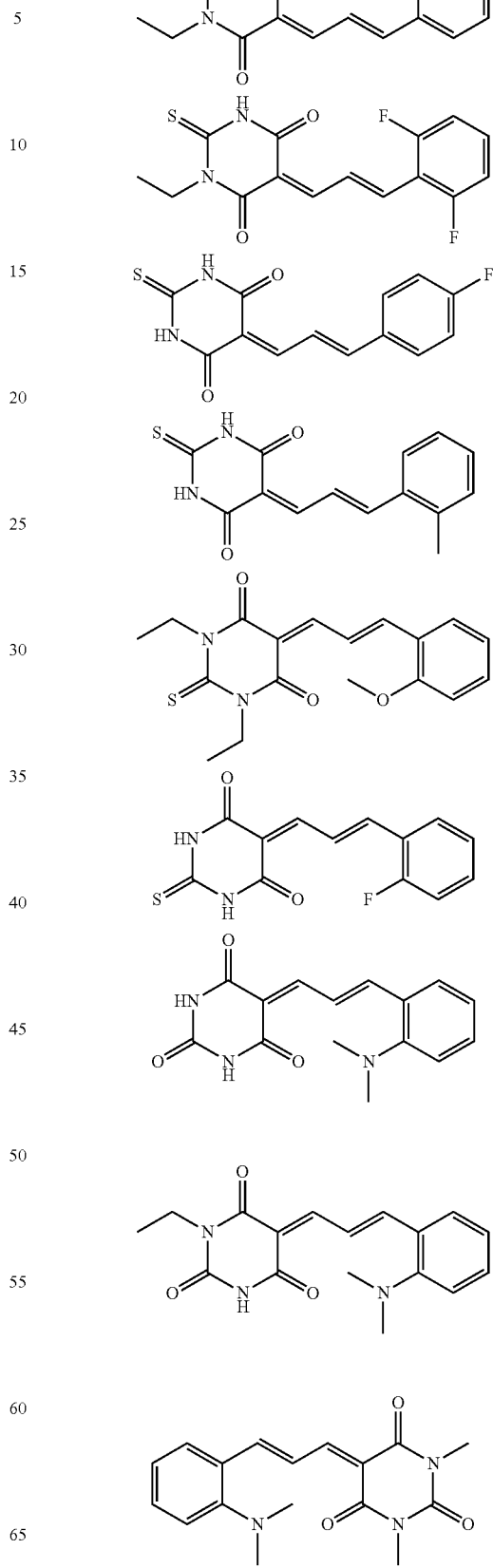

-continued
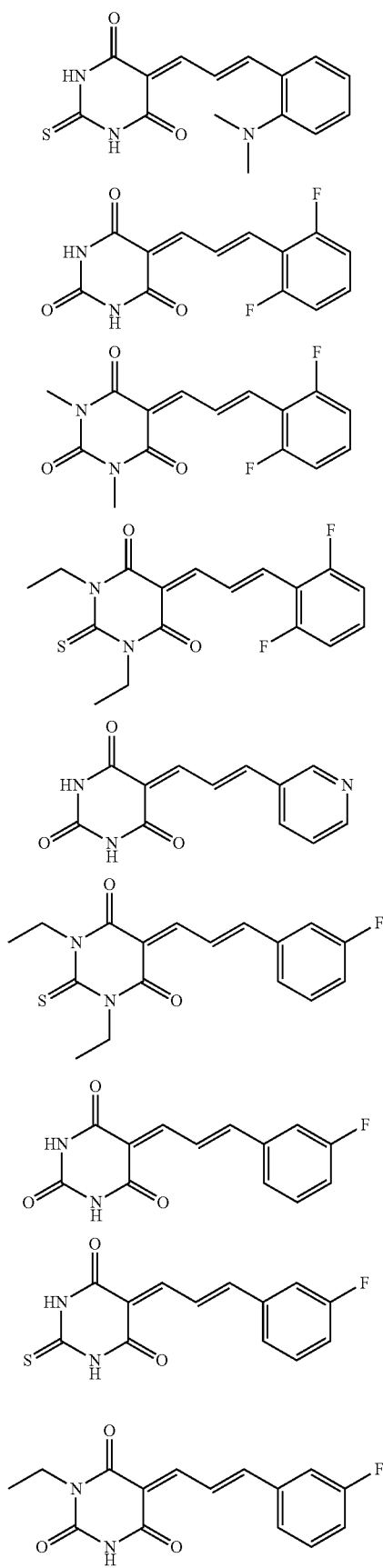
-continued
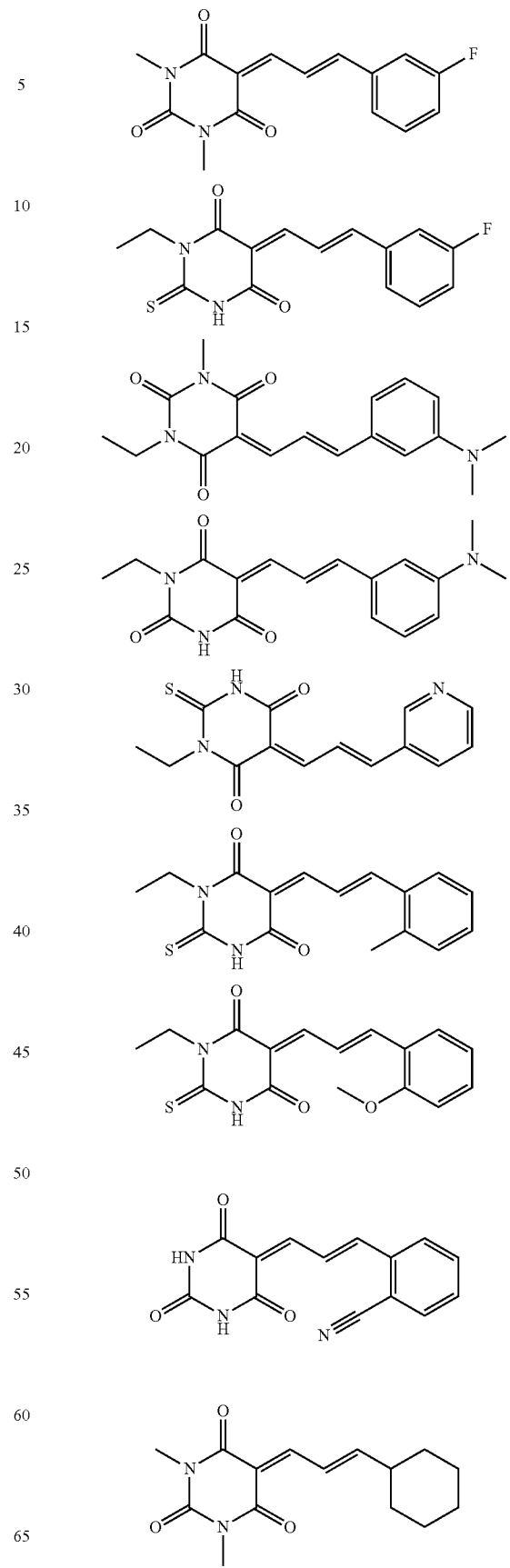

-continued
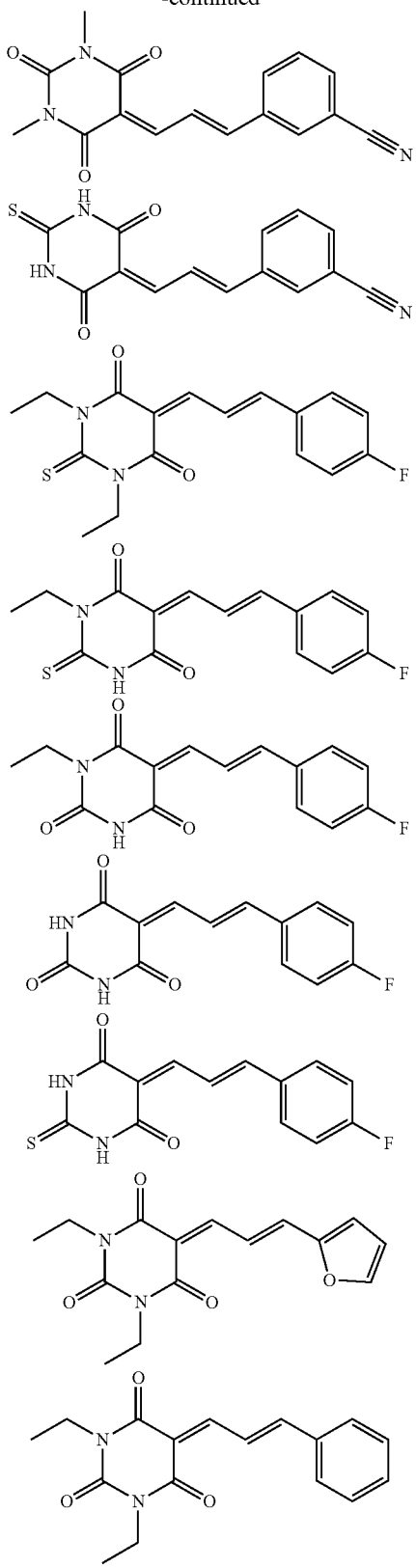
or a pharmaceutically acceptable salt or solvate thereof.
2. A compound according to claim 1, or a pharmaceutically acceptable salt thereof.
3. A compound according to claim 1 having one of the following formulae:
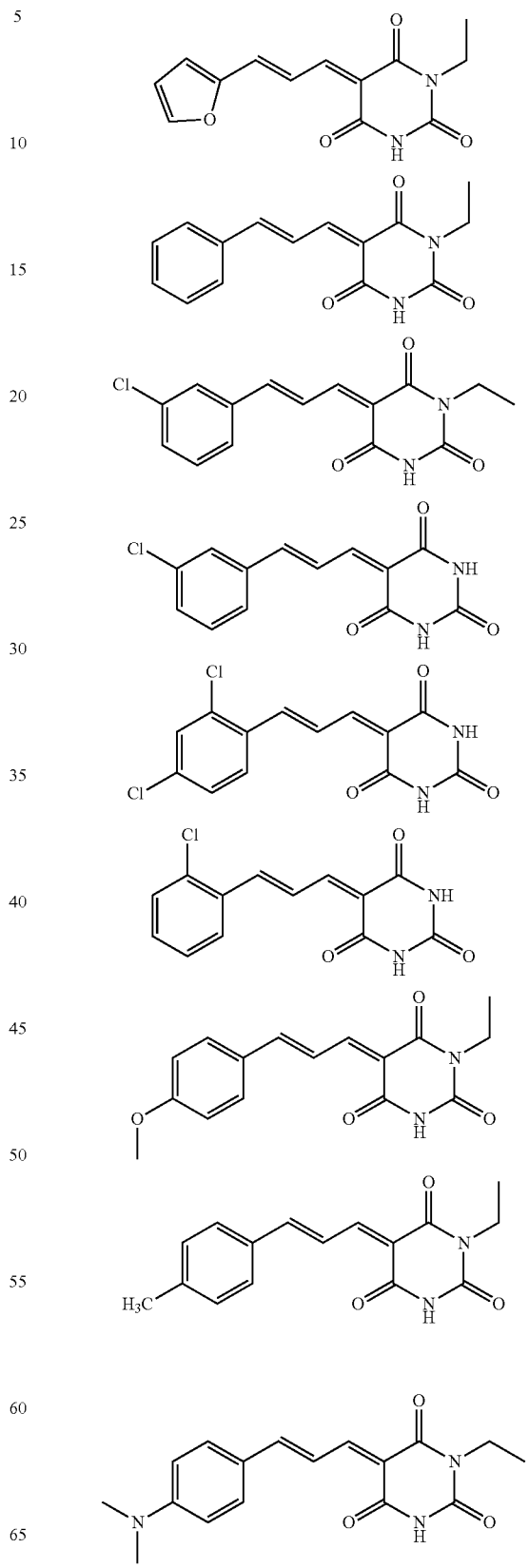

83
-continued
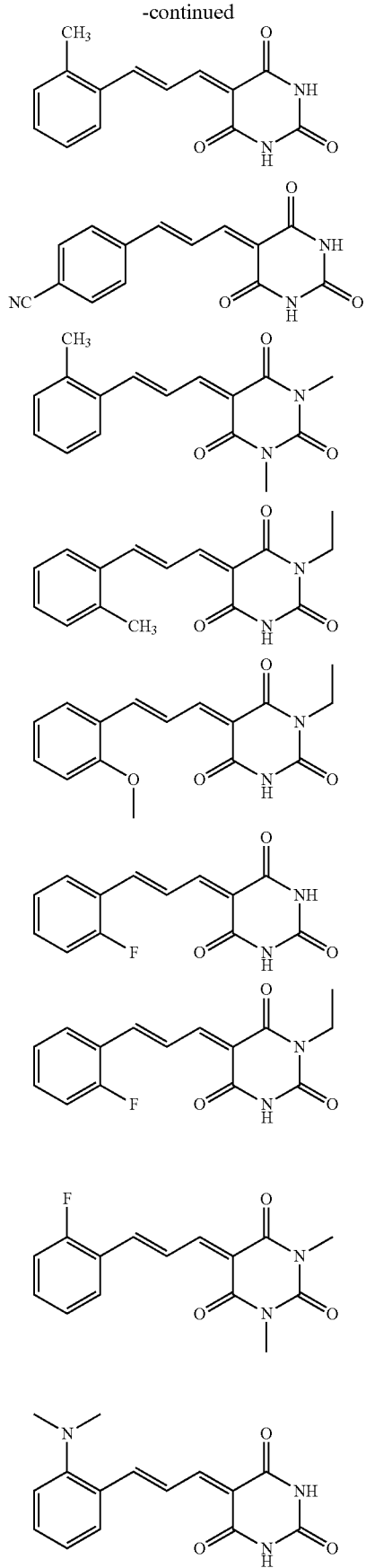
84
-continued
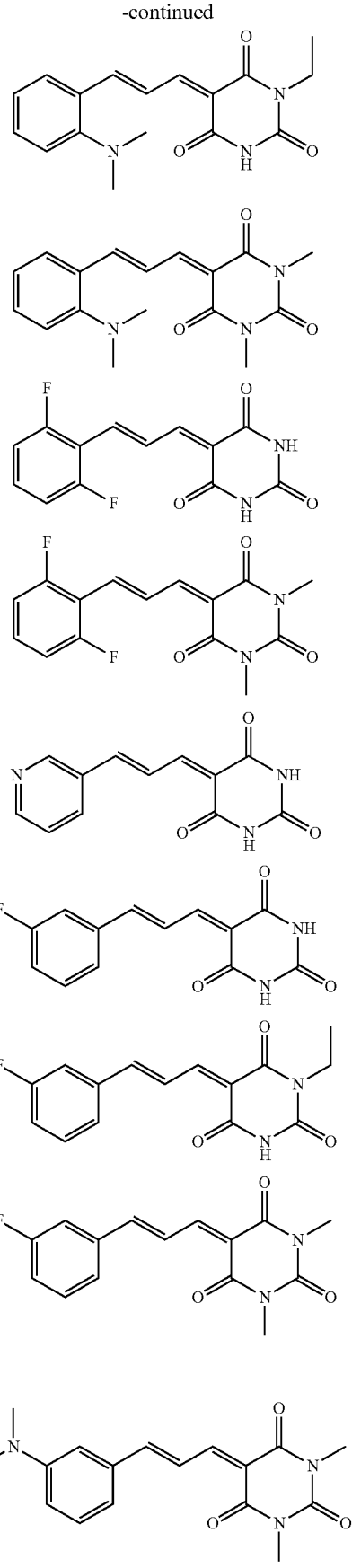

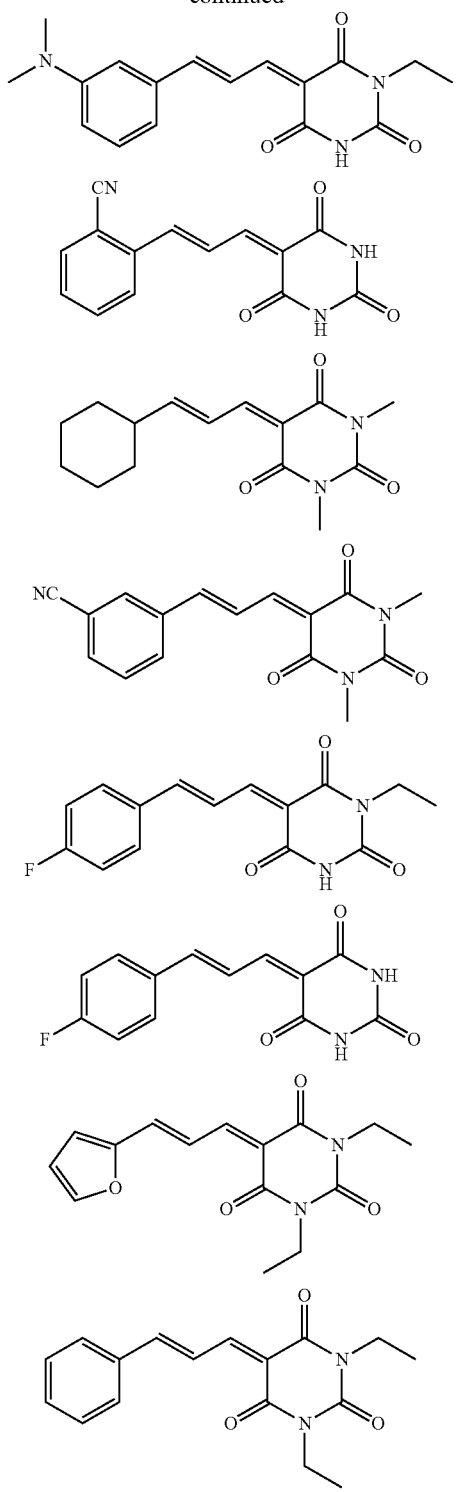
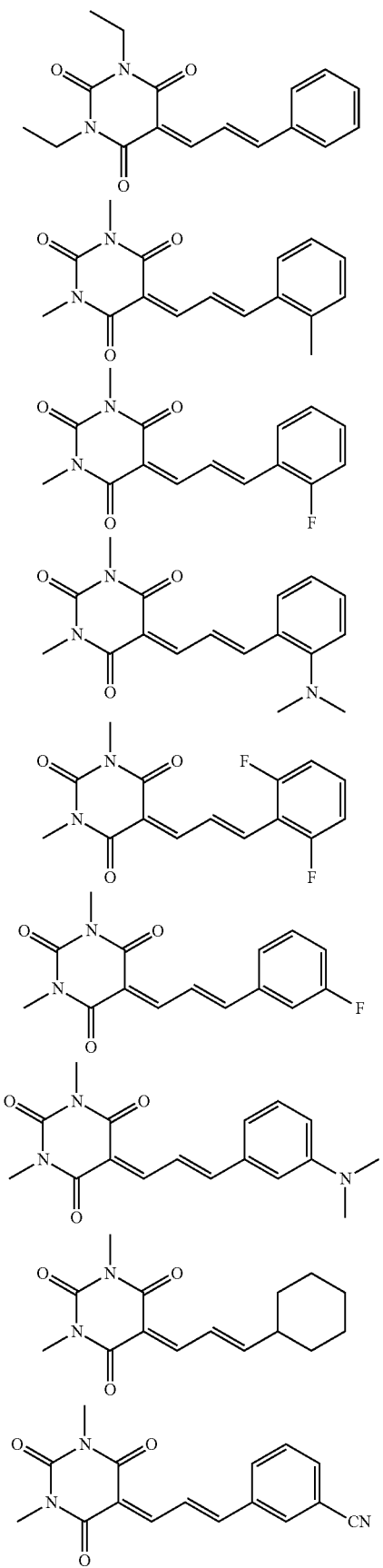
or a pharmaceutically acceptable salt or solvate thereof.
4. A compound according to claim 3, or a pharmaceutically acceptable salt thereof.
5. A compound according to claim 3 having one of the following formulae:

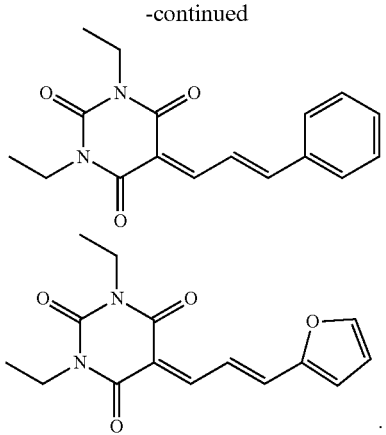

or a pharmaceutically acceptable salt or solvate thereof.

6. A compound according to claim 5, or a pharmaceutically acceptable salt thereof.

7. A compound according to claim 5 having the following formula:

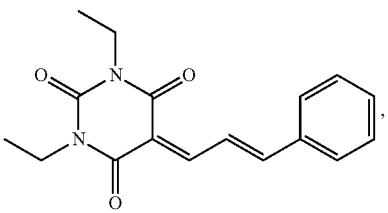 [SMILES: CCN1C(=O)C(=C/C=C/c2ccccc2)C(=O)N(CC)C1=O]

or a pharmaceutically acceptable salt or solvate thereof.

8. A compound according to claim 7, or a pharmaceutically acceptable salt thereof.

9. A pharmaceutical composition comprising a compound as defined in claim 1 or a pharmaceutically acceptable salt or solvate thereof, and a pharmaceutically acceptable diluent or carrier.

10. A pharmaceutical composition comprising a compound as defined in claim 2 or a pharmaceutically acceptable salt thereof, and a pharmaceutically acceptable diluent or carrier.

11. A pharmaceutical composition comprising a compound as defined in claim 3 or a pharmaceutically acceptable salt or solvate thereof, and a pharmaceutically acceptable diluent or carrier.

12. A pharmaceutical composition comprising a compound as defined in claim 4 or a pharmaceutically acceptable salt thereof, and a pharmaceutically acceptable diluent or carrier.

13. A pharmaceutical composition comprising a compound as defined in claim 5 or a pharmaceutically acceptable salt or solvate thereof, and a pharmaceutically acceptable diluent or carrier.

14. A pharmaceutical composition comprising a compound as defined in claim 6 or a pharmaceutically acceptable salt thereof, and a pharmaceutically acceptable diluent or carrier.

15. A pharmaceutical composition comprising a compound as defined in claim 7 or a pharmaceutically acceptable salt or solvate thereof, and a pharmaceutically acceptable diluent or carrier.

16. A pharmaceutical composition comprising a compound as defined in claim 8 or a pharmaceutically acceptable salt thereof, and a pharmaceutically acceptable diluent or carrier.

* * * * *